(12) United States Patent
Saus et al.

(10) Patent No.: US 7,935,492 B2
(45) Date of Patent: May 3, 2011

(54) GOODPASTURE ANTIGEN BINDING PROTEIN AND ITS DETECTION

(75) Inventors: Juan Saus, Valencia (ES); Fernando Revert, Moncada (ES)

(73) Assignee: Fibrostatin, Sociedad Limitada, Valencia (ES)

( * ) Notice: Subject to any disclaimer, the term of this patent is extended or adjusted under 35 U.S.C. 154(b) by 49 days.

(21) Appl. No.: 12/506,064

(22) Filed: Jul. 20, 2009

(65) Prior Publication Data
US 2010/0021935 A1 Jan. 28, 2010

Related U.S. Application Data

(60) Provisional application No. 61/082,741, filed on Jul. 22, 2008, provisional application No. 61/085,211, filed on Jul. 31, 2008.

(51) Int. Cl.
*G01N 33/53* (2006.01)
(52) U.S. Cl. .................................. 435/7.1; 435/7.92
(58) Field of Classification Search .................. None
See application file for complete search history.

(56) References Cited

U.S. PATENT DOCUMENTS

| 5,625,048 | A | 4/1997 | Tsien et al. |
|---|---|---|---|
| 5,660,827 | A | 8/1997 | Thorpe et al. |
| 6,124,128 | A | 9/2000 | Tsien et al. |
| 6,579,969 | B1 | 6/2003 | Saus |
| 7,147,855 | B2 | 12/2006 | Saus et al. |
| 7,186,527 | B2 | 3/2007 | Saus |
| 7,189,517 | B2 | 3/2007 | Saus |
| 7,326,768 | B2 | 2/2008 | Saus et al. |
| 2004/0175758 | A1 | 9/2004 | Saus et al. |
| 2007/0178540 | A1 | 8/2007 | Saus |

FOREIGN PATENT DOCUMENTS

| WO | WO 00/50607 | 8/2000 |
|---|---|---|
| WO | WO 02/061430 | 8/2002 |
| WO | WO 2004/070025 | 8/2004 |

OTHER PUBLICATIONS

Alpy and Tomasetto (2005), "Give lipids a START: the StAR-related lipid transfer (START) domain in mammals." J. Cell Sci. 118, 2791-2801.
Balow, J.E., Boumpas, D. T., and Austin III, H.A. "Systemic Lupus Erythematosus and the kidney". Systemic Lupus Erythematosus. Edited by Lahita RG. San Diego, Academic Press, 1999, pp. 657-685.
Bendtsen et al. (2004), "Feature-based prediction of non-classical and leaderless protein secretion." Protein Eng. Des. Sel. 17: 349-356.
Borza et al. (2005), "Goodpasture autoantibodies unmask cryptic epitopes by selectively dissociating autoantigen complexes lacking structural reinforcement: novel mechanisms for immune privilege and autoimmune pathogenesis." J. Biol. Chem. 280: 27147-27154.
Calvete et al. (2006), "Conformational diversity of the Goodpasture antigen, the noncollagenous-1 domain of the alpha3 chain of collagen IV." Proteomics 6: S237-S244.

Donadio and Grande (2002), "IgA nephropathy." N. Engl. J. Med. 347: 738-748.
Dowler et al. (2000), "Identification of pleckstrin-homology-domain-containing proteins with novel phosphoinositide-binding specificities." Biochem. J. 351: 19-31.
Evans et al. (1995), "Rapid expression of an anti-human C5 chimeric Fab utilizing a vector that replicates in COS and 293 cells." J. Immunol. Meth. 184: 123-38.
Fugmann et al. (2007), "Regulation of secretory transport by protein kinase D-mediated phosphorylation of the ceramide transfer protein." J. Cell Biol. 178: 15-22.
Granero et al. (2005), "A human-specific TNF-responsive promoter for Goodpasture antigen-binding protein." FEBS J. 272: 5291-5305.
Granero-Moltó et al. (2008), "Goodpasture antigen-binding protein and its spliced variant, ceramide transfer protein, have different functions in the modulation of apoptosis during zebrafish development." J. Biol. Chem. 283(29): 20495-504.
Haas M. "IgA Nephropathy and Henoch-Schönlein Purpura Nephritis". Heptinstall's Pathology of the Kidney. Edited by Jennette JC, Olson JL, Schwartz MM, Silva FG. Philadelphia, Lippincott Williams & Wilkins Publishers 2007, pp. 423-486.
Hanada et al. (2003), "Molecular machinery for non-vesicular trafficking of ceramide." Nature 426: 803-809.
Hudson et al. (2003), "Alport's syndrome, Goodpasture's syndrome, and type IV collagen." N. Engl. J. Med. 348: 2543-2556.
Kanekura et al. (2006), "Characterization of amyotrophic lateral sclerosis-linked P56S mutation of vesicle-associated membrane protein-associated protein B (VAPB/ALS8)." J. Biol. Chem. 281: 30223-30233.
Kawano et al. (2006), "Efficient trafficking of ceramide from the endoplasmic reticulum to the Golgi apparatus requires a VAMP-associated protein-interacting FFAT motif of CERT." J. Biol. Chem. 281: 30279-30288.
Kumagai et al. (2007), "Interorganelle trafficking of ceramide is regulated by phosphorylation-dependent cooperativity between the PH and START domains of CERT." J. Biol. Chem. 282: 17758-17766.
Lamour et al. (2007), "Ceramide kinase uses ceramide provided by ceramide transport protein: localization to organelles of eicosanoid synthesis." J. Lipid Res. 48: 1293-1304.
Lemmon and Ferguson (2000), "Signal-dependent membrane targeting by pleckstrin homology (PH) domains." Biochem J. 350: 1-18.
Loewen et al. (2003), "A conserved ER targeting motif in three families of lipid binding proteins and in Opi1p binds VAP." EMBO J. 22: 2025-2035.
Marquina et al. (2004), "Inhibition of B cell death causes the development of an IgA nephropathy in (New Zealand white x C57BL/6)F1-bcl-2 transgenic mice." J. Immunol. 172: 7177-7185.
Netzer et al. (1999), "The goodpasture autoantigen. Mapping the major conformational epitope(s) of alpha3(IV) collagen to residues 17-31 and 127-141 of the NC1 domain." J. Biol. Chem. 274: 11267-11274.
Ni and Lee (2007), "ER chaperones in mammalian development and human diseases." FEBS Lett. 581: 3641-3651.
Peabody (1989), "Translation initiation at non-AUG triplets in mammalian cells." J. Biol. Chem. 264: 5031-5035.
Perry and Ridgway (2006), "Oxysterol-binding protein and vesicle-associated membrane protein-associated protein are required for sterol-dependent activation of the ceramide transport protein." Mol. Biol. Cell. 17: 2604-2616.

(Continued)

*Primary Examiner* — Maher M Haddad
(74) *Attorney, Agent, or Firm* — McDonnell Bochnen Hulbert & Berghoff LLP

(57) ABSTRACT

The present invention provides native Goodpasture antigen binding protein isoforms, monoclonal antibodies directed against such proteins, and methods for their use.

13 Claims, 19 Drawing Sheets

OTHER PUBLICATIONS

Raya et al. (1999), "Characterization of a novel type of serine/threonine kinase that specifically phosphorylates the human goodpasture antigen." J. Biol. Chem. 274: 12642-12649.

Raya et al. (2000), "Goodpasture antigen-binding protein, the kinase that phosphorylates the goodpasture antigen, is an alternatively spliced variant implicated in autoimmune pathogenesis." J. Biol. Chem. 275: 40392-40399.

Revert et al. (1995), "Phosphorylation of the Goodpasture antigen by type A protein kinases." J. Biol. Chem. 270: 13254-13261.

Revert et al. (2007), "Increased Goodpasture antigen-binding protein expression induces type IV collagen disorganization and deposit of immunoglobulin A in glomerular basement membrane." Am. J. Pathol. 171: 1419-1430.

Revert et al. (2008), "Goodpasture antigen-binding protein is a soluble exportable protein that interacts with type IV collagen. Identification of novel membrane-bound isoforms." J. Biol. Chem. 283: 30246-55.

Rual et al. (2005), "Towards a proteome-scale map of the human protein-protein interaction network." Nature 437: 1173-1178.

Soccio and Breslow (2003), "StAR-related lipid transfer (START) proteins: mediators of intracellular lipid metabolism." J. Biol. Chem. 278: 22183-22186.

Strasser et al. (1991), "Enforced BCL2 expression in B-lymphoid cells prolongs antibody responses and elicits autoimmune disease." Proc. Natl. Acad. Sci. USA 88: 8661-8665.

Swanton et al. (2007), "Regulators of mitotic arrest and ceramide metabolism are determinants of sensitivity to paclitaxel and other chemotherapeutic drugs." Cancer Cell 11: 498-512.

Touriol et al. (2003), "Generation of protein isoform diversity by alternative initiation of translation at non-AUG condons." Biol. Cell. 95: 169-178.

Wyles et al. (2002), "Vesicle-associated membrane protein-associated protein-A (VAP-A) interacts with the oxysterol-binding protein to modify export from the endoplasmic reticulum." J. Biol. Chem. 277: 29908-29918.

Yang and Li (2005), "Roles of heat shock protein gp96 in the ER quality control: redundant or unique function?" Mol. Cells. 20: 173-182.

Yoshida et al. (2001), "XBP1 mRNA is induced by ATF6 and spliced by IRE1 in response to ER stress to produce a highly active transcription factor." Cell 107: 881-891.

A

```
MSDNQSWNSSGSEEDPETESGPPVERCGVLSKWTNYIHGWQDRWVVLKNNALSYYKSEDE    60
                        ←―1
TEYGCRGSICLSKAVITPHDFDECRFDISVNDSVWYLRAQDPDHRQQWIDAIEQHKTESG   120
  ←―2                                          ←―3
YGSESSLRRHGSMVSLVSGASGYSATSTSSFKKGHSLREKLAEMETFRDILCRQVDTLQK   180
                    ←―4
YFDACADAVSKDELQRDKVVEDDEDDFPTTRSDGDFLHSTNGNKEKLFPHVTPKGINGID   240
   ←―5                                     ←―6
FKGEAITFKATTAGILATLSHCIELMVKREDSWQKRLDKETEKKRRTEEAYKNAMTELKK   300
                      ←―7
KSHFGGPDYEEGPNSLINEEEFFDAVEAALDRQDKIEEQSQSEKVRLHWPTSLPSGDAFS   360
   ←―8
SVGTHRFVQKPYSRSSSMSSIDLVSASDDVHRFSSQVEEMVQNHMTYSLQDVGGDANWQL   420
                              ←―9
VVEEGEMKVYRREVEENGIVLDPLKATHAVKGVTGHEVCNYFWNVDVRNDWETTIENFHV   480
     ←―10                                        ←―11
VETLADNAIIIYQTHKRVWPASQRDVLYLSVIRKIPALTENDPETWIVCNFSVDHDSAPL   540
                     ←―12
NNRCVRAKINVAMICQTLVSPPECNQEISRDNILCKITYVANVNPGGWAPASVLRAVAKR   600
   ←―13
EYPKFLKRFTSYVQEKTAGKPILF                                      624
```

B

|   | |
|---|---|
| 7 | RRTEEAYKNAMTELKKKSHF³⁰⁴ Δ1 |
|   | GGPDYEEGPNSLINEEEFFD³²⁴ Δ2 |
| 8 | AVEAALDRQDKIEEQSQSEK³⁴⁴ Δ3 |
|   | VRLHWPTSLPSGDAFSSVGT³⁶⁴ Δ4 |

C

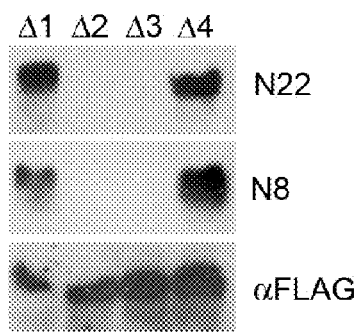

Figure 18

TAAAA*DGWKGRLPSPLVLLPRSARC*QARRRRGGRTSSLLLLPPTPERALFASPSPDPSPRGLGASSGAAE
GAGAGLLLGCRASMSDNQSWNSSGSEEDPETESGPPVERCGVLSKWTNYIHGWQDRWVVLKNNALSYYKS
EDETEYGCRGSICLSKAVITPHDFDECRFDISVNDSVWYLRAQDPDHRQQWIDAIEQHKTESGYGSESSL
RRHGSMVSLVSGASGYSATSTSSFKKGHSLREKLAEMETFRDILCRQVDTLQKYFDACADAVSKDELQRD
KVVEDDEDDFPTTRSDGDFLHSTNGNKEKLFPHVTPKGINGIDFKGEAITFKATTAGILATLSHCIELMV
KREDSWQKRLDKETEKKRRTEEAYKNAMTELKKKSHFGGPDYEEGPNSLINE*EEFFDAVE*AALDRQDKIE
EQSQSEKVRLHWPTSLPSGDAFSSVGTHRFVQKPYSRSSSMSSIDLVSAS*DDVHR*FSSQVEEMVQNHMTY
SLQDVGGDANWQLVVEEGEMKVYRREVEENGIVLDPLKATHAVKGVTGHEVCNYFWNVDVRNDWETTIEN
FHVVETLADNAIIIYQTHKRVWPASQRDVLYLSVIRKIPALTENDPETWIVCNFSVDHDSAPLNNRCVRA
KINVAMICQTLVSPPEGNQEISRDNILCKITYVANVNPGGWAPASVLRAVAKREYPKFLKRFTSYVQEKT
AGKPILF

GOODPASTURE ANTIGEN BINDING PROTEIN AND ITS DETECTION

CROSS REFERENCE

This application claims the benefit of U.S. Provisional Patent Application Ser. No. 61/082,741 filed Jul. 22, 2008 and 61/085,211 filed Jul. 31, 2008, both of which are incorporated by reference herein in their entirety.

BACKGROUND OF THE INVENTION

The conformation of the non-collagenous (NC1) domain of the α3 chain of the basement membrane collagen IV [α3 (IV)NC1] depends in part on phosphorylation. Goodpasture Antigen Binding Protein (GPBP) (WO 00/50607; WO 02/061430) is a novel non-conventional protein kinase that catalyzes the conformational isomerization of the α3(IV) NC1 domain during its supramolecular assembly, resulting in the production and stabilization of multiple α3(IV)NC1 conformers in basement membranes. Elevated levels of GPBP have been associated with the production of non-tolerized α3(IV)NC1 conformers, which conduct the autoimmune response mediating Goodpasture ("GP") disease. In GP patients, autoantibodies against the non-collagenous C-terminal domain (NC1) of the type IV collagen α3 chain ("Goodpasture antigen" or "GP antigen") cause a rapidly progressive glomerulonephritis and often lung hemorrhage, the two cardinal clinical manifestations of the GP syndrome.

The identification of GPBP provided methods for identification of compounds for the treatment of autoimmune disorders, cancer, protein misfolding-mediated disorders and aberrant apoptosis, and also provided potential therapeutics for these disorders. Thus, the identification of novel GPBP isoforms would be advantageous in at least these fields.

SUMMARY OF THE INVENTION

In a first aspect, the present invention provides isolated polypeptides of 90% or greater purity consisting of the amino acid sequence of SEQ ID NO: 2 (91 kD GPBP).

In a second aspect, the present invention provides substantially purified recombinant polypeptides comprising the general formula X-SEQ ID NO:2, wherein X is a detectable polypeptide. In one preferred embodiment of this aspect, the detectable polypeptide is selected from the group consisting of fluorescent polypeptides and polypeptide members of a binding pair. In another aspect, the present invention provides substantially purified nucleic acids encoding the polypeptides of this second aspect of the invention.

In a third aspect, the present invention provides substantially purified nucleic acids encoding a polypeptide consisting of the amino acid sequence of SEQ ID NO:2 (91 kD GPBP). In one preferred embodiment, the substantially purified nucleic acids consist of the nucleic acid of SEQ ID NO:1, or a mRNA product thereof.

In a fourth aspect, the present invention provides recombinant expression vectors comprising the substantially purified nucleic acid of any aspect of the invention.

In a fifth aspect, the present invention provides host cells transfected with a recombinant expression vector of the invention.

In a sixth aspect, the present invention provides a substantially purified polypeptide comprising the amino acid sequence of SEQ ID NO:2 (91 kD GPBP) or SEQ ID NO:4 (77 kD GPBP), wherein the polypeptide of SEQ ID NO:2 or SEQ ID NO:4 comprises one or more post-translational modifications (PTMs) directly and/or indirectly involving amino acids residues 305-344 GGPDYEEGPNSLINEEEFF-DAVEAALDRQDKIEEQSQSEK (SEQ ID NO: 10) (numbering based on position within 77 kD GPBP). In one preferred embodiment, the one or more PTMs comprise covalent PTMs. In another preferred embodiment, the one or more PTMs comprise covalent PTMs within amino acids 305-344 (SEQ ID NO: 10). In one preferred embodiment the one or more PTMs directly or indirectly involve residues 320-327 (EEFFDAVE, SEQ ID NO:5). In another preferred embodiment, the one or more PTMs comprise one or more covalent PTMs within residues 320-327 (EEFFDAVE, SEQ ID NO:5). In various preferred embodiments of this aspect, the substantially purified polypeptide comprises or consists of the amino acid sequence of SEQ ID NO:2 (91 kD GPBP) or SEQ ID NO:4 (77 kD GPBP).

In a seventh aspect, the present invention provides substantially purified polypeptides comprising the amino acid sequence of SEQ ID NO:2 (91 kD GPBP) or SEQ ID NO:4 (77 kD GPBP), wherein the polypeptide of SEQ ID NO:2 or SEQ ID NO:4 comprises one or more PTMs directly and/or indirectly involving residues 371-396, PYSRSSSMSSIDLVSASDDVHRFSSQ (SEQ ID NO:9) (numbering based on positions within 77 kD GPBP). In one preferred embodiment, the one or more PTMs comprise covalent PTMs. In another preferred embodiment, the one or more PTMs comprise covalent PTMs within amino acids 371-396 (SEQ ID NO:9). In one preferred embodiment, the one or more PTMs directly or indirectly involve residues 388-392 (DDVHR, SEQ ID NO:6). In another preferred embodiment, the one or more PTMs comprise one or more covalent PTMs within residues 388-392 (SEQ ID NO:6) In another preferred embodiment, the polypeptide further comprises one or more PTMs directly and/or indirectly involving amino acids residues 305-344 GGPDYEEGPNSLINEEEFFDAV-EAALDRQDKIEEQSQSEK (SEQ ID NO: 10) (numbering based on position within 77 kD GPBP); preferably the one or more PTMs comprise covalent PTMs, and even more preferably the one or more PTMs comprise covalent PTMs within amino acids 305-344 (SEQ ID NO: 10). In another preferred embodiment the one or more PTMs directly or indirectly involve residues 320-327 (EEFFDAVE, SEQ ID NO:5). In another preferred embodiment, the one or more PTMs comprise one or more covalent PTMs within residues 320-327 (EEFFDAVE, SEQ ID NO:5). In various preferred embodiments of this aspect, the substantially purified polypeptide comprises or consists of the amino acid sequence of SEQ ID NO:2 (91 kD GPBP) or SEQ ID NO:4 (77 kD GPBP).

In an eighth aspect, the present invention provides substantially purified monoclonal antibodies that selectively bind to a polypeptide of the sixth or seventh aspect of the invention.

In a ninth aspect, the present invention provides substantially purified monoclonal antibodies that specifically binds to the polypeptide of SEQ ID NO:2 and not to the polypeptide of SEQ ID NO:4. In one preferred embodiment, the monoclonal antibody binds to an epitope within the amino acid sequence DGWKGRLPSPLVLLPRSARC (SEQ ID NO:7)

In a tenth aspect, the present invention provides methods for detecting circulating Goodpasture antigen binding protein (GPBP), comprising
  (a) contacting a plasma sample with a GPBP-binding molecule under conditions to promote selective binding of the GPBP-binding molecule to the GPBP;
  (b) removing unbound GPBP-binding molecules; and
  (c) detecting complex formation between GPBP-binding molecule and the GPBP in the plasma sample.

In an eleventh aspect, the present invention provides methods for detecting urinary Goodpasture antigen binding protein (GPBP), comprising (a) contacting a urine sample with a GPBP-binding molecule under conditions to promote selective binding of the GPBP-binding molecule to the GPBP;

(b) removing unbound GPBP-binding molecules; and (c) detecting complex formation between GPBP-binding molecule and the GPBP in the urine sample.

In a twelfth aspect, the present invention provides methods for isolating native 77 kD GPBP, comprising:

(a) subjecting a plasma sample to ammonium sulfate precipitation;

(b) conducting ion-exchange chromatography (IEC) on the ammonium sulfate precipitated serum sample;

(c) identifying IEC fractions containing native 77 kD GPBP;

(d) subjecting IEC fractions containing native 77-GPBP to gel filtration chromatography (GFC); and (e) identifying GFC fractions containing native 77 kD GPBP.

In a thirteenth aspect, the present invention provides methods for isolating native 91 kD GPBP, comprising:

(a) subjecting a urine sample to salt precipitation;

(b) conducting double ion exchange chromatography (IEC) on the salt precipitated protein sample; and (c) identifying IEC fractions containing native 91 kD GPBP.

In a fourteenth aspect, the present invention provides methods for isolating native GPBP isoforms, comprising:

(a) passing a plasma sample or urine sample through an immunoaffinity column containing GPBP-binding molecules that selectively bind to native GPBP;

(b) washing unbound protein from the plasma or urine sample from the immunoaffinity column; and (c) eluting native GPBP isoforms from the column.

In one preferred embodiment, these methods can be used, for example, to substantially purify native 77 kD GPBP and native 91 kD GPBP from plasma and urine, respectively, as disclosed in more detail in the examples that follow. In another preferred embodiment, the GPBP-binding molecules comprise GPBP antibodies. In another preferred embodiment, the antibodies comprise the novel monoclonal antibodies of the present invention. In another preferred embodiment, the eluting step comprises use of a denaturing eluting buffer.

DESCRIPTION OF THE FIGURES

FIG. 18. Cloning of GPBP deletion mutants. In A, on the primary structure of GPBP (SEQ ID NO:4) we indicate the C terminus (bent arrows) of the thirteen 3' terminal FLAG-GPBP cDNA deletion mutants (1-13), obtained by standard PCR and recombinant DNA procedures. In B, is shown the sequence of GPBP encompassing the C-terminal regions of deletion mutants 7 (upper box) and 8 (lower box). In each lane, the number of the last residue is indicated. Δ1 is a FLAG-GPBP deletion mutant lacking residues 285-304 and similarly Δ2-Δ4 mutants lack residues 305-324, 325-344 and 345-364, respectively (SEQ ID NOS: 30-33). A peptide representing the bold sequence (SEQ ID NO:8) efficiently competed mAb 14 binding to GPBP and a GPBP mutant containing the sequence Ala Ala Val instead of the underlined residues failed to react with mAb 14. In C, protein extracts of HEK 293 cells transfected with individual pCDNA3-FLAG-GPBPΔ1 (Δ1)-pCDNA3-FLAG-GPBPΔ4 (Δ4), were analyzed by SDS-PAGE and Western blot with the indicated antibodies. Similar results were obtained for remaining antibodies included in the Table 1 under region 7-8: N4, N7, N9, N11, N14, N25, N27, N28 (similar to N22); and N2, N3, N5, N10, N12, N13 (similar to N8). The N16 antibody was not mapped.

FIG. 19 shows the sequence of 91 kD GPBP (SEQ ID NO:2).

DETAILED DESCRIPTION OF THE INVENTION

Figure 1:
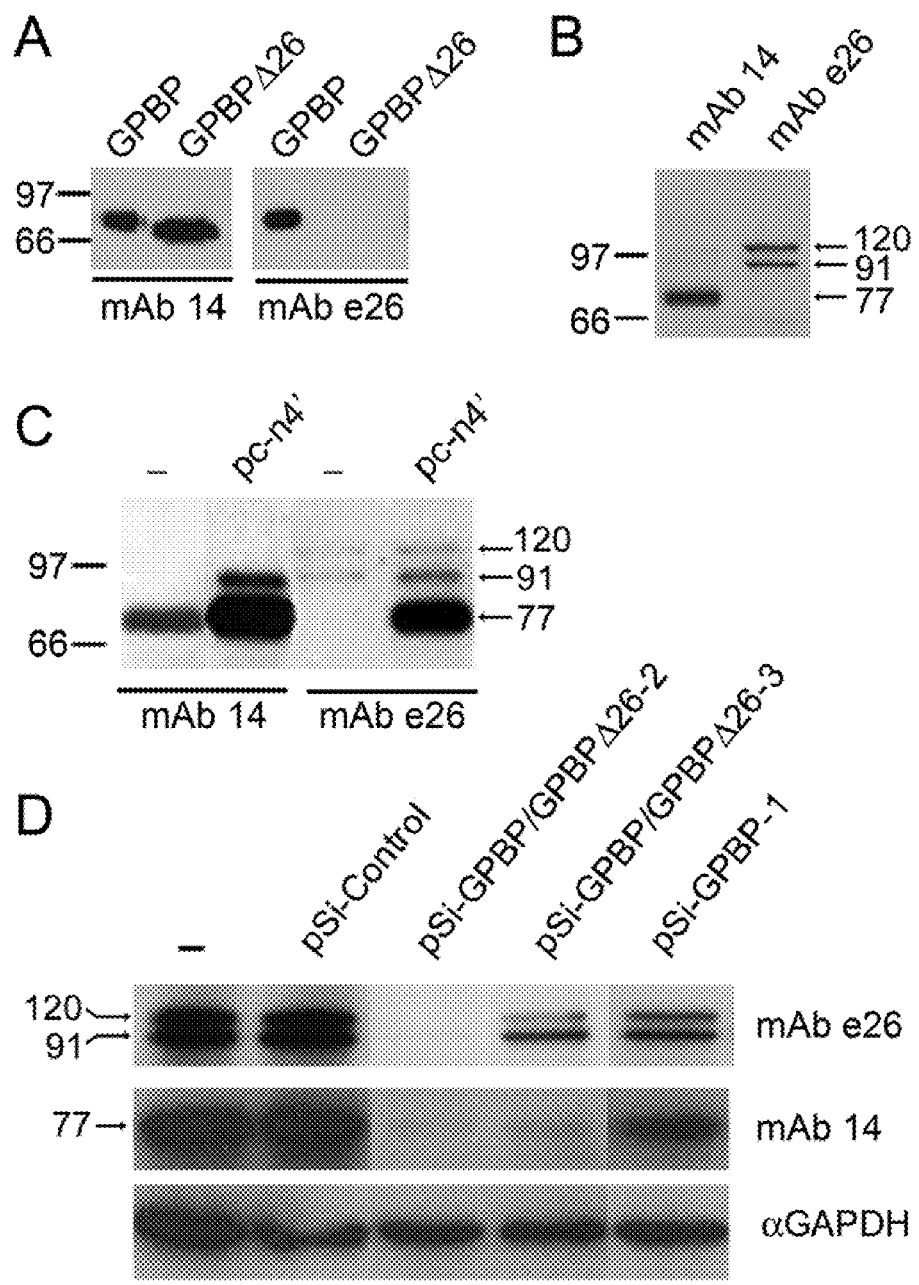
FIG. 1. COL4A3BP encodes for polypeptides of 77-, 91- and 120-kDa. In A, FLAG-tagged GPBP or GPBPΔ26/CERT (10-20 ng) were analyzed by Western blot with the indicated antibodies. In B, cell extracts (50 μg) were analyzed as in A. In C, extracts (10 μg) from control cells (–) or cells expressing pc-n4' were analyzed as in A. In D, extracts (50 μg) from untransfected cells (–) or from cells transfected with the indicated siRNA-expressing plasmid were analyzed as in A. Glyceraldehyde-3-phosphate dehydrogenase (GAPDH) was used as a loading control and siRNA specificity. The reactivity of mAb e26 with native or recombinant polypeptides was fully abolished when using GPBPpep 1 (20 μM) as antibody blocking peptide (not shown). In this and following Figures, numbers and bars or arrows indicate the size in kDa and the positions of the MW standards or the reactive polypeptides, respectively. The results shown in this and following Figures are representative of at least two independent experiments.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used in this application, the term "native protein" means the protein naturally produced by the cell, including any post-translational modifications (PTMs), and includes non-denatured protein, or denatured protein (as, for example, naturally produced protein substantially purified and subjected to one or more denaturing agents to, for example, run on a SDS-PAGE gel).

As used in this application, "substantially purified polypeptide" means that the polypeptide has been separated from its in vivo cellular environments. It is further preferred that the isolated polypeptides are also substantially free of gel agents, such as polyacrylamide, agarose, and chromatography reagents.

Unless clearly indicated otherwise by the context, embodiments disclosed for one aspect of the invention can be used in other aspects of the invention as well, and in combination with embodiments disclosed in other aspects of the invention.

In a first aspect, the present invention provides isolated polypeptides of 90% or greater purity consisting of the amino acid sequence of SEQ ID NO: 2 (91 kD GPBP). The inventors have determined that the hypothesized sequence of 91 kD GPBP previously proposed in WO 2004/070025 is incorrect, and have now isolated native 91 kD protein and determined its correct amino acid sequence, which is shown in SEQ ID NO:2. FIG. 19 shows the sequence of 91 kD GPBP, and in bold cursive underlined form, and from N to the C terminus, the amino acid residues comprising the epitopes of Ab 24, mAb 14 and mAb e26 respectively. The first residue (Met) of canonical 77-kDa GPBP (SEQ ID NO:4) is highlighted in bold and boxed in the figure. Thus, 91-kDa and 77-kDa GPBP are identical in amino acid sequence from the highlighted "Met" residue through the end of the protein. As noted below, the inventors have obtained compelling evidence that the mRNA of GPBP undergoes canonical (AUG) and noncanonical (ACG) translation initiation to generate two primary polypeptides of 77- and 91-kDa, respectively. The results from this study also support that both products enter the secretory pathway. However, whereas the 77-kDa reaches the extracellular compartment and exists in a soluble immuno-precipitable form, the 91-kDa remains mainly insoluble, associated with cellular membranes and likely reaches the external side of plasma membrane. The evidence supports that the 120-kDa GPBP isoform is a covalently-derived product of the 91-kDa GPBP (ie: the only differences are post-translational modifications) and thus shares the amino acid sequence of 91-kDa polypeptide. Therefore, as used herein, the term "91-kDa GPBP" includes the 91-kDa and post translational modifications thereof, including but not limited to 120-kDa GPBP and aggregates of 91-kDa and 120-kDa GPBP. The present invention provides additional evidence for the 91-kDa GPBP to exist in a soluble form in the plasma and urine revealing that the 91-kDa GPBP can be released from the cellular membranes. The polypeptides of this aspect of the invention can be used, for example, to produce antibodies against 91-kDa GPBP, and as targets for identification of compounds that interfere with GPBP activity, making them useful therapeutics for various disorders, including Goodpasture Syndrome.

Thus, our data support the notion that mRNA alternative translation initiation is a strategy to direct GPBP to multiple locations including secretory pathway, plasma membrane and extracellular compartment.

In this aspect and the other polypeptide aspects and embodiments of the invention, the polypeptides can be used, for example, to generate specific antibodies for detection of different isoforms of native GPBP present in serum or in urine, which can thus be used as, for example, diagnostic agents for autoimmune and other disorders. The polypeptides of the invention can also be used, for example, as tools to identify candidate compounds for inhibiting various specific types of native GPBP isoforms and also to identify candidate compounds for treating, for example, autoimmunity and protein misfolding-mediated disorders, as discussed in more detail below.

As used herein, "90% or greater purity" means that contaminating proteins make up no more than 10% of the isolated polypeptide; in various preferred embodiments, no more than 9%, 8%, 7%, 6%, 5%, 4%, 3%, 2%, 1%, or 0.5% of the isolated polypeptide (e.g., isolated polypeptides of 91%, 92%, 93%, 94%, 95%, 96%, 97%, 98%, 99%, or 99.5% or greater purity consisting of the amino acid sequence of SEQ ID NO: 2). It is further preferred that the isolated polypeptides are also substantially free of gel agents, such as polyacrylamide and agarose. In a further preferred embodiment, the isolated polypeptides are present in solution, frozen, or as a dried powder. In one preferred embodiment, the isolated polypeptides of this first aspect are optionally labeled with a detectable, non-polypeptide label, including but not limited to fluorescent labels or radioactive labels.

In a second aspect, the present invention provides substantially purified recombinant polypeptides comprising or consisting of the general formula X-SEQ ID NO:2, wherein X is a detectable polypeptide. In this aspect, the correct amino acid sequence for 91 kD GPBP (SEQ ID NO:2) is expressed as a fusion protein with a detectable polypeptide. The polypeptides of this aspect of the invention can be used, for example, to track 91 kD GPBP in cells, and as a detectable target for identification of compounds that interfere with GPBP activity, making them useful therapeutics for various disorders, including Goodpasture Syndrome. As used in this aspect, a "recombinant polypeptide" means that the detectable polypeptide is not derived from GPBP or expressed from a GPBP mRNA, and thus fuses a heterologous detectable peptide with the correct 91 kD GPBP polypeptide. As used herein, a "detectable polypeptide" is any heterologous peptide that can be detected, thus permitting detection of the recombinant polypeptide. In one preferred embodiment, the detectable polypeptide comprises a fluorescent protein. Any fluorescent protein known in the art can be used in the invention. For example, green fluorescent proteins of cnidarians, which act as their energy-transfer acceptors in bioluminescence, are suitable fluorescent proteins for use in the fluorescent indicators. A green fluorescent protein ("GFP") is a protein that emits green light, and a blue fluorescent protein ("BFP") is a protein that emits blue light. GFPs have been isolated from the Pacific Northwest jellyfish, *Aequorea victoria*, the sea pansy, *Renilla reniformis*, and *Phialidium gregarium*. See, Ward, W. W., et al., Photochem. Photobiol., 35:803 808 (1982); and Levine, L. D., et al., Comp. Biochem. Physiol., 72B:77 85 (1982). A variety of *Aequorea*-related GFPs having useful excitation and emission spectra have been engineered by modifying the amino acid sequence of a naturally occurring GFP from *Aequorea victoria*. See, Prasher, D. C., et al., Gene, 111:229 233 (1992); Heim, R., et al., Proc. Natl. Acad. Sci., USA, 91:12501 04 (1994); U.S. Ser. No. 08/337,915, filed Nov. 10, 1994; International application PCT/US95/14692, filed Nov. 10, 1995; and U.S. Ser. No. 08/706,408, filed Aug. 30, 1996. The cDNA of GFP can be concatenated with those encoding many other proteins; the resulting fusions generally are fluorescent and retain the biochemical features of the partner proteins. See, Cubitt, A. B., et al., Trends Biochem. Sci. 20:448 455 (1995). Mutagenesis studies have produced GFP mutants with shifted wavelengths of excitation or emission. See, Heim, R. & Tsien, R. Y. Current Biol. 6:178 182 (1996). Suitable pairs, for example a blue-shifted GFP mutant P4-3 (Y66H Y145F) and an improved green mutant S65T can respectively serve as a donor and an acceptor for fluorescence resonance energy transfer (FRET). See, Tsien, R. Y., et al., Trends Cell Biol. 3:242 245 (1993).

In another preferred embodiment of this second aspect, the detectable polypeptide comprises a non-GPBP epitope for which antibodies are commercially available, including but not limited to the FLAG (Sigma Chemical, St. Louis, Mo.), myc (9E10) (Invitrogen, Carlsbad, Calif.), 6-His (Invitrogen; Novagen, Madison, Wis.), glutathione S-transferase (GST) (Santa Cruz Biotechnology, Santa Cruz, Calif.), and HA (hemaglutinin) (Boehringer Manheim Biochemicals).

In all of the embodiments of the second aspect of the invention, the isolated polypeptide may preferably further comprise a linker sequence between the detectable polypeptide and the polypeptide of SEQ ID NO:2. In this embodiment, the linker is not a portion of GPBP or encoded by a GPBP mRNA. Such a linker can be of any desirable length, and preferably is between 1 and 20 amino acids, if present; more preferably between 1 and 15, 1-10, 1-5, 1-4, 1-3, or 1-2 amino acids, if present. The linker can be used, for example, to optimally position the detectable polypeptide and the 91 kD GPBP sequence and to include specific sequence for protease recognition site to allow removal of detectable polypeptide. In all of the embodiments of the second aspect of the invention, the isolated polypeptide may further comprise any additional residues necessary for expression, such as an N-terminal methionine residue or peptide sequences to deliver the polypeptide to different cellular and extracellular compartments.

The substantially purified polypeptides of the invention can be made by any method known to those of skill in the art, but are preferably made by recombinant means based on the teachings provided herein. For example, a coding region of interest as disclosed herein can be cloned into a recombinant expression vector, which can then be used to transfect a host cell for recombinant protein production by the host cells.

In a third aspect, the present invention provides substantially purified nucleic acids encoding a polypeptide consisting of the amino acid sequence of SEQ ID NO:2 (91 kD GPBP). The substantially purified nucleic acid sequence may comprise RNA or DNA. As used herein, "substantially purified nucleic acids" are those that have been removed from their normal surrounding nucleic acid sequences in the genome or in cDNA sequences. Such substantially purified nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. In one preferred embodiment, the substantially purified nucleic acid coding region consists of the nucleic acid of SEQ ID NO:1, or a mRNA product thereof. In another preferred embodiment, the present invention provides substantially purified nucleic acids encoding the polypeptide of any embodiment of the substantially purified recombinant polypeptides comprising or consisting of the general formula X-SEQ ID NO:2, as discussed in the second aspect of the invention.

In a fourth aspect, the present invention provides recombinant expression vectors comprising the substantially purified nucleic acid of any aspect of the invention operatively linked to a promoter. "Recombinant expression vector" includes vectors that operatively link a nucleic acid coding region or gene to any promoter capable of effecting expression of the gene product. The promoter sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a fifth aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, 2$^{nd}$ Ed. (R. I. Freshney. 1987. Liss, Inc. New York, N.Y.).

In a sixth aspect, the present invention provides a substantially purified polypeptide comprising the amino acid sequence of SEQ ID NO:2 (91 kD GPBP) or SEQ ID NO:4 (77 kD GPBP), wherein the polypeptide of SEQ ID NO:2 or SEQ ID NO:4 comprises one or more post-translational modifications (PTMs) directly and/or indirectly involving amino acids residues 305-344 GGPDYEEGPNSLINEEEFF-DAVEAALDRQDKIEEQSQSEK (SEQ ID NO: 10) (numbering based on position within 77 kD GPBP). As disclosed in the examples that follow, the inventors provide the first purification of native 77 and 91 kD GPBP and have determined that existing monoclonal antibodies that bind to recombinant versions of 77 kD- and 91 kD-GPBP do not bind to purified native versions, verifying that structural differences exist between recombinant and native forms of the 77 kD GPBP and between recombinant and native forms of the 91 kD GPBP. The polypeptides of this aspect of the invention can be used, for example, to produce antibodies against native GPBP forms, and as targets for identification of compounds that interfere with native GPBP activity, making them useful therapeutics for various disorders, including Goodpasture Syndrome. In one preferred embodiment, the one or more PTMs comprise covalent PTMs. In another preferred embodiment, the one or more PTMs comprise covalent PTMs within amino acids 305-344 (SEQ ID NO: 10). In one preferred embodiment the one or more PTMs directly or indirectly involve residues 320-327 (EEFFDAVE, SEQ ID NO:5). In another preferred embodiment, the one or more PTMs comprise covalent PTMs within residues 320-327 (EEFFDAVE, SEQ ID NO:5) (numbering based on position within 77 kD GPBP). In another preferred embodiment, the one or more PTMs comprise one more PTMs present in residue 320, 321, and/or 327; most preferably, the one or more PTMs present at these residues comprise covalent PTMs. In a further preferred embodiment of any of the embodiments of this aspect, the substantially purified polypeptide possesses an amino acid sequence consisting of SEQ ID NO:2 (91 kD GPBP) or SEQ ID NO:4 (77 kD GPBP).

As used herein, the term "post-translational modification" (PTM) means a modification in the structure of a protein after its translation. In one preferred embodiment, the PTM comprises addition of a functional group, including but not limited to carboxylation, methylation, citrullination, phosphorylation, glycosylation, and formation of atypical isoaspartyl. In another preferred embodiment, the PTM comprises an isomerization, leading to a conformational change.

As used herein, "directly" means that the PTM occurs within the specified residues, while "indirectly" means that the PTM occurs outside the specified residues, but results in a structural change within the cited residues.

Any suitable method for making the covalently modified polypeptide of SEQ ID NO:2 or SEQ ID NO:4 based on the teachings of the present disclosure can be used, including isolating from natural sources of GPBP as disclosed herein, and recombinant production of GPBP followed by suitable covalent modification within the relevant region of amino acid residues, using standard methods known to those of skill in the art.

In a seventh aspect, the present invention provides substantially purified polypeptides comprising the amino acid sequence of SEQ ID NO:2 (91 kD GPBP) or SEQ ID NO:4 (77 kD GPBP), wherein the polypeptide of SEQ ID NO:2 or SEQ ID NO:4 comprises one or more PTMs directly and/or indirectly involving residues 371-396

PYSRSSSMSSIDLVSASDDVHRFSSQ (SEQ ID NO:9) (numbering based on positions within 77 kD GPBP). As disclosed in the examples that follow, the inventors provide the first purification of native 77 kD and 91 kD GPBP and have determined that existing monoclonal antibodies that bind to recombinant version of 77 kD and 91 kD GPBP do not bind to the purified native 77 kD and 91 kD GPBP versions, verifying that structural differences exist between recombinant and native forms of the 77 and 91 kD GPBP. The polypeptides of this aspect of the invention can be used, for example, to produce antibodies against native GPBP, and as targets for identification of compounds that interfere with native GPBP activity, making them useful therapeutics for various disorders, including Goodpasture Syndrome. In one preferred embodiment, the one or more PTMs comprise covalent PTMs. In another preferred embodiment, the one or more PTMs comprise covalent PTMs within amino acids 371-396 (SEQ ID NO:9). In one preferred embodiment, the one or more PTMs directly or indirectly involve residues 388-392 (DDVHR, SEQ ID NO:6). In another preferred embodiment, the one or more PTMs comprise one or more covalent PTMs within residues 388-392 (SEQ ID NO:6) In another preferred embodiment, the polypeptide further comprises one or more PTMs directly or indirectly involving residues 320-327 (EEFFDAVE, SEQ ID NO:5) In a further preferred embodiment, the one or more PTMs within residues 320-327 are covalent PTMs. In various preferred embodiments of this aspect, the substantially purified polypeptide possesses an amino acid sequence consisting of SEQ ID NO:2 (91 kD GPBP) or SEQ ID NO:4 (77 kD GPBP). Any suitable method for making the covalently modified polypeptide of SEQ ID NO:2 or SEQ ID NO:4 can be used, including isolating from natural sources of GPBP as disclosed herein, and recombinant production of GPBP followed by suitable covalent modification within the relevant region of amino acid residues, using standard methods known to those of skill in the art.

In an eighth aspect, the present invention provides substantially purified monoclonal antibodies that selectively bind to the substantially purified polypeptides of the sixth or seventh aspect of the invention. As disclosed above, the inventors have for the first time isolated native 77- and 91 kD GPBP species that when substantially purified do not bind to existing GPBP-specific monoclonal antibodies. For example, existing monoclonal antibodies do not detect GPBP in plasma or urine samples in ELISAs, nor are they capable of use for purification of plasma or urine GPBP. Thus, the monoclonal antibodies of the invention are useful, for example, in ELISA-based assays for GPBP detection in urine or plasma, and for purification of GPBP from plasma or serum. The inventors further demonstrate herein that these native 77 kD GPBP and native 91 kD GPBP species are pos-translationally modified, and that at least some of these PTMs render substantially purified, native GPBP non-reactive to existing monoclonal GPBP antibodies. Exemplary monoclonal antibodies according to this aspect of the invention are provided in the examples that follow.

The "monoclonal antibodies" of the invention can be any type of monoclonal antibody, including but not limited to standard monoclonal antibodies, humanized monoclonals, chimeric monoclonals, and fragments thereof.

As used herein, "substantially purified" means that the recited monoclonal antibodies make up at least 80% of the antibodies in a substantially purified sample; more preferable at least 85%, 90%, 91%, 92%, 93%, 94%, 95%, 96%, 97%, 98%, 99%, or more.

As used herein, "selectively bind" means preferential binding of the GPBP monoclonal antibody to native GPBP epitope, as opposed to one or more other biological molecules, structures, cells, tissues, etc., as is well understood by those of skill in the art.

Monoclonal antibodies can be produced by obtaining spleen cells from the animal [See Kohler and Milstein, Nature 256, 495-497 (1975)]. In one example, monoclonal antibodies (mAb) of interest are prepared by immunizing inbred mice with native 77 kD GPBP, native 91 kD GBPB, or an antigenic fragment thereof, including, but not limited to, one or more epitopes comprising or consisting of the PTM-containing peptides EEFFDAVE (SEQ ID NO:5), DDVHR (SEQ ID NO:6), LINEEEFFDAVEAALDRQ (SEQ ID NO:8), PYSRSSSMSSIDLVSASDDVHRFSSQ (SEQ ID NO:9), and GGPDYEEGPNSLINEEEFFDAV-EAALDRQDKIEEQSQSEK (SEQ ID NO: 10). Thus, in a further preferred embodiment, the monoclonal antibodies bind one or more epitopes comprising one or more PTMs, selected from the group consisting of PTM-containing EEF-FDAVE (SEQ ID NO:5), DDVHR (SEQ ID NO:6), LINEE-EFFDAVEAALDRQ (SEQ ID NO:8), PYSRSSSMSSIDLVSASDDVHRFSSQ (SEQ ID NO:9), and GGPDYEEGPNSLINEEEFFDAV-EAALDRQDKIEEQSQSEK (SEQ ID NO: 10). In a further preferred embodiment, the one or more PTMs are covalent PTMs. In another preferred embodiment, the monoclonal antibodies bind to an epitope that comprises one or more PTMs (preferably covalent PTMs) present in residue 320, 321, and/or 327 (numbering based on 77 kD GPBP).

In one exemplary embodiment, the mice are immunized by the IP or SC route in an amount and at intervals sufficient to elicit an immune response. The mice receive an initial immunization on day 0 and are rested for about 3 to about 30 weeks. Immunized mice are given one or more booster immunizations of by the intravenous (IV) route. Lymphocytes, from antibody positive mice are obtained by removing spleens from immunized mice by standard procedures known in the art. Hybridoma cells are produced by mixing the splenic lymphocytes with an appropriate fusion partner under conditions which will allow the formation of stable hybridomas. The antibody producing cells and fusion partner cells are fused in polyethylene glycol at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells and are screened for antibody production by an immunoassay such as solid phase immunoradioassay. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

"Humanized monoclonal antibodies" refers to monoclonal antibodies derived from a non-human monoclonal antibody, such as a mouse monoclonal antibody. Alternatively, humanized monoclonal antibodies can be derived from chimeric antibodies that retains, or substantially retains, the antigen-binding properties of the parental, non-human, monoclonal antibodies but which exhibits diminished immunogenicity as compared to the parental monoclonal antibody when administered to humans. For example, chimeric monoclonal antibodies can comprise human and murine antibody fragments, generally human constant and mouse variable regions. Humanized monoclonal antibodies can be prepared using a variety of methods known in the art, including but not limited to (1) grafting complementarity determining regions from a non-human monoclonal antibody onto a human framework and constant region ("humanizing"), and (2) transplanting the non-human monoclonal antibody variable domains, but "cloaking" them with a human-like surface by replacement of surface residues ("veneering"). These methods are disclosed, for example, in, e.g., Jones et al., Nature 321:522-525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991).

Monoclonal antibodies can be fragmented using conventional techniques, and the fragments screened for utility in the same manner as for whole antibodies. For example, F(ab')$_2$ fragments can be generated by treating antibody with pepsin. The resulting F(ab')$_2$ fragment can be treated to reduce disulfide bridges to produce Fab' fragments. Fab fragments can be obtained by treating an IgG antibody with papain; F(ab') fragments can be obtained with pepsin digestion of IgG antibody. A F(ab') fragment also can be produced by binding Fab' described below via a thioether bond or a disulfide bond. A Fab' fragment is an antibody fragment obtained by cutting a disulfide bond of the hinge region of the F(ab')2. A Fab' fragment can be obtained by treating a F(ab')2 fragment with a reducing agent, such as dithiothreitol. Antibody fragment peptides can also be generated by expression of nucleic acids encoding such peptides in recombinant cells (see, e.g., Evans et al., J. Immunol. Meth. 184: 123-38 (1995)). For example, a chimeric gene encoding a portion of a F(ab')2 fragment can include DNA sequences encoding the CH1 domain and hinge region of the H chain, followed by a translational stop codon to yield such a truncated antibody fragment molecule.

Examples of monoclonal antibody fragments include (i) a Fab fragment, a monovalent fragment consisting essentially of the VL, VH, CL and CH I domains; (ii) F(ab)2 and F(ab')2 fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., (1989) Nature 341:544-546), which consists essentially of a VH domain; and (vi) one or more isolated CDRs or a functional paratope.

To generate an antibody response, the immunogens are typically formulated with a pharmaceutically acceptable carrier for parenteral administration. Such acceptable adjuvants include, but are not limited to, Freund's complete, Freund's incomplete, alum-precipitate, water in oil emulsion containing *Corynebacterium parvum* and tRNA. The formulation of such compositions, including the concentration of the polypeptide and the selection of the vehicle and other components, is within the skill of the art.

In a ninth aspect, the present invention provides substantially purified monoclonal antibodies that specifically binds to the polypeptide of SEQ ID NO:2 and not to the polypeptide of SEQ ID NO:4. Such monoclonal antibodies of the invention are useful, for example, in distinguishing 91 kD GPBP from 77 kD GPBP in assays including, but not limited to, ELISA-based assays for GPBP detection in urine or plasma. Such monoclonal antibodies can be generated using methods disclosed above and the use of peptide immunogens present in the polypeptide of SEQ ID NO:2 but not present in SEQ ID NO:4. Such immunogens may be of any suitable length to generate an antibody response. In one exemplary embodiment, the monoclonal antibodies are generate against an immunogen comprising or consisting of DGWKGRLPSPLV-LLPRSARC (SEQ ID NO:7). Thus, in this embodiment, the monoclonal antibody binds to an epitope within the amino acid sequence DGWKGRLPSPLVLLPRSARC (SEQ ID NO:7). An exemplary such antibody, Ab24, is disclosed below.

In a further aspect, the present invention provides isolated hybridoma cells expressing the monoclonal antibodies of the eighth or ninth aspects of the invention.

The invention also provides methods for making the antibodies of the invention, as disclosed above and below.

In a tenth aspect, the present invention provides methods for detecting circulating Goodpasture antigen-binding protein (GPBP), comprising (a) contacting a plasma sample with a GPBP-binding molecule that binds to GPBP under conditions to promote selective binding of the GPBP-binding molecule to the GPBP;

(b) removing unbound GPBP-binding molecules; and (c) detecting complex formation between the GPBP-binding molecule and the GPBP in the plasma sample.

A "plasma sample" means blood plasma, the liquid component of blood, and is prepared, for example, by centrifugation of whole blood to remove blood cells. As used herein, a plasma sample also includes a blood serum sample, in which blood clotting factors have been removed.

In an eleventh aspect, the present invention provides methods for detecting urinary Goodpasture antigen-binding protein (GPBP), comprising (a) contacting a urine sample with a GPBP-binding molecule that binds to GPBP under conditions to promote selective binding of the GPBP-binding molecule to GPBP;

(b) removing unbound GPBP-binding molecule; and (c) detecting complex formation between the GPBP-binding molecule and the GPBP in the urine sample.

Urine samples are easily obtained, and analyte determination in urine is well known in the art.

A "GPBP-binding molecule" is a peptide or nucleic acid molecule that binds selectively to GPBP, as opposed to one or more other biological molecules, structures, cells, tissues, etc. Exemplary embodiments of such GPBP-binding molecules include but are not limited to antibodies, aptamers or substrates. As used herein, a "GPBP substrate" is a target of GPBP biological activity that binds to GPBP, or a fragment thereof that retains GPBP-binding activity. Such GPBP substrates include, but are not limited to, 1-20 (SEQ ID NO: 16), GPBP-interacting proteins (GIPs) (SEQ ID NOS: 17-21), myelin basic protein (MBP) and derivatives thereof (SEQ ID NOS:22-25), prion protein (PrP) (SEQ ID NO:26), type IV collagen α3 chain NC1 domain (α3(IV)NC1) (SEQ ID NO:27), and Alzheimer's disease beta peptide (Aβ$_{1-42}$) (SEQ ID NO:28). Exemplary references demonstrating GPBP binding of these substrates can be found in U.S. Pat. Nos. 6,579,969; 7,147,855; and 7,326,768, incorporated by reference herein in their entirety.

As disclosed in the examples that follow, the inventors have discovered circulating and urinary forms of GPBP, including GPBP isoforms of 160-, 91-, 77-, 70-, 66-, 60-, 58-, 56- 53- 50- 46- 35 and 34-kD, and various aggregates thereof Thus, in the tenth and eleventh aspects, the term "GPBP" refers to all GPBP isoforms reactive with GPBP-selective antibodies, including but not limited to 77 kD GPBP and 91 kD GPBP, as well lower and higher molecular weight GPBP isoforms of 160-, 60-, 58-, 56- 53- 50- 46- 35 and 34-kD, and aggregates thereof.

The "plasma sample" or "urine sample" may be obtained from any suitable subject, preferably from a mammal, including but not limited to a human, dog, cat, horse, or livestock (cow, sheep, etc.). In a most preferred embodiment, the plasma sample or urine sample is obtained from a human subject, such as a human subject suspected of having an autoimmune condition including but not limited to Goodpasture Syndrome and/or immune-complex mediated glomerulonephritis. As disclosed herein, the inventors have isolated native circulating 77 kD GPBP from human plasma and have observed increased levels in Goodpasture patients and in animal models for immune complex-mediated glomerulonephritis, demonstrating that GPBP secretion occurs in vivo and revealing the clinical utility of serological and urinary determination of GPBP.

The antibody can be any selective GPBP antibody, whether polyclonal, monoclonal, or humanized monoclonal as described above, although monoclonal antibodies are preferred. In one embodiment, antibodies according to the eighth or ninth aspects of the invention are used. The methods of the tenth and eleventh aspect of the invention may comprise analyzing a specific GPBP isoform, such as 77 kD GPBP or 91 kD GPBP; in these embodiments, antibodies selective for 77 kD GPBP or selective for 91 kD GPBP can be used, including but not limited to those selective antibodies disclosed herein. In a most preferred embodiment, the antibodies for use in the methods of the tenth and eleventh aspects of the invention are those that bind to native GPBP isoforms, such as those disclosed herein.

Conditions suitable to promote binding of GPBP-binding molecules, such as antibodies, aptamers or substrates, to GPBP in the plasma or urine samples can be determined by those of skill in the art based on the teachings herein and the examples provided below. For example, antibody-antigen binding often depends on hydrophobic interactions (the so called hydrophobic bonds); thus, high salt concentrations, such as in the molar range can be used to reduce nonspecific binding and increase specific antigen-antibody binding. Optionally, further steps may be included to promote selectivity and specificity, including but not limited to one or more wash steps to remove unbound or weakly bound serum proteins; inhibitors of non-specific binding to reduce binding of high concentration serum proteins, control samples known to contain GPBP isoforms and/or negative controls known not to bind to GPBP isoforms, and/or inclusion of serum or urine samples known to not possess GPBP (ex: deleted for GPBP).

These tenth and eleventh aspects of the present invention may be used to test for the presence of GPBP in the plasma or urine sample by standard techniques including, but not limited to ELISA, immunofluorescence, and chromatography (for example, lateral flow assays where the antibody is immobilized on a surface and plasma or urinary proteins are labeled and allowed to flow over the surface under conditions suitable to permit binding of the antibody to GPBP in the plasma or urine). In one embodiment, functional beads (Becton Dickinson technology) coupled to flow cytometry are used; this technique is an emerging method to measure the levels of proteins in biological fluid or cell/tissue extracts. Specifically, beads made of a fluorescence matrix are coated with one or more specific GPBP antibodies, mixed with the plasma sample and further incubated with a detecting antibody labeled with a phycoerythrins. Finally, beads are analyzed by a flow cytometry program which selects the beads according matrix fluorescence emission and measurement of the level of the analyte through phycoerythrin emission. There are up to thirty different types of beads that can be simultaneously detected and discriminated by the cytometer. This method couples high sensitivity and performance with versatility since a specific bead type coated with GPBP antibody can be mixed with a distinct bead type coated with binding peptides for other analyte (i.e. autoantibodies) and simultaneously measured. The measurement of various analytes could enhance the potential of GPBP determination. In one embodiment, the techniques may determine only the presence or absence of the GPBP isoform(s). Alternatively, the techniques may be quantitative, and provide information about the relative amount of the protein or peptide of interest in the sample. For quantitative purposes, ELISAs are preferred.

Detection of immunocomplex formation can be accomplished by standard detection techniques. For example, detection of immunocomplexes can be accomplished by using labeled antibodies or secondary antibodies. Such methods, including the choice of label are known to those ordinarily skilled in the art. (Harlow and Lane, Supra). Alternatively, the antibodies can be coupled to a detectable substance. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase. Examples of suitable prosthetic-group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of suitable radioactive material include $^{125}I$, $^{131}I$, $^{35}S$ or $^{3}H$.

As noted above, the inventors have observed increased levels in Goodpasture patients and in animal models for immune complex-mediated glomerulonephritis, demonstrating that GPBP secretion occurs in vivo and revealing the clinical utility of serological determination of GPBP. Thus, the methods of this aspect of the invention can be used, for example, to detect GPBP-mediated disorder in a subject, including but not limited to an antibody-mediated disorder (including but not limited to a glomerulonephritis selected from the group consisting of IgA nephropathy, systemic lupus erythematosus and Goodpasture disease), inflammation, an ER-stress mediated disorder, and drug-resistant cancer. In these embodiments, the methods would comprise comparison of GPBP levels detected in a test serum or urine sample with a control, such as a control from a serum or urine sample known to have "normal" levels of GPBP or previously determined normal values for GPBP in sera or urine from the subject from whom the serum is obtained. In various embodiments, the control provides a standard curve using recombinant GPBP or a reference value. In comparing the amount of GPBP in the serum or urine sample to a control, an increase (preferably a statistically significant increase using standard statistical analysis techniques) in GPBP in the serum or urine sample relative to the control indicates the presence of one or more of the disorders noted above, or an increased risk of developing one or more of the disorders, all of which are correlated with increased GPBP expression.

It has previously been disclosed that increased GPBP expression induces IgA nephropathy, immune complex-related glomerulonephritis; that increased GPBP expression is intimately involved in Goodpasture Syndrome pathogenesis; and that increased GPBP expression mediates resistance of cancer cells to chemotherapeutic agents that induce protein misfolding and ER stress-mediated cell death. The methods of the present invention thus provide methods for diagnosing these disorders by serological or urine testing for the presence of GPBP. Thus, the methods identify individuals either having or at risk of being stricken with one or more of an antibody-mediated disorder (including but not limited to a glomerulonephritis selected from the group consisting of IgA nephropathy, systemic lupus erythematosus and Goodpasture disease), inflammation, an ER-stress mediated disorder, and drug-resistant cancer. In one non-limiting embodiment, the methods can be used to test cancer patients either prior to or after initiation of a chemotherapy regimen; those patients that test positive for increased serum levels of GPBP are at increased risk of having a drug-resistant tumor or of their tumor is developing drug-resistance, and an attending physician can assess appropriate treatment options in light thereof Furthermore, such patients may undergo periodic testing for serum or urine levels of GPBP to monitor potential risk of developing a drug-resistant tumor. Similarly, patients thought to be at risk for developing, or suspected of already having developed a glomerulonephritis selected from the group consisting of IgA nephropathy, systemic lupus erythematosus and Goodpasture disease, can be tested for serum or urine levels of GPBP. Further embodiments will be clear to those of skill in the art based on the teachings herein.

GPBP is a circulating molecule and GBM (glomerular basement membrane) a principal component of the glomerular filtration barrier; therefore, GPBP accumulation in the glomerulus could result from local production but also from the sequestration of circulating GPBP produced elsewhere, and could also be reflected in increased GPBP in the urine. The local overproduction could account for primary antibody-mediated glomerulonephritis whereas increased circulating levels may induce secondary forms of this pathology and perhaps are responsible for disease recurrence upon renal transplantation. Consequently, in another embodiment, quantification of the levels of circulating or urinary GPBP is useful in discriminating primary from secondary antibody-mediated glomerulonephritis and for the clinical monitoring of renal transplantation.

In a further embodiment, combining GPBP determination with analysis of other analytes the methods permit one to perform differential diagnosis or prognosis in the above disorders. In one non-limiting example, we have found that some IgA nephropathy patients produce anti-basement membrane autoantibodies. These circulating autoantibodies recognize the NC1 domain of type IV collagen. Determination of the titer of these antibodies could help to monitor disease progression or also to distinguish different IgA nephropathy patients or to perform prognosis in these patients. By measuring anti-ssDNA, anti-nucleosome autoantibodies and GPBP levels one can diagnose systemic lupus erythematosus but also distinguish between primary IgA nephropathy and IgA nephropathy secondary to systemic lupus erythematosus. In various further embodiments, any determination used to diagnosis of primary diseases listed in Donadio and Grande (2002) N Engl J Med 347, 738-748 associated with glomerular deposition of IgA, can be used in conjunction with the methods of the invention for plasma or urinary detection of GPBP for differential diagnosis in secondary IgA nephropathy patients.

In another embodiment, a normal value of GPBP as a reference for an standard curve is between ~1 ng/ml-10 ng/ml in plasma and approximately 0.2 ng/ml to 1.5 ng/ml in urine, while Goodpasture patients exceed the normal by at least 2-fold; in other embodiments, by at least 3-fold, 4-fold, 5-fold, 6-fold, 7-fold, 8-fold, or more the normal values.

In a twelfth aspect, the present invention provides methods for isolating native GPBP isoforms, comprising:
(a) subjecting a plasma sample to ammonium sulfate precipitation;
(b) conducting ion-exchange chromatography (IEC) on the ammonium sulfate precipitated serum sample;
(c) identifying IEC fractions containing native GPBP isoforms;
(d) subjecting IEC fractions containing native GPBP isoforms to gel filtration chromatography (GFC); and
(e) identifying GFC fractions containing native GPBP isoforms.

In one preferred embodiment, these methods can be used, for example, to substantially purify native 77 kD GPBP from plasma, as disclosed in more detail in the examples that follow.

In a thirteenth aspect, the present invention provides methods for isolating native GPBP isoforms, comprising:
(a) subjecting a urine sample to salt precipitation;
(b) conducting double ion-exchange chromatography (IEC) on the salt precipitated protein sample; and
(c) identifying IEC fractions containing native GPBP isoforms.

As used herein, "double ion-exchange chromatography" means carrying out two successive and distinct ion-exchange chromatography steps prior to step (c). Exemplary embodiments of IEC techniques are well known in the art, and include those disclosed in the examples that follow.

In one preferred embodiment, these methods can be used, for example, to substantially purify native 91 kD GPBP from urine, as disclosed in more detail in the examples that follow.

In a fourteenth aspect, the present invention provides methods for isolating native GPBP isoforms, comprising:
(a) passing a plasma sample or urine sample through an affinity column comprising a GPBP-binding molecule that selectively bind to native GPBP;
(b) washing unbound protein from the plasma or urine sample from the affinity column; and
(c) eluting native GPBP isoforms from the column.

In one preferred embodiment, these methods can be used, for example, to substantially purify native 77 kD GPBP and native 91 kD GPBP from plasma and urine, as disclosed in more detail in the examples that follow. In another preferred embodiment, the GPBP-binding molecule comprise GPBP antibodies. In another preferred embodiment, the antibodies comprise the novel monoclonal antibodies of the present invention. In another preferred embodiment, the eluting step comprises use of a denaturing eluting buffer.

Details of the purification methods of the twelfth, thirteenth, and fourteenth aspects of the invention are provided in the examples below.

EXAMPLE 1

Summary

Goodpasture-antigen binding protein (GPBP) is a nonconventional Ser/Thr kinase for the type IV collagen of basement membrane. More recently, we have shown that GPBP is an extracellular protein that when overexpressed induces type IV collagen disorganization and deposit of immune complexes in glomerular basement membrane (Ref. 4). Here we show that cells expressed at least two GPBP isoforms resulting from canonical (77-kDa) and noncanonical (91-kDa) mRNA translation initiation. The 77-kDa polypeptide interacted with type IV collagen and localized as a soluble form in the extracellular compartment. The 91- and derived 120-kDa polypeptides associated with cellular membranes and regulated the levels of the 77-kDa polypeptide in the extracellular compartment. The FFAT motif and the 26-residue Ser-rich region were required for the exportation of the 77-kDa polypeptide. And removal of the 26-residue Ser-rich region yielded the previously recognized GPBP isoform (GPBPΔ26/

CERT) that was cytosolic and in contrast to GPBP, sensitive to sphingomyelinase cell treatment. These and previous data implicate COL4A3BP in a multi-compartmental program for protein secretion (i.e. type IV collagen) which includes: 1) phosphorylation and regulation of protein molecular/supramolecular organization (GPBP); and 2) inter-organelle ceramide trafficking and regulation of protein cargo transport to the plasma membrane (GPBPΔ26/CERT). Finally, we have isolated circulating 77-kDa GPBP from human plasma and have observed increased levels in Goodpasture patients and in animal models for immune complex-mediated glomerulonephritis, demonstrating that GPBP secretion occurs in vivo and revealing the clinical utility of serological determination of GPBP.

Introduction

Goodpasture antigen-binding protein (GPBP) phosphorylates the noncollagenous-1 (NC1) domain of the α3 chain of type IV collagen [α3(IV)NC1] (1). This domain is a pivotal structure in the molecular and supramolecular organization of the glomerular basement membrane (GBM) collagen and also the target of autoantibodies mediating glomerulonephritis in Goodpasture disease (2). Increased GPBP expression has been associated with autoimmune pathogenesis including Goodpasture disease (3) and with the induction of GBM collagen disorganization and deposit of IgA antibodies (4). These observations suggest that GPBP regulates GBM collagen organization and induces type IV collagen-based antibody-mediated glomerulonephritis when its expression is abnormally elevated (3, 4). COL4A3BP also encodes for GPBPΔ26, a more-abundant less-active alternatively spliced GPBP variant lacking a 26-residue Ser-rich region, which is apparently not regulated under these pathological conditions (3).

GPBP contains multiple structural elements including N terminal pleckstrin homology (PH) domain, Ser-Xaa-Yaa region, bipartite nuclear localization signal, coiled-coil domain, two phenylalanines in an acidic track (FFAT) motif and C terminal steroidogenic acute regulatory related lipid transfer (START) domain. Additional structural features include motifs for self-interaction and phosphorylation (1, 3, 5, 6). The PH domains comprise a variety of poorly conserved structures present only in eukaryotes which have been proposed to mediate protein targeting to cellular membranes through interaction with phosphoinositides (7). A variety of proteins including several protein kinases contain PH domains (8). The FFAT motifs target proteins to the ER through interaction with the transmembrane cytosolic domain of the vesicle associated membrane protein-associated proteins (VAPs) (9), which have been proposed to play a role in maintaining homeostasis for protein folding in the endoplasmic reticulum (ER) and in regulating protein cargo transport to the plasma membrane (10, 11). The START domains bind lipids including ceramide, phospholipids and sterols, and are modules present in a variety of proteins with distinct physiological and pathological functions (12, 13).

Recent reports have implicated the FFAT motif and PH domain in the binding of GPBP polypeptides to the ER and Golgi apparatus, respectively. The binding to these organelles has been postulated to enable the START domain to capture ceramide from the ER and to deliver it to the Golgi apparatus. Based on these observations, GPBP polypeptides have been described as non-vesicular cytosolic ceramide transporters and renamed $CERT_L$ (GPBP) and CERT (GPBPΔ26) (5, 14). However, the conclusions of these authors were made in the absence of precise data related to the intracellular distribution of the native proteins and in complete disregard of immunochemical evidence demonstrating predominant expression of GPBP in association with basement membranes (3). More recent reports have shown that CERT-dependent ceramide transport is critical for recruitment of phospholipase A2α as well as for the recruitment and activation of protein kinase D at the trans Golgi network, thereby ultimately regulating prostaglandin production and protein exocytosis, respectively (6, 15).

Immunohistochemical evidence suggests that GPBP is primarily extracellular, although with the potential to localize to various intracellular sites (3, 4). Protein distribution is highly informative with respect to protein function; therefore, additional studies were needed to understand the biological function of GPBP. Here we demonstrate that the translation of the mRNA for GPBP generated several polypeptides, none of which were significantly expressed in the cytosol. On the contrary, the current study provides evidence that GPBP enters into the secretory pathway and interacts with type IV collagen. Furthermore, we show that removal of 26-residue Ser-rich region by alternative exon splicing localizes the protein to the cytosol, revealing that GPBPΔ26/CERT represents a soluble, intracellular version of GPBP. The present data suggest that alternative exon splicing and translation initiation are strategies to direct the products of COL4A3BP to different locations where they are expected to coordinate a multi-compartmental biological program. Various lines of evidence support that the later includes phosphorylation and regulation of basement membrane collagen organization (GPBP) (1, 3, 4) and inter-organelle ceramide transport which regulates vesicular protein cargo transport to the plasma membrane (GPBPΔ26/CERT) (6, 14). Finally, we show that 77-kDa GPBP is a serological component that may be used as a clinical marker of antibody-mediated glomerulonephritis (i.e. Goodpasture disease and immune complex-mediated glomerulonephritis).

Materials and Methods

Processing of serum samples—Mice and human blood samples were obtained according to institutional guidelines for human studies and animal experimentation. We used sera from New Zealand white (NZW) mice that were previously characterized (4) and which represent healthy young (4-month) and old undergoing IgA immune complex-mediated (7-month). Human plasmapheresis and sera from control or Goodpasture patients were obtained following standard procedures.

Figure 9:
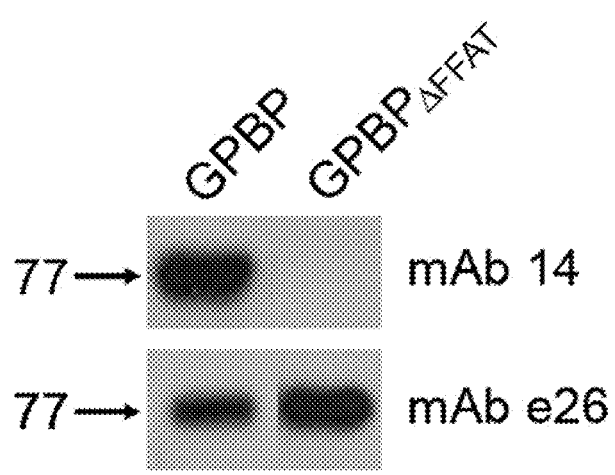
FIG. 9. The binding site of mAb 14 maps to the FFAT motif of GPBP. In A, indicated in one-letter code is the primary structure of the FFAT motif and flanking region in GPBP (residues 316-333) (SEQ ID NO:8) and the homologous region in GPBP$_{\Delta FFAT}$ (SEQ ID NO:29) where dashes indicate the deleted residues within FFAT motif (boxed). In B, cell extracts (10 µg) expressing the indicated proteins were analyzed by Western blot using the indicated antibodies.

Antibodies and recombinant proteins—Using truncated recombinant GPBP isoforms and synthetic peptides, we have mapped the epitope of GPBP/GPBPΔ26-specific mouse monoclonal antibody 14 (mAb 14) (1) to the FFAT motif (FIG. 9). Mouse mAb e26 was raised against the 26-residues characteristic of GPBP (GPBPpep1) and therefore, was not reactive with GPBPΔ26/CERT (FIG. 1A). Human monoclonal F(ab)₂ fragments were isolated from a recombinant F(ab)₂ expression library using a synthetic peptide representing the alternatively translated region (ATR) of GPBP (FIG. 2C) (Antibodies by Design, MorphoSys AG). Reactive F(ab)₂ fragments were further characterized using Western blot and recombinant proteins expressing the predicted ATR (not shown). The most reactive F(ab)₂ fragment (Ab 24) was used to characterize native GPBP polypeptides and the least reactive F(ab)₂ fragment (Ab 20) was used as negative control in these studies. The previously reported (4) immunopurified chicken polyclonal GPBP-specific antibodies (αGPBP) were biotinylated for use in flow cytometry or labeled with Alexa Fluor 647 (Invitrogen) for direct immunofluorescence. Polyclonal antibodies specific for GPBP and GPBPΔ26/CERT were produced either in rabbits immunized with GST-FLAG-GPBP (1) following standard procedures (αGPBPr) or in chickens immunized with a specific synthetic peptide and purchased from Abcam (αGPBPab). Specific antibodies in αGPBPr were affinity-purified using recombinant FLAG-GPBP (see below) bound to Sepharose-CNBr (Sigma). For glyceraldehyde-3-phosphate dehydrogenase detection, we used a mouse monoclonal antibody provided by Erwin Knecht. Polyclonal antibodies specific for calregulin, p65 or cathepsin D were from Santa Cruz Biotechnology Inc and those specific for pyruvate dehydrogenase (PDH) were from Molecular Probes. Monoclonal antibodies specific for PrP (clone 3F4) or for golgin-97 were from Clontech and Molecular Probes, respectively. To detect FLAG, we used FLAG/M2 or FLAG/M2-horseradish peroxidase (HRP) (Sigma) for Western blot analysis and chicken antibodies (αFLAG) or goat antibodies (αFLAG-FITC) for immunofluorescences (Abcam). Alexa Fluor® 488-streptavidin was from Molecular Probes and secondary antibodies were from Promega (anti-mouse and anti-rabbit HRP conjugates), Jackson Immunoresearch (anti-human F(ab)$_2$-HRP) and Sigma (anti-chicken HRP and other FITC and TRITC conjugates). Recombinant FLAG-GPBP and FLAG-GPBPΔ26 were expressed in Pichia pastoris and affinity-purified as previously described (1, 3).

Plasmid constructs—The production of pc-n4', a pcDNA3 (Invitrogen)-derived construct expressing a cDNA which contained the 5' untranslated region (UTR) and coding sequence of GPBP mRNA has been reported (1). Plasmids derived from pc-n4' included pc-GPBP-Met, a deletion mutant devoid of 5'UTR, and pc-n4'-Mmut, a construct where the canonical AUG (Met) translation initiation was substituted with GGA (Gly). The production of pc-FLAG-GPBP, which expresses the FLAG sequence fused to the coding region of GPBP, was previously reported (1) and used to obtain pc-FLAG-GPBP$_{\Delta FFAT}$, bearing a deletion in the FFAT motif (FIG. 9). The pc-FLAG-GPBPΔ26 expresses the FLAG sequence fused to the coding region of GPBPΔ26 and has been produced similarly to pc-FLAG-GPBP. To determine the initiation site that accounted for the ATR, we produced pc-n4' and pc-n4'-Mmut mutants by introducing stop codons at various positions in the open reading frame (ORF) upstream of iMet position. The pSilencer™ 2.1-U6 hygro (Ambion) was employed for transient expression of small interfering mRNAs (siRNAs) specific for GPBP or for GPBP/GPBPΔ26. The corresponding derived constructs and cDNA target sequences were: pSi-GPBP/GPBPΔ26-2, ACAGAG-TATGGCTGCAGAG (SEQ ID NO: 11); pSi-GPBP/GPBPΔ26-3, GTACTTTGATGCCTGTGCT (SEQ ID NO: 12); pSi-GPBP-1, GCCCTATAGTCGCTCTTCC (SEQ ID NO: 13). Selection of the target sequence and plasmid construction were based on manufacturer's recommendations. The efficiency of siRNA expressing-plasmids was assessed in a cell recombinant expression system (not shown). The control plasmid in these studies (pSi-Control) was designed for targeting the mRNA of green fluorescence protein, a protein not expressed in human cells. All mutants were produced by standard PCR-based mutagenesis and the fidelity of all the cDNAs cloned was confirmed by nucleotide sequencing.

Cell culture and transfection—HEK-293 or HeLa cells were grown with Dulbecco's modified Eagle's medium or Minimal Essential Medium Eagle respectively, supplemented with 2 mM L-glutamine, 10% (v/v) fetal bovine serum and penicillin (100 U/ml)/streptomycin sulfate (0.1 mg/ml), at 37° C. in a humidified 5% $CO_2$ environment. Unless otherwise indicated the cells used in the studies were HEK 293 cells.

Transfections were performed for 16-24 h using ProFection Mammalian Transfection System-Calcium Phosphate (Promega) or Lipofectamine 2000 (Invitrogen), following manufacturer's recommendations. For immunofluorescence studies, cells were seeded on poly-L-lysine-coated cover slips in 24-well plates. When indicated HEK 293 cells were transfected with pc-n4'-Mmut and selected with G418 (Invitrogen) for 15 days. Resistant cells were further cloned by limiting dilution and the expression of 91-kDa GPBP in a number of individual clones was determined by Western blot analysis of cell extracts (see below). Clones expressing elevated (c8, c14) or reduced (c19) levels of 91-kDa were used in functional studies.

In vitro transcription and translation—We used TNT® T7 Coupled Reticulocyte Lysate System (Promega) to perform in vitro transcription/translation of ~1 µg of plasmid, following the manufacturer's recommendations. For assessing protein synthesis, [$S^{35}$]methionine was added to the mixtures and labeled polypeptides were identified by SDS-PAGE and fluorography. Briefly, after electrophoresis gels were fixed 1 h with 45% methanol and 7.5% acetic acid. Subsequently, gels were treated twice with dimethylsulfoxide for 30 min and with 22.5% of 2,5-diphenyloxazol in dimethylsulfoxide for additional 30 min. Finally, gels were equilibrated with water, dried and exposed at −70° C.

Cell extracts and cellfractioning—To obtain cell extracts, growing cultures were rinsed with ice-cold phosphate buffered-saline (PBS) and homogenized on ice bed with 25 mM Tris-HCl pH 7.5, 150 mM NaCl, 0.5% Triton X-100, 1 mM phenylmethylsulphonyl fluoride (PMSF) and 10 µg/ml leupeptin. Mixtures were cleared by centrifugation at 500×g for 10 min, protein concentration determined and stored at −70° C.

For subcellular fractionation, cultures at 90% confluence were collected in PBS and subjected to centrifugation (500×g for 10 min). Cellular pellets were dispersed in 250 mM sucrose, 10 mM PBS pH 7.5 containing 10 µg/ml leupeptin, 1 mM PMSF and disrupted with Dounce homogenization (20 strokes) using a glass pestle. Cell homogenates were cleared progressively by sequential centrifugation to obtain the different cell fractions. Nuclei and unbroken cells were collected by centrifugation at 500×g for 10 min. The supernatant was further cleared by centrifugation at 7,000×g for 10 min to obtain mitochondrial/lysosome fraction. Finally, the supernatant was cleared by centrifugation at 150,000×g for 1 h to obtain microsomal fraction which contains fragments of cellular membranes i.e. endoplasmic reticulum, plasma membrane and secretory vesicles (pellet) and the cytosolic fraction (supernatant). All steps were performed at 0-4° C. and protein concentrations determined using Protein Assay reagent (Bio-Rad).

For some purposes, the supernatant of 500×g was loaded on a resource-Q FPLC column, and the bound material eluted in 0 to 1 M NaCl gradient in 10 mM Tris-HCl pH 8.0. The 0.55-0.6 M NaCl fractions containing the bulk of cellular GPBP were precipitated with ethanol and used as partially purified GPBP for Western blot analysis.

Ex vivo cross-linking, sphingomyelinase treatment and FLAG-immunoprecipitation—For ex vivo cross-linking, we used HEK 293-FLAG-α3(IV) cells expressing an exportable human α3(IV)NC1 domain (BM40-FLAG-α3(IV)NC1) which was obtained essentially as previously reported (1, 16). Cells were grown up to 70-90% of confluence in either 150-mm plates (native GPBP) or six-well plates (recombinant GPBP). Cross-linking was performed 48 h after transfection or when cells reached the indicated confluence. Briefly, cells were brought to RT by rinsing with PBS and incubated for 10 min with culture medium containing 1% formaldehyde. The cross-link reaction was quenched with 125 mM Gly-HCl in PBS (pH 7.4) for 10 min at RT. Cells were brought to 4° C. by rinsing with ice-chilled PBS and procedure continued at 4° C. Cells were lysed with 1 or 5 ml (six-well or 150-mm plate) of extraction buffer [16 mM Tris-HCl pH 7.5, 160 mM NaCl, 2 mM ethylenediaminetetraacetic acid (EDTA), 1.1% Triton X-100, 0.01% SDS, 10 µg/ml leupeptin, 1 mM PMSF] for 30 min, centrifuged at 500×g for 10 min to remove cell debris and the supernatants were overnight extracted with 50 or 250 µl (six-well or 150-mm plate) of a 50% slurry of αFLAG-affinity gel using gentle rocking. The beads were collected by centrifugation and washed twice with 1 ml of extraction buffer and once with Tris-buffered saline (TBS, 50 mM Tris-HCl pH 7.5, 150 mM NaCl). Proteins were eluted twice with 25 or 125 µl (six-well or 150-mm plate) of a 100 µg/ml solution of FLAG peptide in TBS at RT. Eluted samples were boiled with electrophoresis sample buffer (2×) for 15 min to reverse cross-linking and further analyzed by SDS-PAGE and either Coomassie blue staining or Western blot.

When indicated, HeLa cells transfected with pc-FLAG-GPBP or pc-FLAG-GPBPΔ26 were treated or not with *Bacillus cereus* sphingomyelinase (Sigma) as previously described (5) and cells were either fixed with methanol/acetone and analysed by direct immunofluorescence (see below) or lysed in 10 mM Tris-HCl pH 7.5, 150 mM NaCl, 0.5% Triton X-100, 1 mM EDTA, 50 mM NaF, 1 mM sodium orthovanadate, 10 µg/ml leupeptin, 1 mM PMSF, cleared by centrifugation (500×g for 10 min) and used for FLAG-immunoprecipitation (see above). The immunopurified materials from untreated cells were divided and one-half was treated with 5 U/µl of λPPase (New England Biolabs) at 30° C. for 30 min following manufacturer's recommendations. All the samples were further analysed by Western blot using anti-FLAG antibodies.

For some experiments, cells were grown in 150-mm plates, transfected with 20 µg of plasmid constructs encoding FLAG-tagged proteins and cultured for two additional days in fresh media. Twenty milliliters of media were used for FLAG-immunoprecipitation essentially as above indicated.

Flow cytometry—Cells were gently detached and dispersed in culture media. Non-specific antibody binding sites on cell surface were blocked with mouse ascites fluid containing non-relevant mAb (blocking solution). Cells were subsequently incubated in blocking solution in the presence or absence of biotinylated αGPBP with or without blocking peptide (GPBPpep1) or a non-relevant synthetic peptide. Cells were incubated with Alexa Fluor® 488-streptavidin in blocking solution and further subjected to analysis in a Cytomics FC500 flow cytometer (Beckman Coulter) to measure fluorescence emission. Cell integrity was assessed measuring forward and side scattering, using untreated fresh cells as reference. All incubations were at RT for 1 h.

Direct and indirect immunofluorescence with fixed cell—Cells were transfected and fixed with methanol-acetone (1/1) chilled at −20° C. for 10 min. Subsequently, cells were incubated with blocking solution (rabbit serum diluted 1:2 in PBS) for 30 min at RT, incubated with the primary antibodies (20 µg/ml in blocking solution) for 2 h at 37° C. in a humidified chamber, followed by incubation with the secondary antibody (1:200 in blocking solution) for 1 h at RT. Cells were stained with DAPI (1.25 µg/ml) in mounting fluid (DAKO) and visualized in an Axioskop-2 plus microscope (Carl Zeiss) combined with a Spot camera and software v2.2 (Diagnostic Instruments). For some experiments, cells were transfected, fixed, incubated with αFLAG-FITC and visualized as above indicated. Non-transfected cells were used as negative controls.

Direct immunofluorescence of living cells—Cells were cultured on glass-bottom microwell dishes (MatTek Corp) and when they reached ~50% confluence, the media were discarded and replaced by fresh media containing 10 µg/ml αGPBP-Alexa Fluor 647 with an excess of GPBPpep1 or equimolecular amounts of an unrelated synthetic peptide along with Rhodamine 123 (Invitrogen) for mitochondrial staining of living cells. Live cell analysis of fluorescence was performed with a Leica TCS SP2 inverted confocal microscope. Cells were maintained at 37° C. in a humidified 5% $CO_2$ environment in all the steps.

Mass spectrometry—Individual protein bands were excised from Coomassie blue-stained gel, distained, in-gel trypsin digested, and centrifuged. One microliter of the supernatant was dried and resuspended with 1 µl of matrix solution (a-Cyano-4-hydroxycinnamic acid, from Sigma), applied to the sample plate, dried and introduced into the mass spectrometer. Tryptic digests peptides were analyzed by MALDI/TOF/TOF mass spectrometry (4700 Proteomics Analyzer, Applied Biosystems). Collected data were analyzed with GPS software (Applied Biosystems) and protein identification was carried out using the search engine MASCOT v 2.0 (Matrix Science).

Isolation of circulating GPBP from human plasma—Ten milliliters of plasmapheresis from Goodpasture patients were applied to a Sepharose-CNBr (Sigma) column (1 ml bed) containing 5 mg of covalently bound αGPBPr. The column was washed with 20 ml of TBS containing 0.05% Tween 20 (TBST) and eluted with Gentle-Immunopure elution buffer (Pierce). Eluted material was dialyzed against TBS, concentrated with a Microcon YM-3 (Millipore) and further analyzed by Western blot using αGPBPab.

Estimation of circulating GPBP levels—Individual wells of microtiter plates were coated overnight with αGPBPr (2 µg/ml in TBS) and further incubated with blocking buffer (3% BSA in PBS) for 2 h. Recombinant GPBP and serum samples were diluted in bovine foetal serum and incubated in duplicate for 2 h. Plates were then incubated for 1 h each with αGPBPab (1:5,000 in TBS) and with anti-chicken HRP-conjugated (1:20,000 in TBS). All the steps except coating (4° C.) were at RT and wells were washed extensively with TBST between steps. Finally, detection was done using Amplex UltraRed reagent (Invitrogen) with an excitation/emission maxima 568/581 nm in a Victor 2 microtiter plate reader (PerkinElmer). A linear range of the standard curve was found between 0.5 and 10 ng/ml of recombinant GPBP. We used Mann-Whitney test to assess differences between series. A P value <0.05 was considered significant. Prism 4.0 software (GraphPad Software, San Diego, Calif.) was used for calculations.

SDS-PAGE and Western blot analysis—Were performed under reducing conditions following standard procedures and using chemiluminescence (Amersham Pharmacia Biotech) for antibody detection.

Results

COL4A3BP encodes for polypeptides of 77-, 91- and 120-kDa—To identify GPBP and GPBPΔ26, we have used two different monoclonal antibodies: mAb 14 previously reported to recognize GPBP and GPBPΔ26 (1), and mAb e26, a novel monoclonal antibody raised against the 26-residue Ser-rich region exclusive for GPBP (FIG. 1A). Using GPBP deletion mutants and synthetic peptides, we have mapped mAb 14 epitope to the FFAT motif and thus, this antibody did not react with a GPBP mutant lacking the FFAT motif ($GPBP_{\Delta FFAT}$) (FIG. 9).

Western blot analysis of cell extracts revealed that mAb 14 mainly recognized a single polypeptide with an apparent molecular weight ($M_r$) of ~77-kDa[1] whereas mAb e26 reacted with two polypeptides of ~91- and 120-kDa $M_r$ (FIG. 1B). Minor and variable reactivity was also observed towards polypeptides of ~77-, 60-, 50- and 32-kDa with mAb e26 and against polypeptides of ~91- and 120-kDa with mAb 14 (not shown). We found similar reactive molecular species in a number of cultured human cells including HEK 293 (FIG. 1B), human fibroblasts, HeLa, hTERT-RPE and hTERT-BJ1 cells (not shown).

(1) The 77-kDa polypeptide can be resolved as a doublet representing phosphorylated (higher) and dephosphorylated (lower) versions of GPBPΔ26/CERT (5)

To further characterize COL4A3BP products, we compared expression of native and recombinant mRNAs (FIG. 1C). For these purposes, pc-n4', a construct bearing the 5'UTR and coding sequence of COL4A3BP (1, 17), was used in transient gene expression assays in cultured cells. The expression of pc-n4' yielded three polypeptides of 77-, 91- and 120-kDa which were detected by mAb e26. In contrast, only the ~77- and 91-kDa polypeptides were significantly reactive with mAb 14. Strikingly, the most prominent mAb e26-reactive polypeptide in the recombinant lysates (77-kDa), representing the previously reported mRNA product (1), did not have a significant native counterpart. We also observed that mAb 14 reacted comparatively stronger with the 91- than with 120-kDa recombinant polypeptides.

To further determine the origin of native polypeptides, we used small interfering RNAs (siRNAs) specific for COL4A3BP (FIG. 1D). The expression of all three native polypeptides was reduced when expressing these siRNAs; however, siRNA specific for both GPBP and GPBPΔ26/CERT were more efficient at reducing the expression of 77-kDa polypeptide whereas GPBP-specific siRNA reduced more effectively the expression of 91- and 120-kDa polypeptides (compare pSi-GPBP/GPBPΔ26-3 and psiGPBP-1). Collectively, our data suggested that major cellular products of COL4A3BP included GPBPΔ26/CERT (77-kDa) and the previously unrecognized GPBP isoforms of 91- and 120-kDa, the later likely bearing a modified FFAT motif that prevented consistent mAb 14 binding. The reduction in the cellular levels of 77-kDa polypeptide when using GPBP-specific siRNAs requires further investigation since this polypeptide displayed no significant reactivity with mAb e26 (FIG. 1B).

Major cellular GPBP isoforms result from noncanonical mRNA translation initiation—To further define the origin of cellular GPBP isoforms, we produced (pc-n4')-derived constructs expressing mRNA mutants consisting of 5'UTR-deletion or iMet to Gly substitution (FIG. 2A) and these were used in protein expression assays (FIG. 2B). In cells, the construct representing 5'UTR-deleted mRNA (pc-GPBP-Met) produced only the 77-kDa polypeptide and the constructs representing the iMet to Gly substitution (pc-n4'-Mmut) expressed only the 91- and 120-kDa polypeptides (FIG. 2B, ex vivo). However, in a cell-free translation system, pc-GPBP-Met also expressed 77-kDa GPBP polypeptide but pc-n4'Mmut yielded only the 91-kDa polypeptide and no significant expression of 120-kDa polypeptide was observed (FIG. 2B, in vitro). These data indicated that GPBP mRNA contained a noncanonical translation initiation site(s) in the 5'UTR that accounted for polypeptides of 91- and 120-kDa whereas the 77-kDa polypeptide was the product of canonical translation initiation. Moreover, our data also suggested that the 91-kDa was the primary product of noncanonical translation initiation and the 120-kDa polypeptide represented a posttranslational derived product that could not be expressed in a cell-free system devoid of cellular membranes.

To characterize further noncanonical translation initiation, the previously recognized (1) ORF present in the 5'UTR of the GPBP mRNA (FIG. 2C) was interrupted by introducing a stop codon at individual positions in pc-n4'Mmut and cellular protein expression assessed by Western blot (FIG. 2D). The construct bearing a stop codon at −83 (originally ACG, threonine) did not express the 91- and 120-kDa polypeptides, but the construct with the stop codon at −84 (originally GCG, alanine) expressed the two polypeptides mapping the alternative translation start site to codon −83 (boxed Thr in FIG. 2C). The same conclusion was obtained when we assayed the −83 stop-mutant of pc-n4' (FIG. 2D).

To confirm that noncanonical translation initiation also accounted for endogenous GPBP polypeptides of 91- and 120-kDa, a human $F(ab)_2$ fragment (Ab 24) specifically reacting with a synthetic peptide representing the predicted ATR (shaded sequence in FIG. 2C) was used for Western blot analysis of partially purified GPBP polypeptides (FIG. 2E). As expected, Ab 24 specifically reacted with two polypeptides of 91- and 120-kDa which were also recognized by mAb e26, suggesting that native GPBP polypeptides contained the ATR characteristic of noncanonical translation products.

The 91- and 120-kDa GPBP isoforms are insoluble membrane-bound polypeptides—GPBP isoform of 91-kDa was predicted to be non-classical secreted proteins when analyzed with SecretomeP 2.0 Server (18, http://www.cbs.dtu.dk/services/SecretomeP/) and to localize in mitochondria (60.9%), nucleus (26.1%), cytoskeleton (8.7%) and vesicles of secretory system (4.3%) when analyzed with PSORT II Prediction (http://psort.ims.u-tokyo.acjp/form2.html). Thus, these theoretical considerations suggested that GPBP isoforms resulting from noncanonical translation initiation were noncytosolic polypeptides that entered into cellular organelles including the secretory pathway.

Figure 3:
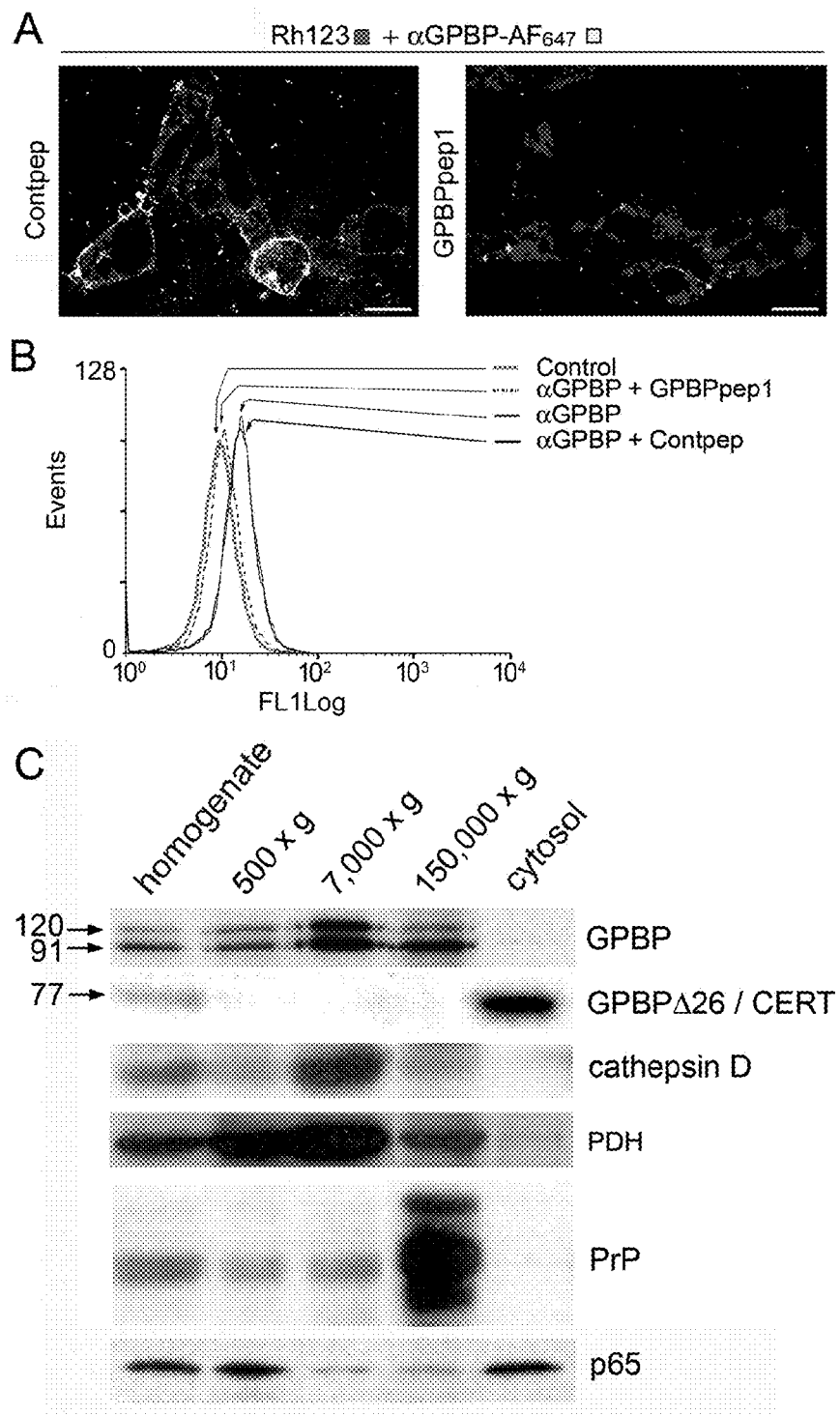
FIG. 3. The 91- and 120-kDa GPBP isoforms are insoluble membrane-bound polypeptides. In A, intact cells were incubated with αGPBP-Alexa Fluor 647 antibodies (αGPBP-AF647) in the presence of GPBPpep1 or equimolecular amount of a nonrelevant peptide (Contpep) and Rhodamine 123 for mitochondrial staining of living cells, and analyzed by confocal microscopy. Scale bar, 21 μM. In B, cells were detached and incubated with blocking solution in the absence (control) or presence of biotinylated αGPBP antibodies (αGPBP). The cell surface-bound antibody was detected with streptavidin-FITC and flow cytometry. As a control, parallel cultures were incubated with the same antibodies in the presence of GPBPpep1 (αGPBP+GPBPpep1) or equimolecular amount of a non-relevant peptide (αGPBP+Contpep) and similarly analyzed. In C, similar amounts (10 μg) of the indicated cellular fractions were analyzed by Western blot using antibodies for the indicated proteins. We used as cellular compartment markers: pyruvate dehydrogenase (PDH) for mitochondria; cathepsine D for lysosome; prion protein (PrP) for microsome; and nuclear factor kappa B (p65) for nucleus and cytosol. For GPBP and GPBPΔ26/CERT detection, we used mAb e26 and mAb 14, respectively. Since we did not detect expression of 77-kDa GPBP in the cytosol, mAb 14 reactivity in this compartment can be attributed to GPBPΔ26/CERT.

To assess these predictions, intact living cells were incubated with αGPBP and analyzed by direct immunofluorescence and flow cytometry for antibody binding detection (FIGS. 3A and 3B). Interestingly, αGPBP bound to living cells in a specific manner since binding of the antibodies was efficiently abolished by a synthetic peptide representing GPBP (GPBPpep1) but not by an unrelated polypeptide (Contpep). These data suggested that cellular GPBP isoforms were present in the external surface of the plasma membrane.

To further characterize the intracellular distribution of GPBP, cells were disrupted and subjected to subcellular fractionation and Western blot analysis (FIG. 3C). Consistent with predictions, GPBP isoforms of 91- and 120-kDa were not detected as soluble materials but rather they were found mainly associated with mitochondrial-lysosomal and microsomal fractions. It remained to be determined whether the presence of GPBP in the nuclear fraction indeed reflected nuclear expression of these proteins or rather unbroken cells and/or mitochondria contaminating this fraction. In contrast, a polypeptide of ~77-kDa which reacted with mAb 14 and showed no significant reactivity with mAb e26 was exclusively detected as soluble after sample centrifugation at 150,000×g for 1 h (cytosol).

These data suggested that native GPBP polypeptides of 91- and 120-kDa were expressed insoluble associated with cellular membranes whereas native GPBPΔ26/CERT polypeptide of 77-kDa was expressed soluble in the cytoplasm.

Figure 4:
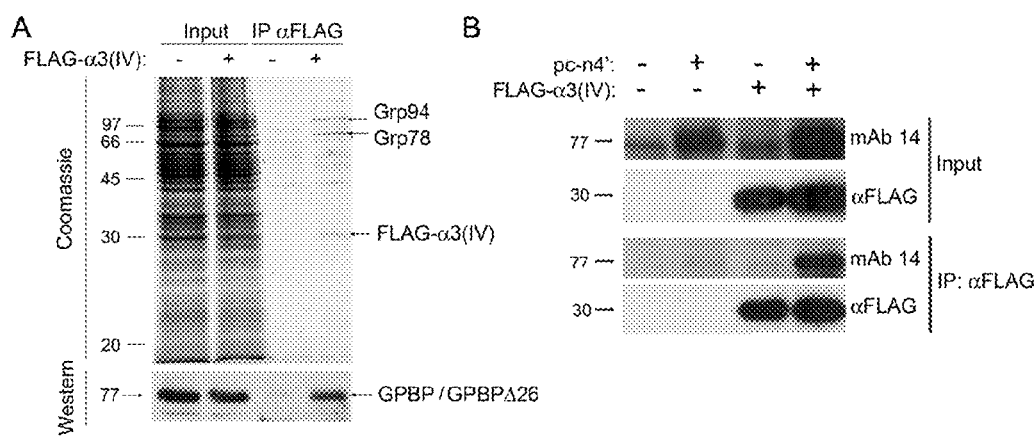
FIG. 4. The 77-kDa GPBP isoform interacts with type IV collagen in cultured cells. In A, HEK 293 or HEK 293-FLAG-α3(IV) cells were cross-linked, lysed and αFLAG extracted. Fifty micrograms of cell lysate (Input) or the corresponding FLAG-immunoprecipitated materials (IP αFLAG) were reversed cross-linked and analyzed by Coomassie blue staining or Western blot with αGPBPr. The major specific polypeptides in FLAG-immunoprecipitates (arrows) were excised and identified by MALDI/TOF/TOF mass spectrometry. In B, HEK 293 (–) or HEK 293-FLAG-α3(IV) (+) cells were transfected with pcDNA3 (–) or with pc-n4' (+), cross-linked, processed and analyzed as in A by Western blot using the indicated antibodies.

The 77-kDa GPBP is a soluble extracellular protein which interacts with type IV collagen—Previous reports suggested that 77-kDa GPBP interacts with type IV collagen (1, 3, 4). This was further assessed by ex vivo cross-linking and FLAG-immunoprecipitation of cells expressing or not expressing BM40-FLAG-α3(IV)NC1, a recombinant exportable form of the human α3(IV)NC1 (16), followed by SDS-PAGE analysis of immunoprecipitates (FIG. 4A). FLAG-specific antibodies efficiently precipitated FLAG-α3(IV) NC1 and a 77-kDa polypeptide representing either GPBP or GPBPΔ26/CERT[(2)] (Western) along with Grp78 and Grp94 (Coomassie), two ER resident chaperones implicated in protein folding and ER homeostasis maintenance (19, 20). To further determine that GPBP indeed interacted with FLAG-α3(IV) in the ER, cells expressing or not expressing BM40-FLAG-α3(IV)NC1 were transfected with pc-n4' and similarly analyzed (FIG. 4B). FLAG antibodies efficiently precipitated 77-kDa GPBP from cells expressing FLAG-α3 (IV)NC1 but not from control cells, suggesting that 77-kDa GPBP isoform enters into the secretory pathway and interacts with FLAG-α3(IV)NC1.

(2) Secretion of 77-kDa GPBP associated with loss of reactivity with mAb e26 (FIG. 11), excluding the use of this antibody to estimate the levels of native 77-kDa GPBP in the secretory pathway.

Figure 2:
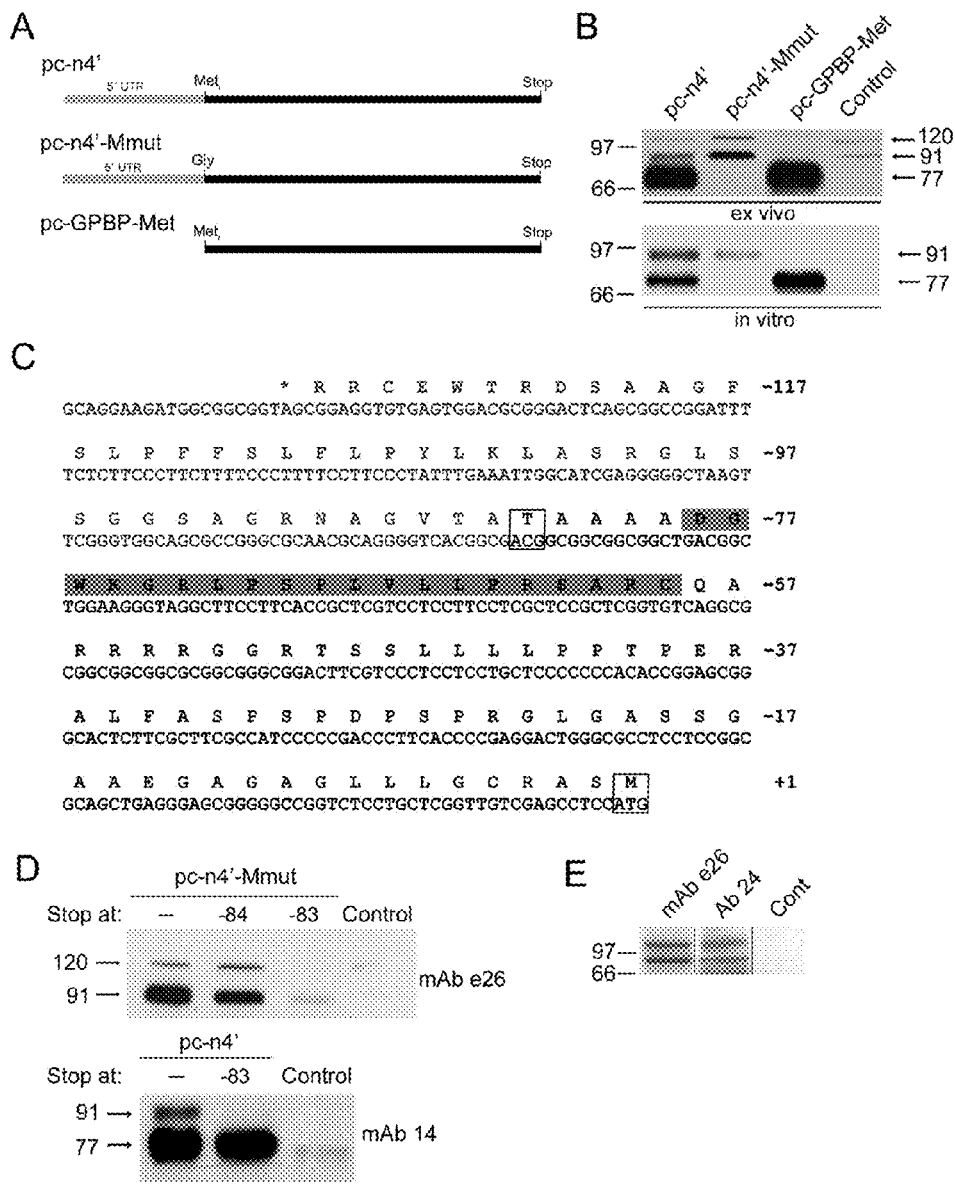
FIG. 2. GPBP polypeptides of 91- and 120-kDa are the products of mRNA noncanonical translation initiation. In A, schematic representation of the cDNAs used to construct the indicated plasmids. In B, cell extracts (10 μg) (ex vivo) or individual transcription/translation mixtures (in vitro) expressing the indicated plasmid construct were analyzed by Western blot using mAb e26 (ex vivo) or by fluorography (in vitro). Lysates from untransfected cells (ex vivo) or mixtures without plasmid (in vitro) were used as Control. In C, indicated are the sequence of the N terminal open reading frame (ORF) of GPBP in one-letter code (SEQ ID NO:15) and the corresponding mRNA nucleotide sequence (SEQ ID NO:14) in capital letters. The gray and black letters indicate the 5'-UTR and ATR, respectively. Boxed are the codons and residues for canonical and noncanonical translation initiation. The peptide sequence targeted by Ab 24 is highlighted in gray. The negative numbers at right denote the position of the codon or residue from canonical translation initiation site (AUG or Met, +1). In D, extracts (10 μg) from cells not expressing (Control) or expressing the indicated plasmid constructs without (–) or with a stop codon at the indicated positions were analyzed by Western blot using the indicated antibodies. In E, partially purified cell extracts (50 μg) were analyzed by Western blot using the indicated reactive species and a non-reactive F(ab)$_2$ Ab 20 (Cont).

Primary structure analysis predicted a cytoplasmic localization for 77-kDa GPBP polypeptide (unpublished observations). However, in vitro (1, 3), ex vivo (FIG. 4) and in vivo (4) studies suggested that 77-kDa GPBP isoform binds and phosphorylates type IV collagen. Furthermore, although recombinant expression studies revealed that the 77-kDa GPBP polypeptide was the most prominent polypeptide, no significant levels of the native counterpart were detected within the cells (FIG. 1). Collectively, these observations suggested that canonical GPBP was a cytosolic polypeptide subjected to a nonclassical secretion.

Figure 5:
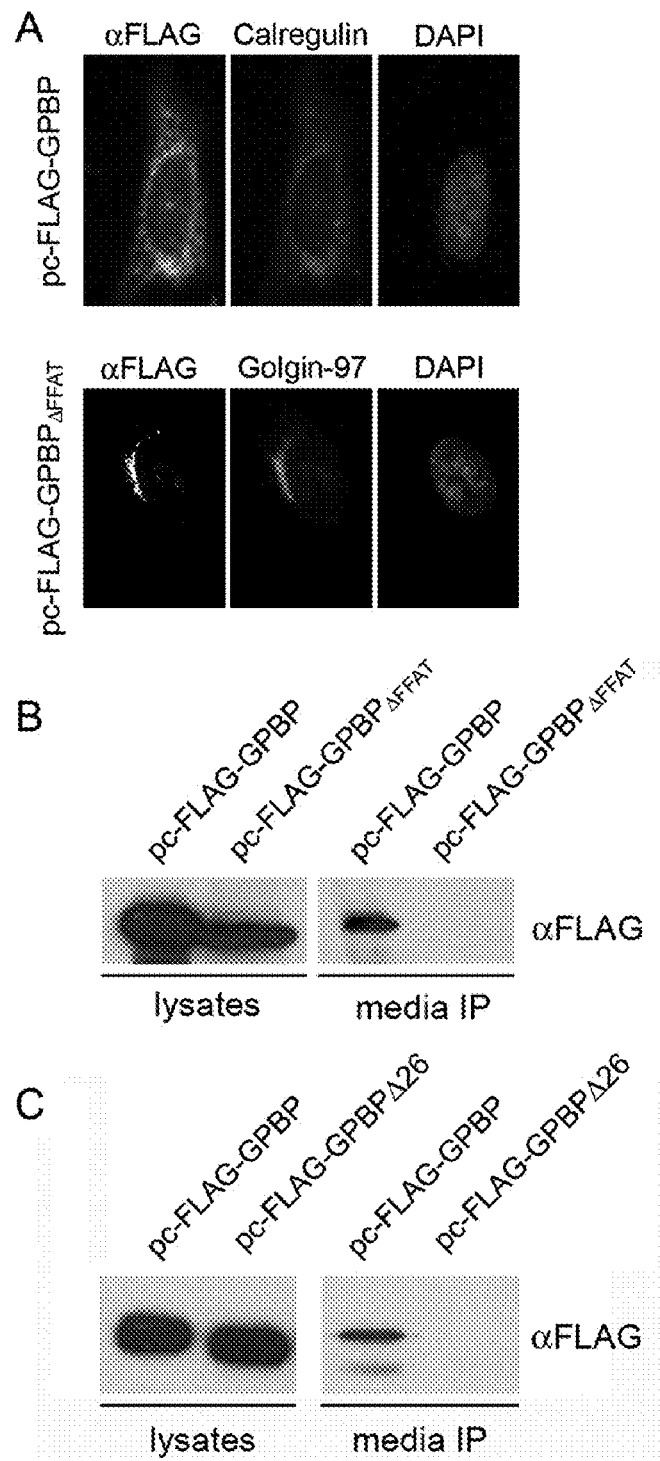
FIG. 5. Export of 77-kDa GPBP to the extracellular compartment. In A, HeLa cells were transfected with the indicated plasmid constructs, and the indicated proteins visualized by standard indirect immunofluorescence. DNA was stained with 4'-6'-diamino-2-phenylindole (DAPI) for nuclear visualization. Original magnification×400. In B and C, extracts (10 µg) from cells expressing the indicated plasmid constructs (lysates) or FLAG-immunoprecipitates from the corresponding culture media (media IP) were analyzed by Western blot using the indicated antibodies.

To explore whether GPBP is secreted, we first expressed FLAG-tagged GPBP in HeLa cells and used FLAG-specific antibodies to analyze intracellular recombinant protein distribution (FIG. 5A). FLAG-GPBP co-localized extensively with calregulin, an ER resident protein, suggesting that, as described for GPBPΔ26/CERT (21, 22), FLAG-GPBP bound to the ER through FFAT-VAP interaction. Consequently, we expressed and similarly analyzed FLAG-GPBP$_{\Delta FFAT}$, a FLAG-GPBP variant devoid of FFAT motif. Deletion of FFAT motif prevented distribution of GPBP to the ER as the protein was found extensively co-localizing with golgin-97, a Golgi apparatus resident protein (FIG. 5A). Identical conclusions were obtained when the studies were conducted in HEK 293 cells (not shown). Our data were consistent with the notion that recombinant GPBP was a cytosolic protein bound to VAP through the FFAT motif for its exportation and only when FFAT-interaction was impaired, the protein had the potential to associate with Golgi apparatus. This was explored by expressing FLAG-GPBP or FLAG-GPBP$_{\Delta FFAT}$ in cultured cells and the subsequent analysis of culture media by immunoprecipitation and Western blot analysis (FIG. 5B). Interestingly, FLAG-specific antibodies efficiently immunoprecipitated recombinant protein from the media of cultures expressing FLAG-GPBP but not from the media of cells expressing FLAG-GPBP$_{\Delta FFAT}$, revealing that FFAT-mediated binding to the ER is essential for 77-kDa GPBP secretion.

GPBPΔ26/CERT also binds to the ER in a FFAT-dependent manner (21, 22); however, we found GPBPΔ26/CERT in the cytosol and 77-kDa GPBP in the extracellular compartment, supporting that the Ser-rich 26-residue region exclusive to GPBP is also critical for GPBP secretion. This was similarly explored in cultures expressing FLAG-tagged 77-kDa GPBP or GPBPΔ26/CERT (FIG. 5C). As expected, the presence of the 26-residue Ser rich region was critical for protein secretion given that FLAG-GPBPΔ26 was not significantly expressed in the culture media.

The 91-kDa GPBP regulates the levels of 77-kDa GPBP in the extracellular compartment—The evidence supports that both the 77- and 91-kDa GPBP isoforms enter into the secretory pathway but whereas the 91-kDa remains associated to membranes, the 77-kDa GPBP is soluble in the extracellular compartment. We have explored whether 91-kDa GPBP regulates the extracellular levels of 77-kDa GPBP. This was accomplished by recombinant expression of FLAG-GPBP in individual cell lines expressing recombinant 91-kDa GPBP to a different levels (FIG. 6A) followed by FLAG-immunoprecipitation of the corresponding cultured media and analysis of immunoprecipitates by Western blot (FIG. 6B). Interestingly, increased expression of recombinant 91-kDa GPBP associated with increased levels of FLAG-GPBP in the culture media, suggesting that 91-kDa GPBP induced the secretion of 77-kDa GPBP to the extracellular compartment.

Figure 7:
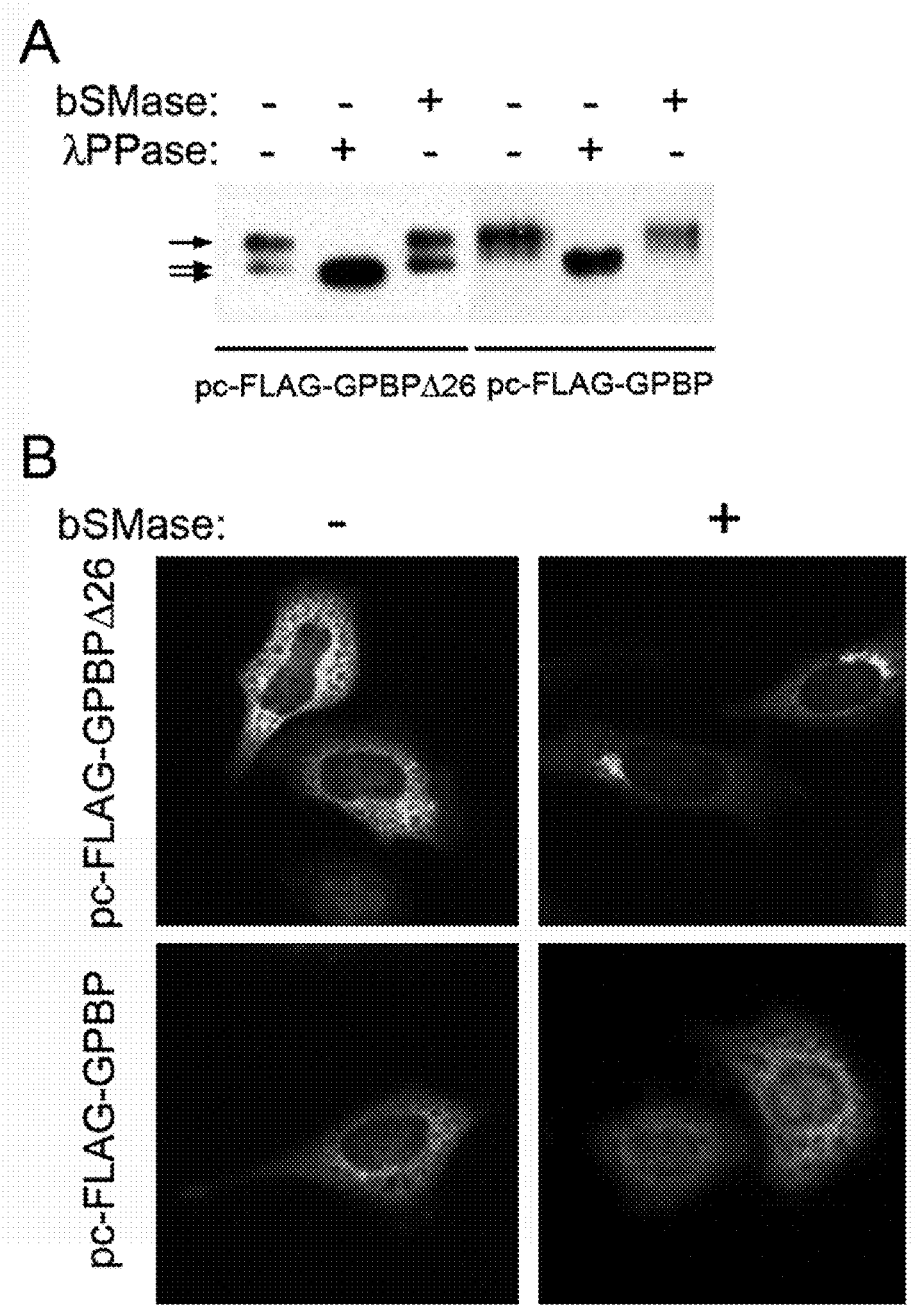
FIG. 7. GPBPΔ26/CERT but not GPBP is sensitive to sphingomyelinase cell treatment. In A, HeLa cells were transfected with the indicated plasmid contracts and treated (+) or not (−) with spingomyelinase, lysed, FLAG-immunoprecipitated, and analyzed by Western blot with αFLAG antibodies (bSMase). Immunoprecipitates from untreated cells were incubated (+) or not (−) with phosphatase and similarly analyzed (λPPase). We have used a 8-12% gradient gel and extensive electrophoresis to separate phosphorylated and dephosphorylated versions of GPBPΔ26/CERT and estimated their relative abundance by Western blot and densitometry. In B, the same cells as in A were fixed by methanol/acetone, double-labeled with anti-FLAG-FITC antibody (green) and DAPI (blue) and analyzed by direct immunofluorescence. Original magnification ×400.

The 77-kDa GPBP is not sensitive to cell treatment with sphingomyelinase—Recombinant expression studies also showed that 77-kDa GPBP was a cytosolic polypeptide associated with ER that underwent translocation to the Golgi apparatus when FFAT motif was mutated (FIG. 5A). Consequently, we asked whether 77-kDa GPBP underwent dephosphorylation and translocation to the Golgi apparatus in response to sphingomyelinase cell treatment as previously reported for GPBPΔ26/CERT (5). For these studies, cells expressing FLAG-tagged GPBP or GPBPΔ26/CERT were treated with *Bacillus cereus* sphingomyelinase (bSMase) and intracellular proteins of interest were analyzed by FLAG-immunoprecipitation and Western blot (FIG. 7A). As previously noted (1, 5), both recombinant proteins were phosphorylated and treatment with a general phosphatase (λPPase) reduced their $M_r$ to a similar extent (top and bottom arrows). However, sphingomyelinase cell treatment had different consequences for each recombinant protein; whereas FLAG-GPBPΔ26/CERT shifted to a lower $M_r$ (top and middle arrows), no significant $M_r$ shift was observed for FLAG-GPBP. This suggested that the reduction in the cellular levels of sphingomyelin caused by sphingomyelinase treatment induced the dephosphorylation of FLAG-GPBPΔ26/CERT but did not affect significantly the phosphorylation state of FLAG-GPBP. As expected, immunofluorescence analysis of the cells revealed that sphingomyelinase treatment promoted translocation of FLAG-GPBPΔ26/CERT to the Golgi apparatus without altering significantly the intracellular distribution of FLAG-GPBP (FIG. 7B).

Figure 8:
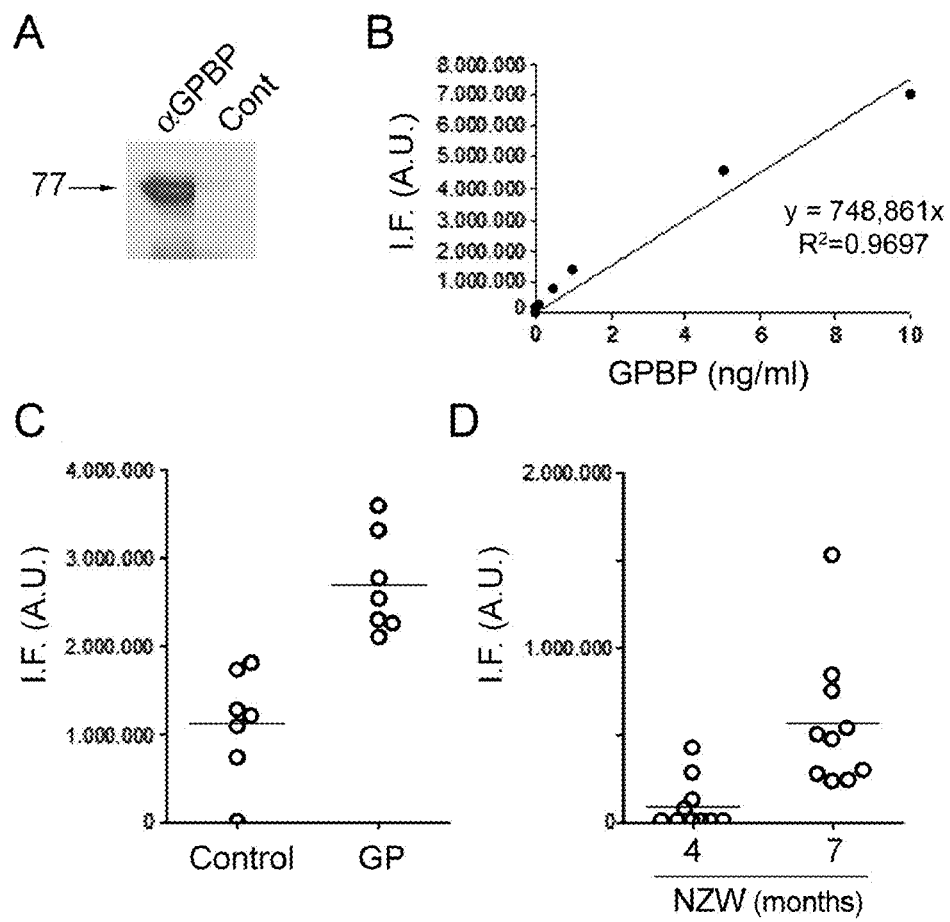
FIG. 8. The levels of circulating 77-kDa GPBP are up-regulated in Goodpasture patients and in animal models of immune complex-mediated glomerulonephritis. In A, material isolated by immunoaffinity chromatography from a Goodpasture patient plasmapheresis was analyzed by Western blot in the presence (αGPBP) or absence (Control) of GPBP-specific antibodies. In B, is the plot representing the standard curve obtained from an ELISA performed as in Material and Methods indicated using recombinant GPBP. In C and D are scatter plots of intensity of fluorescence (I.F.) in arbitrary units (A.U.) measured by similar ELISA. Sera from healthy donors (Control), Goodpasture patients (GP), and from NZW mice of the indicated ages were diluted 1:10. The fluorescence in the absence of sera was considered background and subtracted from each individual value. In both series, P<0.001. Bars indicate the mean of each series and a circle represents the mean value of individual samples. In A-D, αGPBPr was the capturing and αGPBPab the detecting antibodies.

Circulating levels of 77-kDa GPBP are upregulated in Goodpasture patients and in animal models of immune complex-mediated glomerulonephritis—Evidence suggested that 77-kDa GPBP was secreted as a soluble protein in vivo was first investigated by immunoaffinity chromatography to isolate circulating human 77-kDa GPBP (FIG. 8A). We used plasmapheresis obtained by standard therapeutic procedures from Goodpasture patients, which were predicted to express higher levels of GPBP (3). As expected, we identified a single polypeptide of 77-kDa in the material eluted from the affinity column which reacted with the GPBP-specific antibodies, suggesting that 77-kDa GPBP is secreted in vivo and is a component of the human plasma. To both validate affinity purification and determine the levels of 77-kDa GPBP in a more precise manner, we developed an ELISA employing the same antibodies which were used in affinity chromatography to capture and detect human recombinant GPBP (FIG. 8B). We used this ELISA to estimate circulating 77-kDa GPBP levels in samples representing control and antibody-mediated glomerulonephritis (FIG. 8C, D). The ELISA displayed a linear range between 0.5 ng and 10 ng/ml when measuring recombinant GPBP (FIG. 8B) and detected comparatively more circulating 77-kDa GPBP in Goodpasture patients than in control individuals (FIG. 8C). We obtained similar results when comparing young (4-month) and aged (7-month) NZW mice (FIG. 8D), a mouse strain that develops GPBP-dependent IgA immune complex-mediated glomerulonephritis and lupus-prone autoantibody production commencing at 7 months of age (4).

Discussion

Here we have obtained compelling evidence that the mRNA of GPBP undergoes canonical (AUG) and noncanonical (ACG) translation initiation to generate two primary polypeptides of 77- and 91-kDa, respectively. The results from the present study also support that both products enter the secretory pathway. However, whereas the 77-kDa reaches the extracellular compartment and exists in a soluble immunoprecipitable form, the 91- and its derived 120-kDa polypeptides remain mainly insoluble, associated with cellular membranes. The use of translation initiation at ACG and noncanonical translation initiation to direct proteins to alternative cell compartments has been described for other human genes (23, 24). Based on previous evidence (21, 22), it is expected that FFAT-mediated GPBP binding to the ER (FIG. 5) occurs through VAP and therefore that FFAT-VAP interaction mediates molecular mechanisms underlying GPBP translocation into the ER. Furthermore, we also show that the previously reported alternatively-spliced GPBPΔ26/CERT is a GPBP variant that remains mainly soluble in the cytoplasm. Thus, our data support the notion that mRNA alternative translation initiation and exon splicing are strategies to direct GPBP to multiple locations including the cytosol, secretory pathway, plasma membrane and extracellular compartment. Moreover, previous observations have localized GPBP to the nucleus in human spermatogonium (1) and in the mitochondria and lysosome of rat liver (unpublished observations), suggesting that the distribution of GPBP is virtually ubiquitous and therefore, its biological program is expected to be exerted in several compartments.

A human GPBP cDNA from pulmonary artery endothelial cell has been reported (GenBank accession number AK096854). Interestingly, AK096854 bears an alternative canonical translation initiation site (iMet) that extends the ORF of the 91-kDa polypeptide upstream by 45 residues. We have not found evidence for AK096854 mRNA expression in HEK 293 cells, nor in a number of other human tissues including liver, kidney, brain, muscle, pancreas, keratinocytes, lymphocytes and HeLa cells (not shown). Nevertheless, the existence of GPBP isoforms produced by canonical mRNA translation initiation (i.e. AK096854) with a $M_r$ similar to that of the noncanonical translation initiation products reported here cannot be excluded.

Figure 6:
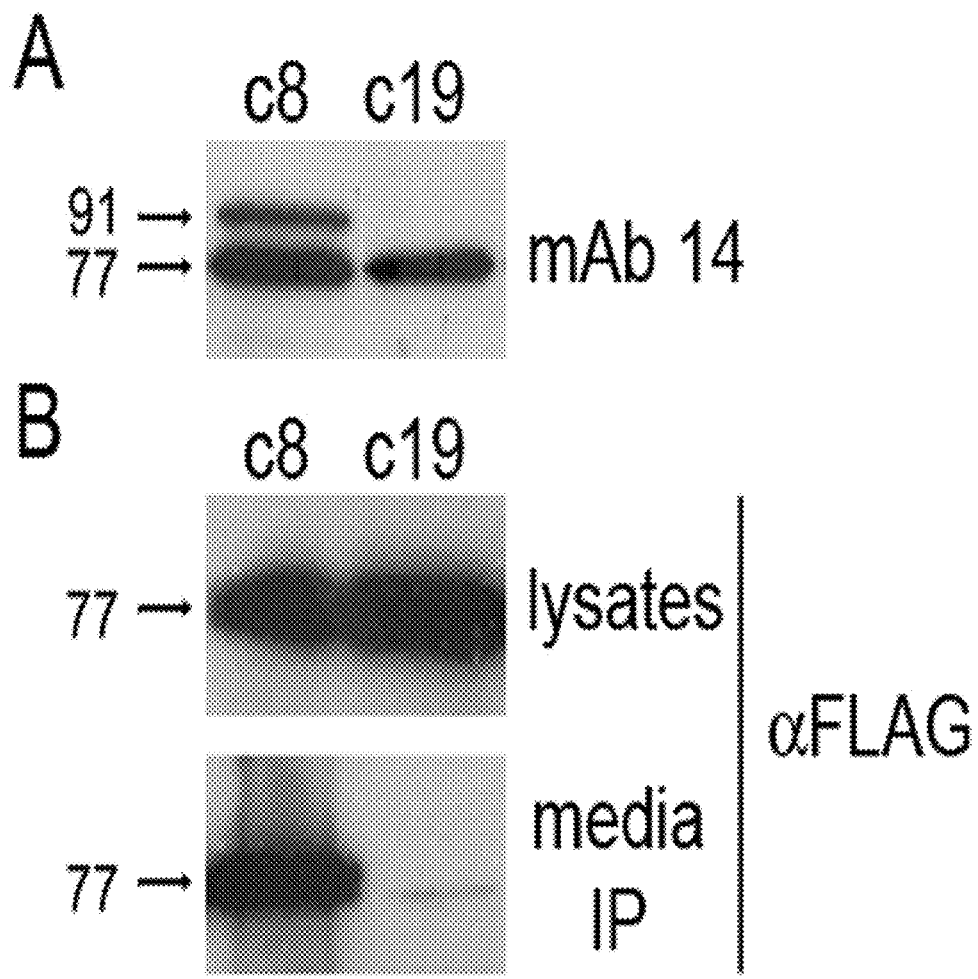
FIG. 6. The 91-kDa GPBP regulates 77-kDa GPBP secretion in cultured cells. In A, extracts (10 µg) from two independent clones expressing (c8) or not expressing (c19) recombinant 91-kDa GPBP were analyzed by Western blot with mAb 14 antibodies, which react poorly with native 91-kDa counterpart (FIG. 1B). In B, the same clones were transfected with pc-FLAG-GPBP, and cell extracts (lysates) or FLAG-immunoprecipitates from the corresponding culture media (media IP) were analyzed by Western blot using the indicated antibodies. Similar conclusions were obtained when assaying c14, an independent HEK 293 clone expressing levels of recombinant 91-kDa GPBP similar to c8 (not shown).

Primary structure analysis predicts that noncanonically translated GPBP products enter into the secretory pathway. Several observations support these predictions, namely: 1) noncanonical GPBP isoforms are molecular species associated with cellular membranes (FIG. 3); 2) noncanonical GPBP isoforms are the predominant GPBP species in the cell (FIG. 1) and GPBP-specific antibodies bound to the external surface of intact living cells (FIG. 3); 3) 120-kDa polypeptide is not expressed from the mRNA when translation occurs in a cell-free system devoid of cellular membranes (FIG. 2); and 4) 91-kDa GPBP isoform regulates the levels of the 77-kDa GPBP at the extracellular compartment (FIG. 6). Taken together, these observations support the notion that the 91-kDa polypeptide is the primary product of noncanonical translation initiation. This isoform enters into the secretory pathway where undergoes covalent modification to yield the 120-kDa polypeptide and remains bound to membranes reaching the external surface of the plasma membrane. The mechanism by which 91-kDa GPBP regulates the extracellular levels of 77-kDa GPBP remains unknown.

Figure 10:
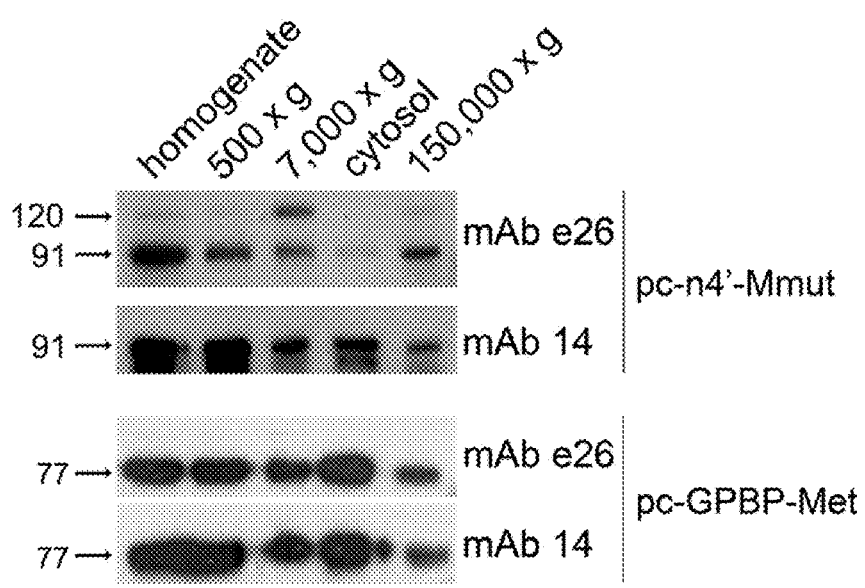
FIG. 10. Recombinant GPBP expression induces accumulation of GPBP polypeptides in the cytosol. Cells were transfected with the indicated plasmid constructs, collected one day after transfection, subjected to fractionation as indicated in Material and Methods in the Example 1 and analyzed by Western blot as in FIG. 3C using the indicated antibodies. Arrows and numbers indicate the position and $M_r$ in kDa of the different GPBP polypeptides. The 120-kDa polypeptide was mainly found in lysosomal fraction and in a more limited amounts in microsomal fraction, further suggesting that it represents a covalently modified-derived version of the 91-kDa generated in the secretory pathway. Additional observations include the comparatively lower reactivity that mAb e26 displays towards the 91-kDa polypeptide that resides in the cytosol (compare mAb e26 with mAb 14 reactivity when the polypeptide resides in cytosol or microsomes −150,000× g).
Figure 11:
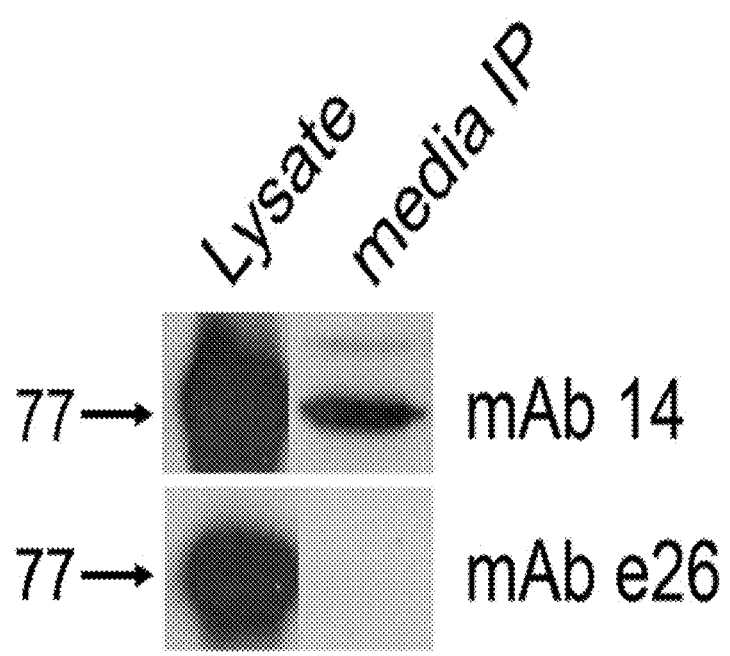
FIG. 11. Extracellular 77-kDa GPBP does not react significantly with mAb e26. Cells transfected with pc-FLAG-GPBP were lysed and the corresponding cultured media subjected to FLAG-immunoprecipitation. Similar amounts of cell extracts (lysate) or immunoprecipitates (media IP) were analyzed by Western blot using the indicated antibodies.

We have observed that when expression is abnormally elevated (i.e. transient gene expression), GPBP polypeptides accumulate in the cytosol (FIG. 10), revealing that GPBP transportation into the ER is a saturable process. Interestingly, under these expression conditions, mAb e26 displayed more reactivity for the cytosolic 77-kDa polypeptide than for this isoform when residing in the extracellular compartment (FIGS. 10 and 11). Moreover, mAb 14 reacted comparatively more with recombinant than with native 91-kDa GPBP and did not react significantly with native or recombinant 120-kDa product (FIG. 1). All these observations suggest that the 26-residue Ser-rich region (mAb e26) and the FFAT motif (mAb 14) are subjected to covalent modifications in the secretory pathway. These data also imply that under specific regulatory (physiological or pathological) circumstances GPBP can be expressed as soluble polypeptides in the cytosol. Finally, it remains to be determined whether 91-kDa GPBPΔ26/CERT is expressed endogenously and whether GPBPΔ26/CERT can be transported into the ER without undergoing secretion.

The expression levels of cytosolic 77-kDa polypeptide representing GPBPΔ26/CERT were significantly reduced in cells expressing GPBP-specific siRNA (FIG. 1D). This suggests that either siRNA is also targeting the pre-mRNA or that the mRNA of GPBP is to some extent a precursor of GPBPΔ26 mRNA. We have found that cells expressing recombinant GPBP also expressed limited amounts of recombinant GPBPΔ26/CERT (unpublished observations). This reveals that mature GPBP mRNA is subjected to a nonclassical processing, similarly to that reported for XBP1 in response to ER stress signals (25). Alternatively, GPBP species bearing covalently modified 26-residue Ser-rich region which co-migrate with GPBPΔ26/CERT could also account for this observation.

Several lines of evidence support that GPBP regulates protein folding in the ER and supramolecular organization in the extracellular compartment rather than inter-organelle ceramide traffic in the cytosol: 1) The 77-kDa GPBP is a nonconventional Ser/Thr kinase that binds and phosphorylates the α3(IV)NC1 domain at sites (1) that are also phosphorylated in vivo (26); 2) The 77-kDa GPBP is mainly found in the extracellular compartment both soluble (FIG. 5 and FIG. 8) or associated with GBM collagen (4), and is not expressed at significant levels in the cytosol of cultured cells (FIGS. 1 and 3); 3) Cellular GPBP isoforms localize at the external surface of the plasma membrane (FIG. 3); 4) The 91-kDa GPBP isoform is associated with cellular membranes (FIG. 3) and regulates the extracellular levels of the 77-kDa GPBP isoform (FIG. 6); 5) The α3(IV)NC1 domain undergoes unique structural diversification and at least two distinct conformational isoforms (conformers) assemble in basement membranes (27); 6) An increased expression of the 77-kDa GPBP perturbs the quaternary structure of type IV collagen, suggesting that the elevated GPBP levels interferes with the conformational diversification program (tertiary structure) of the α3(IV)NC1 domain (4); 7) Increased serum levels of GPBP correlates with type IV-collagen based glomerulonephritis (FIG. 8); 8) The FFAT motif is a structural requirement for 77-kDa GPBP secretion (FIG. 5) and VAP is critical for maintaining the homeostasis for adequate protein folding in the ER (10); 9) Grp78 and Grp94, chaperones which reside in the ER and regulate cellular response to protein misfolding (18, 19), are associated with FLAG-α3(IV) and 77-kDa GPBP (FIG. 4); 10) Increased COL4A3BP expression has been found to mediate resistance of cancer cells to chemotherapeutic agents that induce protein misfolding and ER stress-mediated cell death (28); 11) Treatment of cells with sphingomyelinase does not induce dephosphorylation nor does it alter intracellular distribution of 77-kDa GPBP (FIG. 7); 12) Protein kinase D phosphorylates GPBP but not to the same extent as GPBPΔ26/CERT (6); 13) Knock-down and rescue experiments reveal that GPBP and GPBPΔ26/CERT exert different biological functions during embryogenesis in Zebra fish (29); and 14) GPBP interacts with proteins RTN3 and RTN4 which are anchored from the luminal/extracellular side to the membranes in the secretory pathway (30).

GPBP lacking the 26-residue Ser-rich region also binds to VAP (21, 22); however, ceramide uptake follows binding to VAP and subsequently, the protein departs to the Golgi apparatus where ceramide is released and protein exocytosis induced (6, 14). Therefore, phosphate transfer and ceramide trafficking may be molecular strategies through which COL4A3BP regulates protein secretion (i.e. type IV collagen). Consistent with this, it has been shown that VAP is also critical for regulating protein cargo transport to the plasma membrane (11).

Various lines of evidence support that COL4A3BP is an attractive target for strategies to diagnose and treat antibody-mediated disorders (3, 4), inflammation (15), ER stress-mediated diseases (10) and drug resistant cancer (28). However, observations supporting these conclusions may now need to be re-interpreted since many have been obtained using tools (i.e. siRNA or antibodies) which failed to discriminate between different gene products (i.e. GPBP and GPBPΔ26/CERT), that are expressed at distinct cell compartments, and are differentially regulated in response to stimuli (3). Therefore, the present study makes an important contribution to this understanding by clarifying the mechanisms by which various isoforms of GPBP are generated within the cells.

Furthermore, by identifying circulating human 77-kDa GPBP, we provide compelling evidence that GPBP secretion is also biologically relevant in vivo. The finding that the levels of circulating 77-kDa GPBP correlate with GPBP glomerular expression and pathogenesis in mouse models of immune complex-mediated glomerulonephritis suggests that serological determination of GPBP is relevant in a clinical setting. Consistent with this, present studies demonstrating upregulation of circulating GPBP in Goodpasture patients support these conclusions and substantiate previous observations that GPBP is overexpressed in these patients (3, 31).

These and previous findings support that GPBP promotes type IV collagen secretion and supramolecular organization. Accordingly, GPBP is critical for adequate GBM assembly and abnormal GPBP accumulation induces GBM disruption and deposits of IgA immune complexes (4). To our knowledge, increased GPBP expression, GBM dissociation and deposits of immune complexes are novel mechanisms underlying renal disease. Whether similar mechanisms operate in human pathogenesis remains to be determined; however, ultrastructural evidence for GBM disruption and accumulation of electron-dense material has been reported in patients undergoing IgA nephropathy and lupus nephritis (32, 33). Moreover, increased GPBP expression could reduce the reinforcement of the quaternary structure of type IV collagen, thereby facilitating epitope exposure, immune system activation and autoantibody binding in Goodpasture disease (34). Consistent with the later hypothesis, Goodpasture patients present increased levels of circulating GPBP supporting previous observations that GPBP expression is upregulated in Goodpasture tissues (3, 31). GPBP is a circulating molecule and GBM a principal component of the glomerular filtration barrier; therefore, pathogenic GPBP accumulation in the glomerulus could result from local production but also from the sequestration of circulating GPBP produced elsewhere. The local overproduction could account for primary antibody-mediated glomerulonephritis whereas increased circulating levels may induce secondary forms of this pathology and perhaps are responsible for disease recurrence upon renal transplantation. Consequently, quantification of the levels of circulating GPBP might be useful in discriminating primary from secondary antibody-mediated glomerulonephritis and for the clinical monitoring of renal transplantation.

REFERENCES FOR EXAMPLE 1

1. Raya, A., Revert, F., Navarro, S., and Saus, J. (1999) *J. Biol. Chem.* 274, 12642-12649
2. Hudson, B. G., Tryggvason, K., Sundaramoorthy, M., and Neilson, E. G. (2003) *N. Engl. J. Med.* 348, 2543-2556
3. Raya, A., Revert-Ros, F., Martínez-Martínez, P., Navarro, S., Roselló, E., Vieites, B., Granero, F., Forteza, J., and Saus, J. (2000) *J. Biol. Chem.* 275, 40392-40399
4. Revert, F., Merino, R., Monteagudo, C., Macías, J., Peydró, A., Alcácer, J., Muniesa, P., Marquina, R., Blanco, M., Iglesias, M., Revert-Ros, F., Merino, J., and Saus, J. (2007) *Am. J. Pathol.* 171, 1419-1430
5. Kumagai, K., Kawano, M., Shinkai-Ouchi, F., Nishijima, M., and Hanada, K. (2007) *J. Biol. Chem.* 282, 17758-17766
6. Fugmann, T., Hausser, A., Schöffler, P., Schmid, S., Pfizenmaier, K., and Olayioye, M. A. (2007) *J. Cell Biol.* 178, 15-22
7. Lemmon, M. A., and Ferguson, K. M. (2000) *Biochem J.* 350, 1-18
8. Dowler, S., Currie, R. A., Campbell, D. G., Deak, M., Kular, G., Downes, C. P., and Alessi, D. R. (2000) *Biochem. J.* 351, 19-31
9. Loewen, C. J. R., Roy, A., and Levine, T. P. (2003) *EMBO J.* 22, 2025-2035
10. Kanekura, K., Nishimoto, I., Aiso, S., and Matsuoka, M. (2006) *J. Biol. Chem.* 281, 30223-30233
11. Wyles, J. P., McMaster, C. R., and Ridgway, N. D. (2002) *J. Biol. Chem.* 277, 29908-29918
12. Soccio, R. E. and Breslow, J. L. (2003) *J. Biol. Chem.* 278, 22183-22186
13. Alpy, F., and Tomasetto, C. (2005) *J. Cell Sci.* 118, 2791-2801
14. Hanada, K., Kumagai, K., Yasuda, S., Miura, Y., Kawano, M., Fukasawa, M., and Nishijima, M. (2003) *Nature* 426, 803-809
15. Lamour, N. F., Stahelin, R. V., Wijesinghe, D. S., Maceyka, M., Wang, E., Allegood, J. C., Merrill, A. H. Jr., Cho, W., Chalfant, C. E. (2007) *J. Lipid Res.* 48, 1293-1304
16. Netzer, K. O., Leinonen, A., Boutaud, A., Borza, D. B., Todd, P., Gunwar, S., Langeveld, J. P., and Hudson, B. G. (1999) *J. Biol. Chem.* 274, 11267-11274
17. Granero, F., Revert, F., Revert-Ros, F., Lainez, S., Martinez-Martinez, P., and Saus, J. (2005) *FEBS J.* 272, 5291-5305
18. Bendtsen, D. J., Jensen, J. L., Blom, N., von Heijne, G., and Brunak, S. (2004) *Protein Eng. Des. Sel.* 17, 349-356
19. Yang, Y., and Li, Z. (2005) *Mol. Cells.* 20, 173-182
20. Ni, M., and Lee, A. S. (2007) *FEBS Lett.* 581, 3641-3651
21. Perry, R. J., and Ridgway, N. D. (2006) Mol. Biol. Cell. 17, 2604-2616
22. Kawano, M., Kumagai, K., Nishijima, M., and Hanada, K. (2006) *J. Biol. Chem.* 281, 30279-30288
23. Peabody, D. S. (1989) *J. Biol. Chem.* 264, 5031-5035

24. Touriol, C., Bornes, S., Bonnal, S., Audigier, S., Prats, H., Prats, A. C., and Vagner, S. (2003) *Biol. Cell.* 95, 169-178
25. Yoshida, H., Matsui, T., Yamamoto, A., Okada, T., and Mori, K. (2001) *Cell* 107, 881-891
26. Revert, F., Penadés, J. R., Plana, M., Bernal, D., Johansson, C., Itarte, E., Cervera, J., Wieslander, J., Quinones, S., and Saus, J. (1995) *J. Biol. Chem.* 270, 13254-13261
27. Calvete, J. J., Revert, F., Blanco, M., Cervera, J., Tárrega, C., Sanz, L., Revert-Ros, F., Granero, F., Pérez-Payá, E., Hudson, B. G., and Saus, J. (2006) *Proteomics* 6, S237-S244
28. Swanton, C., Marani, M., Pardo, O., Warne, P. H., Kelly, G., Sahai, E., Elustondo, F., Chang, J., Temple, J., Ahmed, A. A., Brenton, J. D., Downward, J., and Nicke, B. (2007) *Cancer Cell* 11, 498-512
29. Granero-Moltó, F., Sarmah, S., O'Rear, L., Spagnoli, A., Abrahamson, D., Saus, J., Hudson, B. G., and Knapik, E. W. (2008) *J. Biol. Chem.* April 18. [Epub ahead of print]
30. Rual, J. F., Venkatesan, K., Hao, T., Hirozane-Kishikawa, T., Dricot, A., Li, N., Berriz, G. F., Gibbons, F. D., Dreze, M., Ayivi-Guedehoussou, N., Klitgord, N., Simon, C., Boxem, M., Milstein, S., Rosenberg, J., Goldberg, D. S., Zhang, L. V., Wong, S. L., Franklin, G., Li, S., Albala, J. S., Lim, J., Fraughton, C., Llamosas, E., Cevik, S., Bex, C., Lamesch, P., Sikorski, R. S., Vandenhaute, J., Zoghbi, H. Y., Smolyar, A., Bosak, S., Sequerra, R., Doucette-Stamm, L., Cusick, M. E., Hill, D. E., Roth, F. P., and Vidal, M. (2005) *Nature* 437, 1173-1178
31. Saus, J (2002) "Methods and reagents for treating autoimmune disorders" Utility Patent Application serial n PCT/EP02/01010. Publication no WO 02/061430
32. Haas M. "IgA Nephropathy and Henoch-Schönlein Purpura Nephritis". Heptinstall's Pathology of the Kidney. Edited by Jennette J C, Olson J L, Schwartz M M, Silva F G. Philadelphia, Lippincott Williams & Wilkins Publishers 2007, pp. 423-486
33. Balow, J. E., Boumpas, D. T., and Austin III, H. A. "Systemic Lupus Erythematosus and the kidney". Systemic Lupus Erythematosus. Edited by Lahita R G. San Diego, Academic Press, 1999, pp. 657-685
34. Borza, D. B., Bondar, O., Colon, S., Todd, P., Sado, Y., Neilson, E. G., and Hudson, B. G. (2005) *J. Biol. Chem.* 280, 27147-27154

Abbreviations

The abbreviations used are: α3(IV)NC1, the NC1 domain of the α3 chain of type IV collagen; ATR, alternative translated region; CERT and CERT$_L$, short and large isoforms of the ceramide transfer protein; COL4A3BP, the gene encoding for GPBP (CERT$_L$) and GPBPΔ26 (CERT) which was named collagen IV α3-binding protein; EDTA, ethylenediaminetetraacetic acid; ER, endoplasmic reticulum; FFAT, two phenylalanines in an acidic track; GBM, glomerular basement membrane; GPBP and GPBPΔ26, large and short alternatively spliced variants of the Goodpasture antigen-binding protein; HRP, horseradish peroxidase; mAb, monoclonal antibody; NC1, noncollagenous-1 domain; ORF, open reading frame; NZW, new Zealand white; PBS, phosphate buffered-saline; PH, pleckstrin homology; RT, room temperature; SDS-PAGE, sodium dodecyl sulfate-polyacrylamide gel electrophoresis; START, steroidogenic acute regulatory related lipid transfer; UTR, untranslated region; VAP, vesicle associated membrane protein-associated protein.

EXAMPLE 2

Identification and Isolation of GPBP from Human Plasma

Here we used classical chemical procedures for protein fractionation of human plasma and identified multiple tertiary and quaternary GPBP structures circulating in human plasma. The data also show that 77-kDa GPBP and derived species of lower MW are the major GPBP circulating isoform(s) as determined by reconstitution of plasma conditions from isolated partially purified-GPBP quaternary structures.

Materials and Methods

GPBP was purified from 50 ml of frozen control plasma using a combination of salting-out precipitation, ion exchange chromatography and gel filtration.

Proteins precipitated by freezing were first removed by plasma centrifugation at 8200×g for 10 min at 4° C. Since the specific properties for purification of plasma GPBP are not known, proteins were sequentially precipitated from the original sample with growing (NH$_4$)$_2$SO$_4$ saturations (20%, 40%, 60% and 80%). Sequential precipitations were performed by centrifugation at 8200×g for 10 min at 4° C. and precipitates were dissolved in 5 ml of 50 mM Tris-HCl, pH 7.5. Protein mixtures were desalted by dialysis against 50 mM Tris-HCl, pH 7.5 using membrane bags with 3.5-kDa cut-off. The final supernatant of (NH$_4$)$_2$SO$_4$ precipitations was similarly dialyzed and further used for purification as the final fraction yielded by the precipitation process.

The fractions rendered by the salting-out were subsequently analyzed by ion exchange chromatography (IEC) using a HiTrap Q-sepharose anion exchange column. The column was first equilibrated with buffer A (50 mM Tris/HCl, pH 7.5, 20 mM NaCl), further loaded with each individual sample and washed with 10 volumes of buffer A. Bound proteins were eluted with a gradient from buffer A to buffer B (50 mM Tris/HCl, pH 7.5, 1 M NaCl) and collected in 0.6 ml fractions. IEC fractions containing GPBP material were detected by Western blot with GPBP-specific biotinylated N27 monoclonal antibody. GPBP-containing IEC fractions were pooled, concentrated to 0.5 ml, and subsequently subjected to gel filtration chromatography with Superdex™ 200 10/300 CL. In this process, the column was first equilibrated with TBS (50 mM Tris/HCl pH 7.5, 150 mM NaCl), the sample was injected into the column and proteins separated by size. The gel filtration fractions were analysed by Western blot for detection of GPBP material with biotinylated N27 monoclonal antibody. The fractions containing GPBP were pooled, precipitated with 80% acetone and resuspended in 50 mM Tris-HCl pH 7.5, 8M urea. The resulting mixtures, each one corresponding to a different initial fraction rendered by sequential (NH$_4$)$_2$SO$_4$ precipitation were pooled in equal proportions in order to faithfully reconstitute the native plasma protein composition. A sample of the final pool was subjected to Western blot with HRP-labelled N27 monoclonal antibody.

Results

Figure 12:
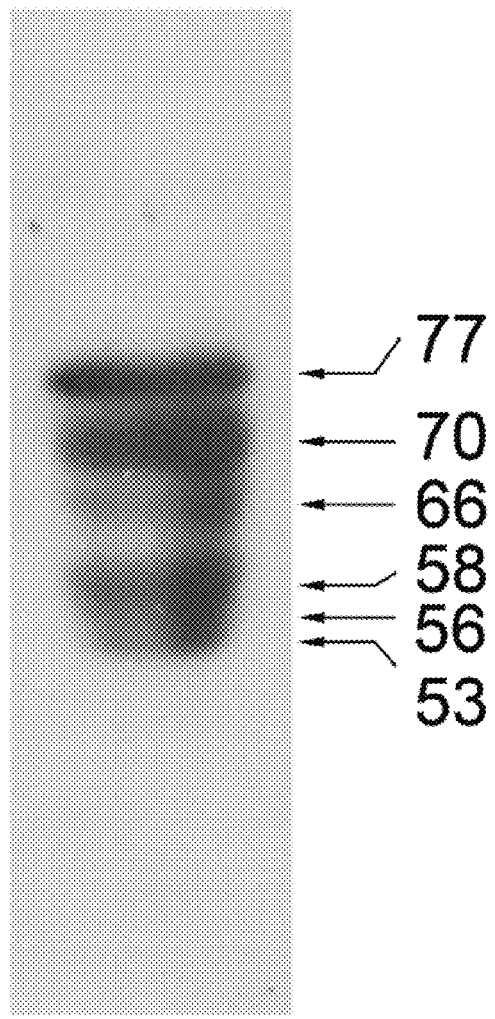
FIG. 12: Western blot analysis of GPBP isolated from plasma samples using chemical techniques. The GPBP partially purified from approximately 1.25 mL of human plasma (see Example 2) was analyzed by Western blot under reducing conditions using HRP-labeled mAb N 27. Arrows and numbers indicated the position and the estimated $M_r$ for reactive polypeptides.

In the resulting Western blot we observed major GPBP isoforms of 77-, 70-, 66-, 58-, 56- and 53-kDa. There exist additional polypeptides not represented in significant amounts in the Western blot in FIG. 12 that were identified in Western blot analysis performed during the purification process. These included polypeptides of approximately: 368-kDa [20% (NH$_4$)$_2$SO$_4$], 40-, 110-, 120- and 311-kDa [40% (NH$_4$)$_2$SO$_4$], and 91-, 146-, 171- and 300-kDa polypeptides [60% (NH$_4$)$_2$SO$_4$] (data not shown). Finally, the size of each chromatographic peak in gel filtration analysis, which represented individual GPBP quaternary structures was also estimated. Specifically, we found GPBP aggregates of: 1400- and 920-kDa in 20% (NH$_4$)$_2$SO$_4$ precipitate; 310- and 145-kDa in 40% (NH$_4$)$_2$SO$_4$ precipitate; 920-, 420-, 270-, and 125-kDa in 60% (NH$_4$)$_2$SO$_4$ precipitate; 66-kDa in the 80% (NH$_4$)$_2$SO$_4$ precipitate; and, 91-kDa in a soluble form at 80% (NH$_4$)$_2$SO$_4$ saturation.

Conclusions
1. There exist multiple circulating GPBP isoforms which are assembled in a number of different quaternary structures.
2. The major circulating GPBP isoform includes the previously recognized 77-kDa and derived polypeptides of lower $M_r$.

EXAMPLE 3

GPBP Isolation and Quantification from Human Urine

Here we demonstrate that GPBP is a normal component of the urine which can be both measured by simple immunological-based procedures (i.e. ELISA) and isolated by chemical and immunochemical procedures. The evidence indicates that 91-kDa polypeptide and derived polypeptides are the major urinary GPBP products.
Isolation of Urinary GPBP by Immunoaffinity Chromatography.

Figure 13:
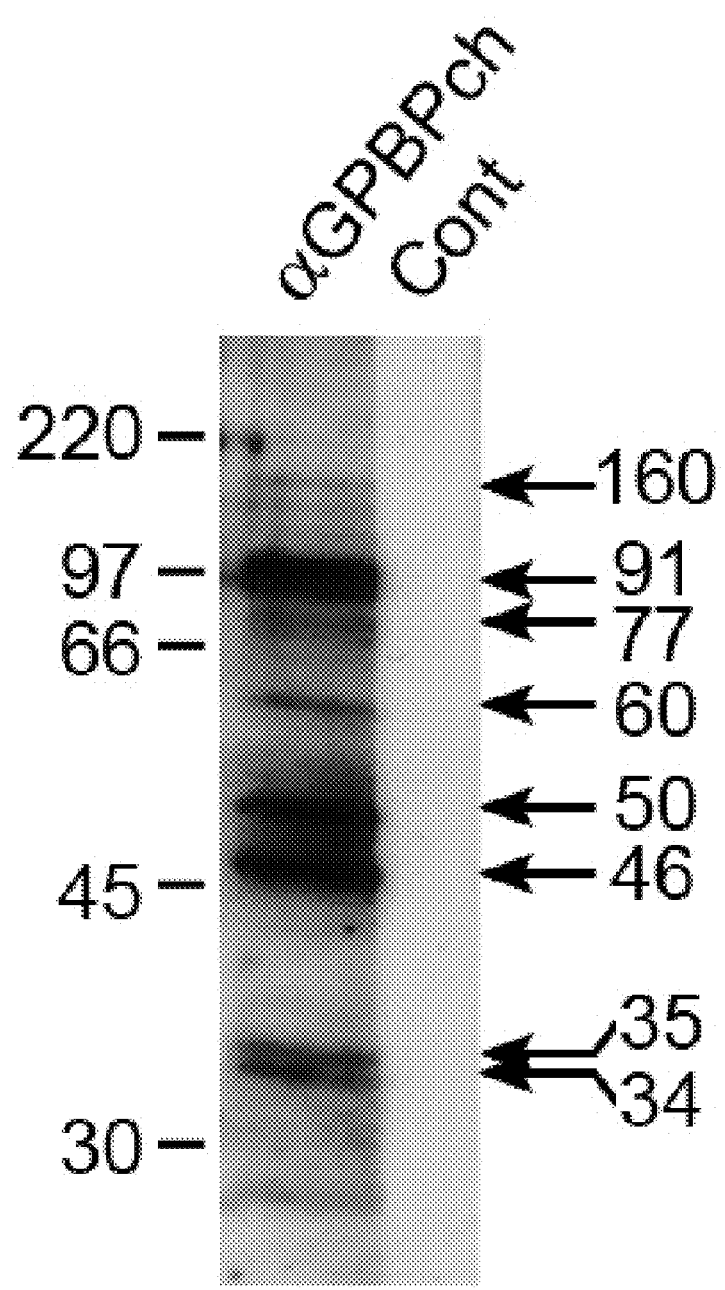
FIG. 13. GPBP isolated from urine of a control donor using immunoaffinity chromatography. Two hundred and fifty milliliters of urine from a control donor (previously cleared by centrifugation and neutralized with Tris), were loaded onto a 1 mL column of Sepharose 4B-conjugated with 200 µg of rabbit polyclonal anti-GPBP antibodies. The column was washed with 30 mL of TBS and the bound material was eluted with Gentle Immunopure™ Elution Buffer (Pierce). The material eluted was dialyzed against TBS and further analyzed by Western blot using GPBP-specific chicken polyclonal antibodies (αGPBPch) and HRP-labelled anti-chicken IgY (secondary antibody). Antibody specificity was confirmed by staining a control lane loaded with the same material with secondary antibody (Cont). Bars and numbers or arrows and numbers indicate the position and size (kDa) of MW standards (left) or GPBP polypeptides (right), respectively.

GPBP was extracted from urine of a control donor using Sepharose 4B loaded with GPBP-specific rabbit polyclonal antibodies. The column-bound material was eluted and analyzed by Western blot using GPBP-specific chicken polyclonal antibodies (FIG. 13). A number of polypeptides displaying a broad range of MW were detected with GPBP-specific antibodies in the immunoaffinity purified sample. A 91-kDa polypeptide, along with other derived polypeptides of lower MW (46- and 50-kDa) [Juan Saus, Fernando Revert and Francisco Revert-Ros "Novel Goodpasture antigen-binding protein isoforms and protein misfolded-mediated disorders" PCT/EP04/01074 y WO 2004/070025], was found to be the most abundant GPBP material in the human urine.

Figure 14:
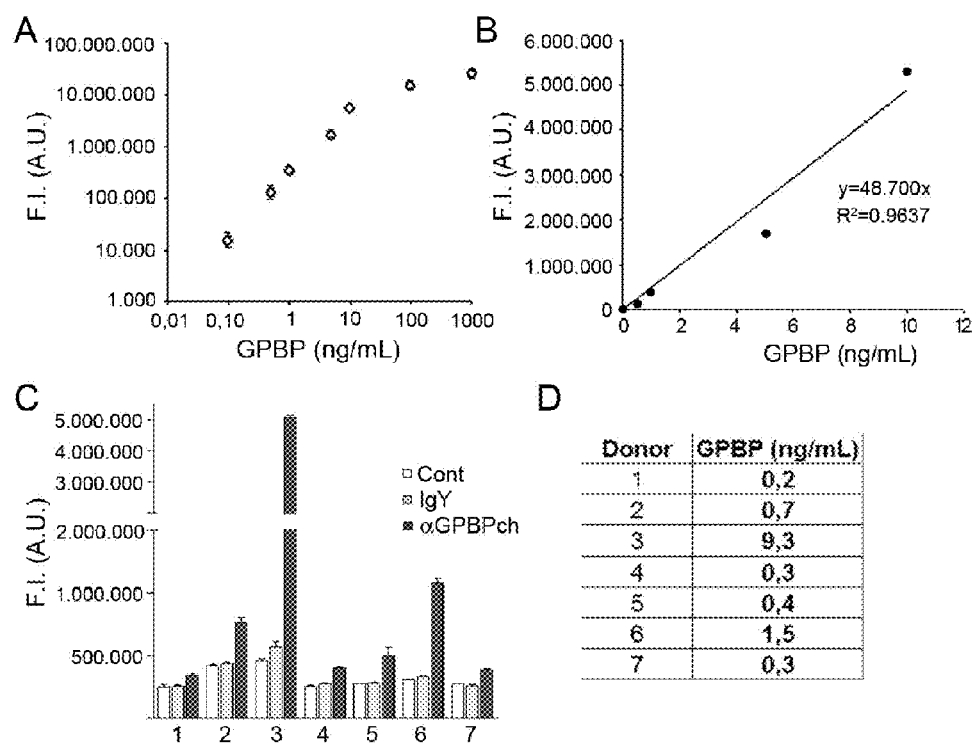
FIG. 14. Indirect ELISA to detect GPBP in urine samples. Recombinant GPBP diluted in urine and urine samples from seven donors (1-7) were coated onto ELISA plates overnight at 40° C. Plates were blocked with 3% BSA in PBS and immunodetection performed with GPBP-specific chicken polyclonal antibodies (αGPBPch) and HRP-labelled anti-chicken IgY (secondary antibody). Amplex UltraRed reagent (Invitrogen) was used for developing the plate. In A, is represented a scatter plot on a log-log scale of the indicated concentrations of GPBP versus fluorescence intensity (F.I.) expressed in arbitrary units (A.U.). In B, is represented the linear regression line calculated with the indicated concentrations and their respective F.I. values plotted on linear scale, that was used to determine GPBP sample concentration in D. In C, is represented raw data obtained analyzing donor samples with: secondary antibody (Cont), nonspecific chicken IgY and secondary antibody (IgY), or with αGPBPch and secondary antibody (αGPBPch). In D, the table shows corresponding transformed data using the curve obtained in B.

Specifically, two hundred and fifty milliliters of urine from a control donor (previously cleared by centrifugation and neutralized with Tris), were loaded onto a 1 mL column of Sepharose 4B-conjugated with 200 µg of rabbit polyclonal anti-GPBP antibodies. The column was washed with 30 mL of TBS and the bound material was eluted with Gentle Immunopure Elution Buffer (Pierce). The material eluted was dialyzed against TBS and further analyzed by Western blot using GPBP-specific chicken polyclonal antibodies (αGPBPch) and HRP-labelled anti-chicken IgY (secondary antibody) (FIG. 13). Antibody specificity was confirmed by staining a control lane loaded with the same material with secondary antibody (Cont). Bars and numbers or arrows and numbers indicate the position and size (kDa) of MW standards (left) or GPBP polypeptides (right), respectively
Measurement of Urinary GPBP by ELISA Since the concentration of protein in urine is low (normally lower than 80 ug/mL), indirect ELISA was attempted with samples from seven donors. For these purposes, plates were coated with urine samples and immunodetection performed using GPBP-specific chicken polyclonal antibodies and HRP-labelled anti-chicken IgY (secondary antibody). A standard curve was similarly obtained using human recombinant GPBP diluted in human urine. GPBP was detected in all donors and individual concentrations were determined by subtracting the background (F.I. measured using unspecific IgY) in each case (FIG. 14). All donors showed detectable levels of GPBP and donor 3 displayed an abnormally elevated GPBP concentration in urine.

Specifically, recombinant GPBP diluted in urine and urine samples from seven donors (1-7) were coated onto ELISA plates overnight at 4° C. Plates were blocked with 3% BSA in PBS and immunodetection performed with GPBP-specific chicken polyclonal antibodies (αGPBPch) and HRP-labelled anti-chicken IgY (secondary antibody). Amplex UltraRed reagent (Invitrogen) was used for developing the plate. (FIG. 14) In A, is represented a scatter plot on a log-log scale of the indicated concentrations of GPBP versus fluorescence intensity (F.I.) expressed in arbitrary units (A.U.). In B, is represented the linear regression line calculated with the indicated concentrations and their respective F.I. values plotted on linear scale, that was used to determine GPBP sample concentration in D. In C, is represented raw data obtained analyzing donor samples with: secondary antibody (Cont), nonspecific chicken IgY and secondary antibody (IgY), or with αGPBPch and secondary antibody (αGPBPch). In D, the table shows corresponding transformed data using the curve obtained in B.

We obtained similar concentration values when GPBP was determined on TBS-diluted urine using the sandwich ELISA procedure used for serum/plasma samples (data not shown).
Urinary GPBP Isolation by Salt Precipitation and Ion Exchange Chromatography.

Figure 15:
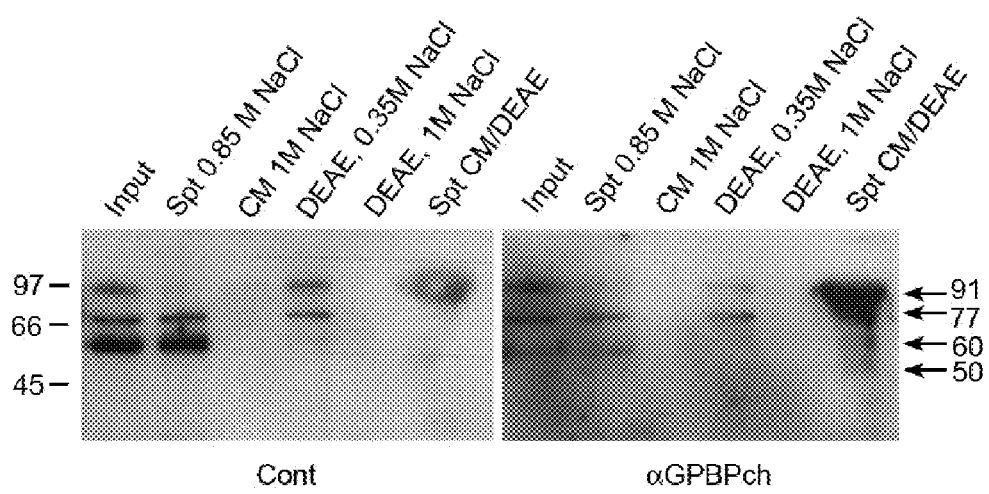
FIG. 15. Salting-out and ion exchange chromatography of urine samples. Four hundred milliliters of urine cleared by centrifugation was brought to 0.85 M NaCl overnight at 4° C., and subjected to centrifugation at 10.000×g for 30 min at 4° C. A sample of the supernatant (Spt 0.85 M NaCl) was stored at 4° C. to be included in the subsequent analysis. The resulting pellet was dissolved in 50 mM Tris pH 7.5, dialyzed against the same buffer, extracted with 0.7 mL of CM resin and unbound material further extracted with 0.5 mL of DEAE resin. CM resin was eluted with 1M NaCl, 50 mM Tris pH 7.5 (CM, 1M NaCl), and DEAE resin was subsequently eluted with 0.35M NaCl, 50 mM Tris pH 7.5 (DEAE, 0.35M NaCl) and 1M NaCl, 50 mM Tris pH 7.5 (DEAE, 1M NaCl). Equivalent amounts of each sample including the supernatant of the DEAE extraction (Spt CM/DEAE) were analyzed by Western blot with GPBP-specific chicken polyclonal antibodies and HRP-labelled anti-chicken IgY (αGPBPch). Nonspecific reactive polypeptides were identified by staining an in-parallel analysis using only HRP-labelled anti-chicken IgY (Cont). Bars and numbers or arrows and numbers indicate the position and size (kDa) of MW standards (left) or polypeptides specifically reacting with anti-GPBP antibodies and that were detected only in SptCM/DEAE (right), respectively.

To validate immunoaffinity and ELISA procedures and to determine which GPBP species increased in donor 3, we attempt GPBP purification from this urine using classical chemical purification procedures. These included, salt precipitation and double ion-exchange chromatography [carboxymethyl-cellulose (CM) and diethylaminoethyl-cellulose (DEAE)], and Western blot analysis of the different materials representing each purification step (FIG. 15). Western blot analysis using GPBP-specific chicken polyclonal antibodies revealed that most of GPBP material was precipitated by salt and did not bound to either CM or DEAE. A major GPBP polypeptide of 91-kDa was detected along with significant amounts of GPBP polypeptide of 77-kDa and only traces of GPBP-related polypeptides of 60- and 50-kDa.

To validate immunoaffinity and ELISA procedures and to determine which GPBP species increased in donor 3, we attempted GPBP purification from this urine using classical chemical purification procedures. Four hundred milliliters of urine cleared by centrifugation was brought to 0.85 M NaCl overnight at 4° C., and subjected to centrifugation at 10.000×g for 30 min at 4° C. A sample of the supernatant (Spt 0.85 M NaCl) was stored at 4° C. to be included in the subsequent analysis. The resulting pellet was dissolved in 50 mM Tris pH 7.5, dialyzed against the same buffer, extracted with 0.7 mL of CM resin and unbound material further extracted with 0.5 mL of DEAE resin. CM resin was eluted with 1M NaCl, 50 mM Tris pH 7.5 (CM, 1M NaCl), and DEAE resin was subsequently eluted with 0.35M NaCl, 50 mM Tris pH 7.5 (DEAE, 0.35M NaCl) and 1M NaCl, 50 mM Tris pH 7.5 (DEAE, 1M NaCl). Equivalent amounts of each sample including the supernatant of the DEAE extraction (Spt CM/DEAE) were analyzed by Western blot with GPBP-specific chicken polyclonal antibodies and HRP-labelled anti-chicken IgY (αGPBPch). Nonspecific reactive polypeptides were identified by staining an in-parallel analysis using only HRP-labelled anti-chicken IgY (Cont). Bars and numbers or arrows and numbers indicate the position and size (kDa) of MW standards (left) or polypeptides specifically reacting with anti-GPBP antibodies and that were detected only in SptCM/DEAE (right), respectively. (FIG. 15). Western blot analysis using GPBP-specific chicken polyclonal antibodies revealed that most of GPBP material was precipitated by salt and did not bound to either CM or DEAE. A major GPBP polypeptide of 91-kDa was detected along with significant amounts of GPBP polypeptide of 77-kDa and only traces of GPBP-related polypeptides of 60- and 50-kDa.

Conclusions
1) GPBP polypeptides can be isolated from urine either by affinity chromatography or by salting-out precipitation followed by ion-exchange chromatography.
2) GPBP levels in urine can be assessed either by indirect ELISA or sandwich ELISA using specific anti-GPBP antibodies.
3) The major GPBP polypeptide found in urine displays 91-kDa.

EXAMPLE 4

Production and Characterization of Monoclonal Antibodies Targeting GPBP

Previously reported mAb14 and mAb e26 epitopes in GPBP are subjected to posttranslational modifications during secretion (Revert et al. 2008 *J. Biol. Chem.* 283:30246-55). Accordingly, these monoclonal antibodies did not significantly react with circulating GPBP isoforms present in human plasma. This recommended the use of polyclonal antibody-based immunological procedures for the isolation and estimation of GPBP circulating levels in human plasma (see Example 1). Here we report the production and characterization of novel GPBP-specific monoclonal antibodies for immunological detection of GPBP in plasma which are more reliable than the polyclonal antibody-based strategy.

Propagation and cryopreservation of hybridomas producing new monoclonal antibodies against GPBP. Using indirect ELISA and recombinant GPBP made in yeast, we have obtained and isolated 28 independent hybridoma clones (N1-N28) which produced anti-GPBP monoclonal antibodies. The clones were expanded in Dulbecco's Modified Eagle's Medium (DMEM) supplemented with 20% fetal bovine serum (FBS), frozen in 10% DMSO in FBS and stored in liquid nitrogen. Before storage, 10 mL of culture medium from each clone were collected stored at 4° C. with 0.01% sodium azide and used for further antibody characterization (see below).

Figure 16:
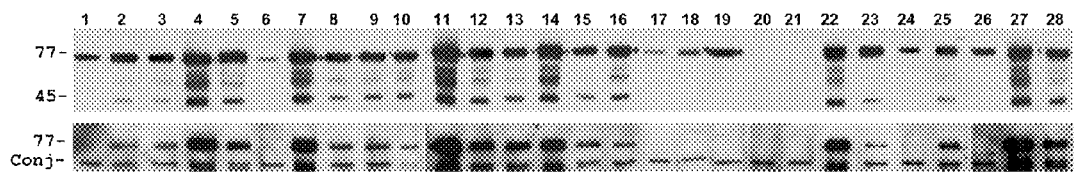
FIG. 16. Western blot analysis of intracellular and extracellular FLAG-GPBP produced in HEK 293 cells using individual N1-N28 monoclonal antibodies. At the upper composite, 10 μg of total protein extract from HEK 293 cells expressing recombinant FLAG-GPBP were subjected to Western blot analysis using N1-N28 antibodies (1-28). A major polypeptide of ~77-kDa representing the full length recombinant GPBP polypeptide and variable presence of derived polypeptides of lower $M_r$ (45-77 kDa) were observed. At the lower composite, the same antibodies were assayed against extracellular recombinant GPBP (77-kDa polypeptide) purified by anti-FLAG immunoprecipitation from the culture media of FLAG-GPBP expressing HEK293 cells (Revert et al. 2008 *J. Biol. Chem.* 283:30246-55). A major polypeptide ~77-kDa representing the full length FLAG-GPBP polypeptide was detected along with a minor nonspecific polypeptide of lower $M_r$ (Conj), which reacted with the secondary antibody (anti-mouse IgG) and is suspected to represent derived products from the immunoprecipitating antibody (mouse anti-FLAG IgG) (not shown). Unless otherwise indicated, in this and subsequent Western blots, 1-28 is N1-N28, and anti-mouse-HRP and chemiluminescence were used for developing purposes.

Western blot characterization of new monoclonal antibodies using recombinant and native GPBP isoforms expressed in HEK 293 cells. The antibodies from each of the 28 hybridomas reacted with recombinant GPBP (25 ng) produced in *E. coli* (data not shown). Except for N20 and N21, all the rest of antibodies also reacted with intracellular recombinant GPBP (FIG. 16). Eleven monoclonal antibodies (N4, N5, N7, N11, N12, N13, N14, N22, N25, N27 and N28) recognized in a similar fashion both, intracellular and extracellular recombinant GPBP. Seven antibodies (N1, N6, N17, N18, N19, N24 and N26) target intracellular but not extracellular GPBP, while the remaining antibodies (N2, N3, N8, N9, N10, N15, N16 and N23) displayed relatively low reactivity with extracellular recombinant GPBP (FIG. 16).

Figure 17:
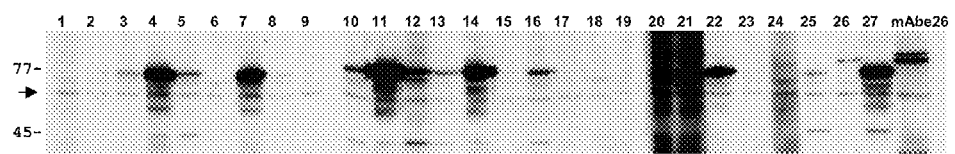
FIG. 17. Western blot analysis of HEK 293 cell extracts using N1-N27 monoclonal antibodies. Fifty μg of HEK 293 cell extract were analysed by Western blot using the indicated antibodies. The antibodies recognized four distinct GPBP-related polypeptides: the 77-kDa canonical polypeptide, a 45-kDa fragment, an 88-kDa band, and a 91-kDa polypeptide also targeted by mAb e26. The polypeptide pinpointed by the arrow was recognized by the secondary antibody (anti-mouse IgG HRP-labelled) and therefore does not represents a GPBP product. The origin of 88-kDa polypeptide is unknown although its $M_r$ suggest that it represents a phosphorylated version of the 77-kDa canonical polypeptide.

Using protein extracts from HEK 293 cells, we have determined that 18 monoclonal antibodies [N2, N3, N4, N5, N7, N8, N9, N10, N11, N12, N13, N14, N15, N16, N22, N25, N27 (shown) and N28 (not shown)] recognized native intracellular 77-kDa GPBP isoforms. Eleven out of these 18 antibodies [N4, N5, N10, N11, N12, N13, N14, N16, N25, N27 (shown) not N28 (not shown)] also targeted a 45-kDa GPBP isoform previously reported to exist in the cells [Juan Saus, Fernando Revert and Francisco Revert-Ros "Novel Goodpasture antigen-binding protein isoforms and protein misfolded-mediated disorders" WO 2004/070025]. The antibodies N4, N7, N11, N14 and N27 also recognized an additional GPBP-related polypeptide of 88-kDa, which may represent a phosphorylated version of the 77-kDa canonical polypeptide (Raya et al 1999 *J. Biol Chem.* 274, 12642-12649). The N26 antibody recognizes a 91-kDa polypeptide which co-migrated with the recently characterized 91-kDa GPBP isoform (Revert et al. 2008 *J. Biol. Chem.* 283:30246-55) targeted by mAb e26 (FIG. 17). The relative efficiencies of the new monoclonal antibodies for detection of GPBP isoforms (native or recombinant) have been estimated and summarized in Table 2.

Epitope mapping for N1-N28 monoclonal antibodies. For these purposes, we produced thirteen different cDNA constructs representing individual C-terminal deletion mutants of GPBP (FIG. 18A). The individual constructs were used for HEK 293 cell transfection and the corresponding cell extracts analyzed by Western blot to assess individual antibody binding. Seventeen out of the 28 new monoclonal antibodies recognized deletion mutant 8 but failed to recognize mutant 7 (Table 1); the rest of the antibodies either target the N terminal end, or the epitope was not determined because of lack of reactivity in Western blot assays. Since the majority of the antibodies reacted with deletion mutant 8 and failed to react with deletion mutant 7, we further attempted individual epitope mapping using synthetic peptides representing the sequence comprised by between C terminal ends of deletion mutant 7 and 8. Strikingly, we failed confirming reactivity of the antibodies versus these 40-residues and also these peptides could not compete GPBP antibody binding. Data suggested that existed a region that was highly immunogenic that required GPBP N terminal region for adequate epitope assembly. This was investigated by producing FLAG-GPBP internal deletion mutants (Δ1-Δ4), in which only the indicated individual 20-residue sequences were removed (FIG. 18B). Deletion mutants Δ1-Δ4 were obtained by standard procedures using two consecutive PCRs and specific primers to introduce the corresponding deletions (FIG. 18B). Interestingly, all the antibodies failed to react with Δ2 and Δ3 internal deletion FLAG-GPBP mutants but reacted with Δ1 and Δ4 mutants (FIG. 18C). Data indicate that the sequence represented by residues 305-344 of GPBP (GGPDYEEGP-NSLINEEEFFDAVEAALDRQDKIEEQ SQSEK, SEQ ID NO:10) conforms a highly immunogenic epitope cluster. Consistently, previously characterized mAb 14 was found to react with this region at the FATT motif (Revert et al. 2008 *J. Biol. Chem.* 283:30246-55).

Classification of the monoclonal antibodies. This has been performed taking into consideration epitope mapping and reactivity with either native or recombinant intracellular or extracellular GPBP isoforms in Western blot analysis (Table 1).

TABLE 1

Classification of the 28 monoclonal antibodies.

|  |  |  | Western blot reactivity with GPBP | | | | | |
|---|---|---|---|---|---|---|---|---|
|  |  | Monoclonal | Recombinant (77-kDa) | | Native (kDa) | | | |
| Region | Group | No. | lysate | medium | 91 | 88 | 77 | 45 |
| 7-8 | 1a | 4, 11, 14, 27 | +++ | +++ | − | + | +++ | ++/+ |
|  | 1b | 7, 22 (~mAb14) | +++ | +++ | − | +$_{(7)/-(22)}$ | +++ | − |
|  | 2 | 5, 10, 12, 13, 16, 25, 28 | +++ | ++/ ±$_{(10,15,16)}$ | − | − | ++$_{(5,10,12)}$/+ | ++ |
|  | 3 | 2, 3, 8, 9 | ++ | ± | − | − | +/± | ±/− |
| <7 | 4 | 15, 23 | ++ | + | − | − | ± | − |
| <4 | 5 | 1, 18, 19, 24, 26 | ++ | − | +$_{(26)}$ | − | − | − |
| ? | 6 | 6, 17 | +/± | − | − | − | − | ±/− |
| ? | 7 | 20, 21 | ±$_{(b)}$/− | − | Several polypeptides are targeted | | | |

The numbers in the "Region" field refer to the different deletion mutants used in the analysis (see FIG. 18, upper composite). For example, Region 7-8 indicates that the antibodies recognize mutant 8 but not mutant 7, and Region <7 means the epitope is N terminal respect to the C terminus of mutant 7.

Characterization of N1-N28 monoclonal antibodies by indirect immunofluorescence analysis of HeLa cells expressing recombinant GPBP. HeLa cells were transfected with pcDNA3-FLAG-GPBP, cultured for 24 additional hours, and fixed with methanol/acetone (50%-50%). After fixation, cells were blocked with 3% BSA in PBS (blocking solution) and incubated with the indicated antibodies (cultured media) diluted 1:2 in blocking solution. Subsequently, cells were washed with PBS and incubated with FITC-labeled anti-mouse IgG, washed again, mounted and observed with an inverted fluorescence microscope. Images were acquired with a 40× objective using identical exposition times and gains. Except N6, all antibodies recognized FLAG-GPBP expressed in HeLa cells with different reactivity, being the most reactive antibodies for this purposes N13, N14, N15, N16, N21, N22 and N26 (see Table 2 for relative detection efficiencies). Among reactive antibodies, all except N28 unveiled the GPBP-characteristic reticular distribution pattern, consequence of the localization of GPBP at the endoplasmic reticulum (Revert et al. 2008 *J. Biol. Chem.* 283: 30246-55).

Characterization of N1-N28 monoclonal antibodies by indirect immunofluorescence analysis of HeLa cells. HeLa cells were seeded and cultured on crystal slides, processed as above, and analyzed with an inverted fluorescence microscope using a 40× objective and an image amplification of 1.63. Except N26, all antibodies showed endoplasmic reticulum distribution similar to that yielded by antibody N27 shown at the left of the composite. Some cells showed also a peri-nuclear and focal reinforcements typical of the Golgi apparatus (white arrow). The pattern unveiled by N26 mixes the previously described reticular distribution with nuclear and peri-nuclear punctuate clusters, and linear decoration of plasma membrane. Except N26, all antibodies exclusively unveiled the endoplasmic reticulum distribution described for recombinant GPBP polypeptide. Antibody N26, apart from yielding a reticular pattern, decorated the plasma membrane and evidenced punctuate peri-nuclear and nuclear accumulations. The best antibodies for detecting endogenous GPBP materials in HeLa cells were N5, N12, N16, N21, N26 and N27 (see Table 2).

Characterization of N1-N28 monoclonal antibodies by immunohistochemical analysis of paraffin-embedded human kidney tissue. Individual monoclonal antibodies were used for standard immunohistochemical analysis of paraffin-embedded human kidney samples. All the reactive antibodies stained mainly convoluted and collecting tubules with significant staining also within glomeruli at mesangial cells, podocytes, mesangial matrix and capillary walls. In the later case with a linear pattern at the endothelium surface and with a granular-like distribution within the capillary wall. In capillary walls, immunostaining was less frequent, being N5, N6, N7, N8, N10 and N26 the best antibodies for these purposes. The antibodies rendering better GPBP detection using immunohistochemical techniques were N5, N6, N7, N8, N9, N10, N12, N26 and N27 (see Table 2).

Assessment of the ability of N1-N28 monoclonal antibodies to capture GPBP in a sandwich ELISA assay. In order to select individual antibodies for sandwich ELISA assays, an ELISA plate previously coated with anti-mouse antibody was used to bind monoclonal antibodies from culture media and their ability to capture recombinant and native GPBP assessed. Anti-mouse-coated ELISA plates were loaded with the culture medium from the hybridomas of the indicated antibodies or with the culture medium from an anti-GAPDH hybridoma (cont). Subsequently, the plate was blocked with 3% BSA in PBS and incubated with recombinant GPBP diluted in FBS at the indicated concentrations, or with FBS (blank). Bound GPBP was detected with chicken polyclonal anti-GPBP and HRP-labelled anti-chicken IgY. Development was performed with a fluorescent reagent (Amplex).

a) Capture assays for human recombinant GPBP. All antibodies efficiently captured FLAG-GPBP, with N5, N6, N8, N10, N11, N12, N15, N16, N20, N23, N26, N27 and N28, displaying the best efficiency capturing FLAG-GPBP from FBS containing 10 ng/ml FLAG-GPBP (Table 2)

b) Capture assays for human circulating GPBP (plasma). Anti-mouse-coated ELISA plates were loaded and blocked as above indicated and further incubated with a Goodpasture patient human plasma (register no. M049) diluted 1:10 in FBS or with FBS alone (blank). Nine out of the 28 antibodies (N3, N5, N9, N10, N11, N12, N13, N26 and N27) efficiently captured efficiently GPBP from human plasma (Table 2).

CONCLUSION

We provide new monoclonal antibodies for native GPBP detection by ELISA, immunofluorescence and immunohistochemical procedures.

TABLE 2

Summary of the relative efficiency of the 28 monoclonal antibodies as detection antibodies in Western blot, immunofluorescence (IF) and immunohistochemistry (IHC), and as capture antibodies in sandwich ELISA

| | Western blot | | | | | | IF | | | capture antibody (sandwich ELISA) | |
|---|---|---|---|---|---|---|---|---|---|---|---|
| | recGPBP | | natGPBP (293) | | | | | | | | |
| | intracel | extracel | 45 | 77 | 88 | 91 | rec | nat | IHC | rec | nat (serum) |
| N1 | ++ | − | − | − | − | − | + | +/− | +/− | ++ | − |
| N2 | +++ | + | − | +/− | − | − | +++ | +/− | +/− | +/− | − |
| N3 | +++ | + | − | + | − | − | ++ | +/− | + | ++ | + |
| N4 | ++++ | ++++ | + | ++++ | + | − | ++ | +/− | + | + | − |
| N5 | ++++ | +++ | ++ | ++ | − | − | ++ | ++ | ++ | +++ | ++ |
| N6 | + | − | − | − | − | − | +/− | +/− | ++ | +++ | − |
| N7 | ++++ | ++++ | − | ++++ | + | − | ++ | +/− | ++ | + | − |
| N8 | +++ | ++ | − | +/− | − | − | +++ | +/− | ++ | ++ | +/− |
| N9 | +++ | ++ | − | +/− | − | − | +++ | +/− | ++ | ++ | + |
| N10 | +++ | + | ++ | +++ | − | − | ++ | +/− | ++ | ++ | + |
| N11 | ++++ | ++++ | ++ | ++++ | ++ | − | ++ | +/− | − | +++ | ++ |
| N12 | +++ | +++ | +++ | +++ | − | − | ++ | ++ | +++ | +++ | +++ |
| N13 | +++ | +++ | + | + | − | − | ++++ | +/− | + | ++ | ++ |
| N14 | ++++ | ++++ | + | ++++ | ++ | − | +++ | +/− | + | ++ | − |
| N15 | +++ | ++ | − | +/− | − | − | +++ | +/− | +/− | +++ | − |
| N16 | ++++ | ++ | + | ++ | − | − | +++ | ++ | + | +++ | − |
| N17 | + | − | − | − | − | − | + | +/− | +/− | +/− | − |
| N18 | ++ | − | − | − | − | − | ++ | +/− | +/− | +/− | +/− |
| N19 | +++ | − | − | − | − | − | + | +/− | +/− | +/− | − |
| N20 | − | − | smear | | | | ++ | +/− | + | ++ | +/− |
| N21 | − | − | smear | | | | +++ | ++ | + | + | − |
| N22 | ++++ | ++++ | − | ++++ | − | − | ++++ | +/− | +/− | + | − |
| N23 | ++++ | + | − | − | − | − | ++ | +/− | +/− | ++ | +/− |
| N24 | ++ | − | smear | | | | ++ | + | + | + | +/− |
| N25 | +++ | ++ | ++ | + | − | − | ++ | +/− | +/− | + | − |
| N26 | ++ | − | − | − | − | ++ | +++ | ++ | ++ | ++ | ++ |
| N27 | ++++ | ++++ | ++ | ++++ | ++ | − | ++ | ++ | ++ | +++ | ++ |
| N28 | ++++ | ++++ | ++ | + | − | − | + | +/− | + | ++ | +/− |

We claim:

1. A method for detecting circulating 77 kD Goodpasture antigen binding protein (GPBP), comprising
   (a) contacting a plasma sample with an antibody that binds to 77 kD GPBP as set forth in SEQ ID NO:4 under conditions to promote selective binding of the antibody to the 77 kD GPBP;
   (b) removing unbound plasma and/or antibody; and
   (c) detecting complex formation between the antibody and the 77 kD GPBP in the plasma sample.

2. The method of claim 1, wherein the method comprises detecting native circulating 77 kD GPBP from human plasma.

3. The method of claim 1, wherein the antibody is a monoclonal antibody.

4. The method of claim 1, wherein the detecting comprises a technique selected from the group consisting of ELISA, immunofluorescence, flow cytometry, and chromatography.

5. The method of claim 1 wherein the plasma sample is obtained from a human subject suspected of having an autoimmune condition selected from the group consisting of Goodpasture Syndrome and immune-complex mediated glomerulonephritis.

6. The method of claim 2, wherein the antibody is a monoclonal antibody.

7. The method of claim 2, wherein the detecting comprises a technique selected from the group consisting of ELISA, immunofluorescence, flow cytometry, and chromatography.

8. The method of claim 2 wherein the plasma sample is obtained from a human subject suspected of having an autoimmune condition selected from the group consisting of Goodpasture Syndrome and immune-complex mediated glomerulonephritis.

9. The method of claim 6, wherein the detecting comprises a technique selected from the group consisting of ELISA, immunofluorescence, flow cytometry, and chromatography.

10. The method of claim 6 wherein the plasma sample is obtained from a human subject suspected of having an autoimmune condition selected from the group consisting of Goodpasture Syndrome and immune-complex mediated glomerulonephritis.

11. The method of claim 5, wherein the method is used to diagnose the human subject as having an autoimmune condition selected from the group consisting of Goodpasture Syndrome and immune-complex mediated glomerulonephritis, wherein an increase in 77 kD GPBP relative to control is indicative of Goodpasture Syndrome or immune-complex mediated glomerulonephritis in the subject.

12. The method of claim 8, wherein the method is used to diagnose the human subject as having an autoimmune condition selected from the group consisting of Goodpasture Syndrome and immune-complex mediated glomerulonephritis, wherein an increase in 77 kD GPBP relative to control is indicative of Goodpasture Syndrome or immune-complex mediated glomerulonephritis in the subject.

13. The method of claim 10, wherein the method is used to diagnose the human subject as having an autoimmune condition selected from the group consisting of Goodpasture Syndrome and immune-complex mediated glomerulonephritis, wherein an increase in 77 kD GPBP relative to control is indicative of Goodpasture Syndrome or immune-complex mediated glomerulonephritis in the subject.

* * * * *

SEQUENCE LISTING

<160> NUMBER OF SEQ ID NOS: 33

<210> SEQ ID NO 1
<211> LENGTH: 2124
<212> TYPE: DNA
<213> ORGANISM: Homo sapiens

<400> SEQUENCE: 1

```
acggcggcgg cggctgacgg ctggaagggt aggcttcctt caccgctcgt cctccttcct      60
cgctccgctc ggtgtcaggc gcggcggcgg cgcggcgggc ggacttcgtc cctcctcctg     120
ctccccccca caccggagcg ggcactcttc gcttcgccat ccccgaccc ttcaccccga     180 ggactggcg cctcctccgg cgcagctgag ggagcgggg ccgtctcct gctcggttgt      240 cgagcctcca tgtcggataa tcagagctgg aactcgtcgg gctcggagga ggatccagag     300
acggagtctg ggccgcctgt ggagcgctgc ggggtcctca gtaagtggac aaactacatt     360
catgggtggc aggatcgttg ggtagttttg aaaaataatg ctctgagtta ctacaaatct     420
```

```
gaagatgaaa cagagtatgg ctgcagagga tccatctgtc ttagcaaggc tgtcatcaca      480
cctcacgatt ttgatgaatg tcgatttgat attagtgtaa atgatagtgt ttggtatctt      540
cgtgctcagg atccagatca tagacagcaa tggatagatg ccattgaaca gcacaagact      600
gaatctggat atggatctga atccagcttg cgtcgacatg gctcaatggt gtccctggtg      660
tctggagcaa gtggctactc tgcaacatcc acctcttcat tcaagaaagg ccacagttta      720
cgtgagaagt tggctgaaat ggaaacattt agagacatct tatgtagaca agttgacacg      780
ctacagaagt actttgatgc ctgtgctgat gctgtctcta aggatgaact tcaaagggat      840
aaagtggtag aagatgatga agatgacttt cctacaacgc gttctgatgg tgacttcttg      900
catagtacca acggcaataa agaaaagtta tttccacatg tgacaccaaa aggaattaat      960
ggtatagact ttaaagggga agcgataact tttaaagcaa ctactgctgg aatccttgca     1020
acactttctc attgtattga actaatggtt aaacgtgagg acagctggca gaagagactg     1080
gataaggaaa ctgagaagaa aagaagaaca gaggaagcat ataaaaatgc aatgacagaa     1140
cttaagaaaa atcccactt tggaggacca gattatgaag aaggccctaa cagtctgatt     1200
aatgaagaag agttctttga tgctgttgaa gctgctcttg acagacaaga taaaatagaa     1260
gaacagtcac agagtgaaaa ggtgagatta cattggccta catccttgcc ctctggagat     1320
gccttttctt ctgtggggac acatagattt gtccaaaagc cctatagtcg ctcttcctcc     1380
atgtcttcca ttgatctagt cagtgcctct gatgatgttc acagattcag ctcccaggtt     1440
gaagagatgt gcagaaacca catgacttac tcattacagg atgtaggcgg agatgccaat     1500
tggcagttgg ttgtagaaga aggagaaatg aaggtataca gaagagaagt agaagaaaat     1560
gggattgttc tggatccttt aaaagctacc catgcagtta aaggcgtcac aggacatgaa     1620
gtctgcaatt atttctggaa tgttgacgtt cgcaatgact gggaaacaac tatagaaaac     1680
tttcatgtgg tggaaacatt agctgataat gcaatcatca tttatcaaac acacaagagg     1740
gtgtggcctg cttctcagcg agacgtatta tatctttctg tcattcgaaa gataccagcc     1800
ttgactgaaa atgaccctga aacttggata gtttgtaatt tttctgtgga tcatgacagt     1860
gctcctctaa caaccgatg tgtccgtgcc aaaataaatg ttgctatgat ttgtcaaacc     1920
ttggtaagcc caccagaggg aaaccaggaa attagcaggg acaacattct atgcaagatt     1980
acatatgtag ctaatgtgaa ccctggagga tgggcaccag cctcagtgtt aagggcagtg     2040
gcaaagcgag agtatcctaa atttctaaaa cgttttactt cttacgtcca agaaaaaact     2100
gcaggaaagc ctattttgtt ctag                                            2124
```

<210> SEQ ID NO 2
<211> LENGTH: 707
<212> TYPE: PRT
<213> ORGANISM: Homo sapiens

<400> SEQUENCE: 2

Thr Ala Ala Ala Ala Asp Gly Trp Lys Gly Arg Leu Pro Ser Pro Leu
1               5                   10                  15

Val Leu Leu Pro Arg Ser Ala Arg Cys Gln Ala Arg Arg Arg Arg Gly
            20                  25                  30

Gly Arg Thr Ser Ser Leu Leu Leu Pro Pro Thr Pro Glu Arg Ala
        35                  40                  45

Leu Phe Ala Ser Pro Ser Pro Asp Pro Ser Pro Arg Gly Leu Gly Ala
    50                  55                  60

Ser Ser Gly Ala Ala Glu Gly Ala Gly Ala Gly Leu Leu Leu Gly Cys

```
            65                  70                  75                  80
Arg Ala Ser Met Ser Asp Asn Gln Ser Trp Asn Ser Ser Gly Ser Glu
                85                  90                  95

Glu Asp Pro Glu Thr Glu Ser Gly Pro Pro Val Glu Arg Cys Gly Val
               100                 105                 110

Leu Ser Lys Trp Thr Asn Tyr Ile His Gly Trp Gln Asp Arg Trp Val
               115                 120                 125

Val Leu Lys Asn Asn Ala Leu Ser Tyr Lys Ser Glu Asp Glu Thr
    130                 135                 140

Glu Tyr Gly Cys Arg Gly Ser Ile Cys Leu Ser Lys Ala Val Ile Thr
145                 150                 155                 160

Pro His Asp Phe Asp Glu Cys Arg Phe Asp Ile Ser Val Asn Asp Ser
                165                 170                 175

Val Trp Tyr Leu Arg Ala Gln Asp Pro Asp His Arg Gln Gln Trp Ile
                180                 185                 190

Asp Ala Ile Glu Gln His Lys Thr Glu Ser Gly Tyr Gly Ser Glu Ser
                195                 200                 205

Ser Leu Arg Arg His Gly Ser Met Val Ser Leu Val Ser Gly Ala Ser
    210                 215                 220

Gly Tyr Ser Ala Thr Ser Thr Ser Ser Phe Lys Lys Gly His Ser Leu
225                 230                 235                 240

Arg Glu Lys Leu Ala Glu Met Glu Thr Phe Arg Asp Ile Leu Cys Arg
                245                 250                 255

Gln Val Asp Thr Leu Gln Lys Tyr Phe Asp Ala Cys Ala Asp Ala Val
                260                 265                 270

Ser Lys Asp Glu Leu Gln Arg Asp Lys Val Val Glu Asp Asp Glu Asp
    275                 280                 285

Asp Phe Pro Thr Thr Arg Ser Asp Gly Asp Phe Leu His Ser Thr Asn
    290                 295                 300

Gly Asn Lys Glu Lys Leu Phe Pro His Val Thr Pro Lys Gly Ile Asn
305                 310                 315                 320

Gly Ile Asp Phe Lys Gly Glu Ala Ile Thr Phe Lys Ala Thr Thr Ala
                325                 330                 335

Gly Ile Leu Ala Thr Leu Ser His Cys Ile Glu Leu Met Val Lys Arg
                340                 345                 350

Glu Asp Ser Trp Gln Lys Arg Leu Asp Lys Glu Thr Glu Lys Lys Arg
    355                 360                 365

Arg Thr Glu Glu Ala Tyr Lys Asn Ala Met Thr Glu Leu Lys Lys Lys
    370                 375                 380

Ser His Phe Gly Gly Pro Asp Tyr Glu Glu Gly Pro Asn Ser Leu Ile
385                 390                 395                 400

Asn Glu Glu Glu Phe Phe Asp Ala Val Glu Ala Ala Leu Asp Arg Gln
                405                 410                 415

Asp Lys Ile Glu Glu Gln Ser Gln Ser Glu Lys Val Arg Leu His Trp
                420                 425                 430

Pro Thr Ser Leu Pro Ser Gly Asp Ala Phe Ser Ser Val Gly Thr His
                435                 440                 445

Arg Phe Val Gln Lys Pro Tyr Ser Arg Ser Ser Met Ser Ser Ile
    450                 455                 460

Asp Leu Val Ser Ala Ser Asp Asp Val His Arg Phe Ser Ser Gln Val
465                 470                 475                 480

Glu Glu Met Val Gln Asn His Met Thr Tyr Ser Leu Gln Asp Val Gly
                485                 490                 495
```

-continued

```
Gly Asp Ala Asn Trp Gln Leu Val Val Glu Glu Gly Glu Met Lys Val
            500                 505                 510

Tyr Arg Arg Glu Val Glu Glu Asn Gly Ile Val Leu Asp Pro Leu Lys
        515                 520                 525

Ala Thr His Ala Val Lys Gly Val Thr Gly His Glu Val Cys Asn Tyr
    530                 535                 540

Phe Trp Asn Val Asp Val Arg Asn Asp Trp Glu Thr Thr Ile Glu Asn
545                 550                 555                 560

Phe His Val Val Glu Thr Leu Ala Asp Asn Ala Ile Ile Ile Tyr Gln
                565                 570                 575

Thr His Lys Arg Val Trp Pro Ala Ser Gln Arg Asp Val Leu Tyr Leu
            580                 585                 590

Ser Val Ile Arg Lys Ile Pro Ala Leu Thr Glu Asn Asp Pro Glu Thr
        595                 600                 605

Trp Ile Val Cys Asn Phe Ser Val Asp His Asp Ser Ala Pro Leu Asn
    610                 615                 620

Asn Arg Cys Val Arg Ala Lys Ile Asn Val Ala Met Ile Cys Gln Thr
625                 630                 635                 640

Leu Val Ser Pro Pro Glu Gly Asn Gln Glu Ile Ser Arg Asp Asn Ile
                645                 650                 655

Leu Cys Lys Ile Thr Tyr Val Ala Asn Val Asn Pro Gly Gly Trp Ala
            660                 665                 670

Pro Ala Ser Val Leu Arg Ala Val Ala Lys Arg Glu Tyr Pro Lys Phe
        675                 680                 685

Leu Lys Arg Phe Thr Ser Tyr Val Gln Glu Lys Thr Ala Gly Lys Pro
    690                 695                 700

Ile Leu Phe
705

<210> SEQ ID NO 3
<211> LENGTH: 1875
<212> TYPE: DNA
<213> ORGANISM: Homo sapiens

<400> SEQUENCE: 3
atgtcggata atcagagctg gaactcgtcg ggctcggagg aggatccaga gacggagtct        60
gggccgcctg tggagcgctg cggggtcctc agtaagtgga caaactacat tcatgggtgg       120
caggatcgtt gggtagtttt gaaaaataat gctctgagtt actacaaatc tgaagatgaa       180
acagagtatg ctgcagagg atccatctgt cttagcaagg ctgtcatcac acctcacgat        240
tttgatgaat gtcgatttga tattagtgta aatgatagtg tttggtatct tcgtgctcag       300
gatccagatc atagacagca atggatagat gccattgaac agcacaagac tgaatctgga       360
tatggatctg aatccagctt gcgtcgacat ggctcaatgg tgtccctggt gtctggagca       420
agtggctact ctgcaacatc cacctcttca ttcaagaaag ccacagtttt acgtgagaag       480
ttggctgaaa tggaaacatt tagagacatc ttatgtagac aagttgacac gctacagaag       540
tactttgatg cctgtgctga tgctgtctct aaggatgaac ttcaaaggga taaagtggta       600
gaagatgatg aagatgactt tcctacaacg cgttctgatg gtgacttctt gcatagtacc       660
aacggcaata agaaaagtt atttccacat gtgacaccaa aaggaattaa tggtatagac       720
tttaaggggg aagcgataac ttttaaagca actactgctg gaatccttgc aacactttct       780
cattgtattg aactaatggt taaacgtgag gacagctggc agaagagact ggataaggaa       840
actgagaaga aagaagaac agaggaagca tataaaaatg caatgacaga acttaagaaa       900
```

-continued

```
aaatcccact ttggaggacc agattatgaa gaaggcccta acagtctgat taatgaagaa    960
gagttctttg atgctgttga agctgctctt gacagacaag ataaaataga agaacagtca   1020
cagagtgaaa aggtgagatt acattggcct acatccttgc cctctggaga tgccttttct   1080
tctgtgggga cacatagatt tgtccaaaag ccctatagtc gctcttcctc catgtcttcc   1140
attgatctag tcagtgcctc tgatgatgtt cacagattca gctcccaggt tgaagagatg   1200
gtgcagaacc acatgactta ctcattacag gatgtaggcg agatgccaa ttggcagttg    1260
gttgtagaag aaggagaaat gaaggtatac agaagagaag tagaagaaaa tgggattgtt   1320
ctggatcctt taaaagctac ccatgcagtt aaaggcgtca caggacatga agtctgcaat   1380
tatttctgga atgttgacgt tcgcaatgac tgggaaacaa ctatagaaaa ctttcatgtg   1440
gtggaaacat tagctgataa tgcaatcatc atttatcaaa cacacaagag ggtgtggcct   1500
gcttctcagc gagacgtatt atatctttct gtcattcgaa agataccagc cttgactgaa   1560
aatgaccctg aaacttggat agtttgtaat ttttctgtgg atcatgacag tgctcctcta   1620
aacaaccgat gtgtccgtgc caaaataaat gttgctatga tttgtcaaac cttggtaagc   1680
ccaccagagg gaaaccagga aattagcagg acaacattc tatgcaagat tacatatgta    1740
gctaatgtga accctggagg atgggcacca gcctcagtgt taagggcagt ggcaaagcga   1800
gagtatccta aatttctaaa acgttttact tcttacgtcc aagaaaaaac tgcaggaaag   1860
cctattttgt tctag                                                   1875
```

<210> SEQ ID NO 4
<211> LENGTH: 624
<212> TYPE: PRT
<213> ORGANISM: Homo sapiens

<400> SEQUENCE: 4

```
Met Ser Asp Asn Gln Ser Trp Asn Ser Gly Ser Glu Glu Asp Pro
1               5                   10                  15

Glu Thr Glu Ser Gly Pro Pro Val Glu Arg Cys Gly Val Leu Ser Lys
                20                  25                  30

Trp Thr Asn Tyr Ile His Gly Trp Gln Asp Arg Trp Val Val Leu Lys
            35                  40                  45

Asn Asn Ala Leu Ser Tyr Tyr Lys Ser Glu Asp Glu Thr Glu Tyr Gly
        50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
                100                 105                 110

Glu Gln His Lys Thr Glu Ser Gly Tyr Gly Ser Glu Ser Ser Leu Arg
            115                 120                 125

Arg His Gly Ser Met Val Ser Leu Val Ser Gly Ala Ser Gly Tyr Ser
        130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
                180                 185                 190

Glu Leu Gln Arg Asp Lys Val Val Glu Asp Asp Glu Asp Asp Phe Pro
            195                 200                 205
```

-continued

Thr Thr Arg Ser Asp Gly Asp Phe Leu His Ser Thr Asn Gly Asn Lys
    210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                    245                 250                 255

Ala Thr Leu Ser His Cys Ile Glu Leu Met Val Lys Arg Glu Asp Ser
                260                 265                 270

Trp Gln Lys Arg Leu Asp Lys Glu Thr Glu Lys Lys Arg Arg Thr Glu
            275                 280                 285

Glu Ala Tyr Lys Asn Ala Met Thr Glu Leu Lys Lys Lys Ser His Phe
290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                    325                 330                 335

Glu Glu Gln Ser Gln Ser Glu Lys Val Arg Leu His Trp Pro Thr Ser
                340                 345                 350

Leu Pro Ser Gly Asp Ala Phe Ser Ser Val Gly Thr His Arg Phe Val
            355                 360                 365

Gln Lys Pro Tyr Ser Arg Ser Ser Met Ser Ser Ile Asp Leu Val
370                 375                 380

Ser Ala Ser Asp Asp Val His Arg Phe Ser Ser Gln Val Glu Glu Met
385                 390                 395                 400

Val Gln Asn His Met Thr Tyr Ser Leu Gln Asp Val Gly Gly Asp Ala
                    405                 410                 415

Asn Trp Gln Leu Val Val Glu Glu Gly Glu Met Lys Val Tyr Arg Arg
                420                 425                 430

Glu Val Glu Glu Asn Gly Ile Val Leu Asp Pro Leu Lys Ala Thr His
            435                 440                 445

Ala Val Lys Gly Val Thr Gly His Glu Val Cys Asn Tyr Phe Trp Asn
450                 455                 460

Val Asp Val Arg Asn Asp Trp Glu Thr Thr Ile Glu Asn Phe His Val
465                 470                 475                 480

Val Glu Thr Leu Ala Asp Asn Ala Ile Ile Ile Tyr Gln Thr His Lys
                    485                 490                 495

Arg Val Trp Pro Ala Ser Gln Arg Asp Val Leu Tyr Leu Ser Val Ile
                500                 505                 510

Arg Lys Ile Pro Ala Leu Thr Glu Asn Asp Pro Glu Thr Trp Ile Val
            515                 520                 525

Cys Asn Phe Ser Val Asp His Asp Ser Ala Pro Leu Asn Asn Arg Cys
530                 535                 540

Val Arg Ala Lys Ile Asn Val Ala Met Ile Cys Gln Thr Leu Val Ser
545                 550                 555                 560

Pro Pro Glu Gly Asn Gln Glu Ile Ser Arg Asp Asn Ile Leu Cys Lys
                    565                 570                 575

Ile Thr Tyr Val Ala Asn Val Asn Pro Gly Gly Trp Ala Pro Ala Ser
                580                 585                 590

Val Leu Arg Ala Val Ala Lys Arg Glu Tyr Pro Lys Phe Leu Lys Arg
            595                 600                 605

Phe Thr Ser Tyr Val Gln Glu Lys Thr Ala Gly Lys Pro Ile Leu Phe
610                 615                 620

```
<210> SEQ ID NO 5
<211> LENGTH: 8
<212> TYPE: PRT
<213> ORGANISM: Homo sapiens

<400> SEQUENCE: 5

Glu Glu Phe Phe Asp Ala Val Glu
1               5

<210> SEQ ID NO 6
<211> LENGTH: 5
<212> TYPE: PRT
<213> ORGANISM: Homo sapiens

<400> SEQUENCE: 6

Asp Asp Val His Arg
1               5

<210> SEQ ID NO 7
<211> LENGTH: 20
<212> TYPE: PRT
<213> ORGANISM: Homo sapiens

<400> SEQUENCE: 7

Asp Gly Trp Lys Gly Arg Leu Pro Ser Pro Leu Val Leu Leu Pro Arg
1               5                   10                  15

Ser Ala Arg Cys
            20

<210> SEQ ID NO 8
<211> LENGTH: 18
<212> TYPE: PRT
<213> ORGANISM: Homo sapiens

<400> SEQUENCE: 8

Leu Ile Asn Glu Glu Glu Phe Phe Asp Ala Val Glu Ala Ala Leu Asp
1               5                   10                  15

Arg Gln

<210> SEQ ID NO 9
<211> LENGTH: 26
<212> TYPE: PRT
<213> ORGANISM: Homo sapiens

<400> SEQUENCE: 9

Pro Tyr Ser Arg Ser Ser Ser Met Ser Ser Ile Asp Leu Val Ser Ala
1               5                   10                  15

Ser Asp Asp Val His Arg Phe Ser Ser Gln
            20                  25

<210> SEQ ID NO 10
<211> LENGTH: 40
<212> TYPE: PRT
<213> ORGANISM: Homo sapiens

<400> SEQUENCE: 10

Gly Gly Pro Asp Tyr Glu Glu Gly Pro Asn Ser Leu Ile Asn Glu Glu
1               5                   10                  15

Glu Phe Phe Asp Ala Val Glu Ala Ala Leu Asp Arg Gln Asp Lys Ile
            20                  25                  30

Glu Glu Gln Ser Gln Ser Glu Lys
        35                  40
```

```
<210> SEQ ID NO 11
<211> LENGTH: 19
<212> TYPE: DNA
<213> ORGANISM: Artificial Sequence
<220> FEATURE:
<223> OTHER INFORMATION: Synthetic; pSi-GPBP/GPBP_Delta_26-2 cDNA
      target sequence

<400> SEQUENCE: 11
acagagtatg gctgcagag                                                  19

<210> SEQ ID NO 12
<211> LENGTH: 19
<212> TYPE: DNA
<213> ORGANISM: Artificial Sequence
<220> FEATURE:
<223> OTHER INFORMATION: Synthetic; pSi-GPBP/GPBP_Delta_26-3 cDNA
      target sequence

<400> SEQUENCE: 12
gtactttgat gcctgtgct                                                  19

<210> SEQ ID NO 13
<211> LENGTH: 19
<212> TYPE: DNA
<213> ORGANISM: Artificial Sequence
<220> FEATURE:
<223> OTHER INFORMATION: Synthetic; pSi-GPBP-1 cDNA target sequence

<400> SEQUENCE: 13
gccctatagt cgctcttcc                                                  19

<210> SEQ ID NO 14
<211> LENGTH: 411
<212> TYPE: DNA
<213> ORGANISM: Homo sapiens

<400> SEQUENCE: 14
gcaggaagat ggcggcggta gcggaggtgt gagtggacgc gggactcagc ggccggattt     60
tctcttccct tcttttccct tttccttccc tatttgaaat tggcatcgag ggggctaagt    120
tcgggtggca gcgccgggcg caacgcaggg gtcacggcga cggcggcggc ggctgacggc    180
tggaagggta ggcttccttc accgctcgtc ctccttcctc gctccgctcg gtgtcaggcg    240
cggcggcggc gcggcgggcg gacttcgtcc ctcctcctgc tcccccccac accggagcgg    300
gcactcttcg cttcgccatc ccccgaccct tcaccccgag gactgggcgc ctcctccggc    360
gcagctgagg gagcggggc cggtctcctg ctcggttgtc gagcctccat g              411

<210> SEQ ID NO 15
<211> LENGTH: 130
<212> TYPE: PRT
<213> ORGANISM: Homo sapiens

<400> SEQUENCE: 15

Arg Arg Cys Glu Trp Thr Arg Asp Ser Ala Ala Gly Phe Ser Leu Pro
1               5                   10                  15

Phe Phe Ser Leu Phe Leu Pro Tyr Leu Lys Leu Ala Ser Arg Gly Leu
                20                  25                  30

Ser Ser Gly Gly Ser Ala Gly Arg Asn Ala Gly Val Thr Ala Thr Ala
            35                  40                  45

Ala Ala Ala Asp Gly Trp Lys Gly Arg Leu Pro Ser Pro Leu Val Leu
        50                  55                  60

Leu Pro Arg Ser Ala Arg Cys Gln Ala Arg Arg Arg Arg Gly Gly Arg
```

```
                65                  70                  75                  80
        Thr Ser Ser Leu Leu Leu Pro Pro Thr Pro Glu Arg Ala Leu Phe
                        85                  90                  95

Ala Ser Pro Ser Pro Asp Pro Ser Pro Arg Gly Leu Gly Ala Ser Ser
                    100                 105                 110

Gly Ala Ala Glu Gly Ala Gly Ala Gly Leu Leu Leu Gly Cys Arg Ala
                    115                 120                 125

Ser Met
            130

<210> SEQ ID NO 16
<211> LENGTH: 265
<212> TYPE: PRT
<213> ORGANISM: Homo sapiens

<400> SEQUENCE: 16

Arg Asp Glu Val Ile Gly Ile Leu Lys Ala Glu Lys Met Asp Leu Ala
        1               5                   10                  15

Leu Leu Glu Ala Gln Tyr Gly Phe Val Thr Pro Lys Lys Val Leu Glu
                    20                  25                  30

Ala Leu Gln Arg Asp Ala Phe Gln Ala Lys Ser Thr Pro Trp Gln Glu
                35                  40                  45

Asp Ile Tyr Glu Lys Pro Met Asn Glu Leu Asp Lys Val Val Glu Lys
            50                  55                  60

His Lys Glu Ser Tyr Arg Arg Ile Leu Gly Gln Leu Leu Val Ala Glu
        65                  70                  75                  80

Lys Ser Arg Arg Gln Thr Ile Leu Glu Leu Glu Glu Lys Arg Lys
                        85                  90                  95

His Lys Glu Tyr Met Glu Lys Ser Asp Glu Phe Ile Cys Leu Leu Glu
                    100                 105                 110

Gln Glu Cys Glu Arg Leu Lys Lys Leu Ile Asp Gln Glu Ile Lys Ser
                    115                 120                 125

Gln Glu Glu Lys Glu Gln Glu Lys Lys Arg Val Thr Thr Leu Lys
            130                 135                 140

Glu Glu Leu Thr Lys Leu Lys Ser Phe Ala Leu Met Val Val Asp Glu
        145                 150                 155                 160

Gln Gln Arg Leu Thr Ala Gln Leu Thr Leu Gln Arg Gln Lys Ile Gln
                        165                 170                 175

Glu Leu Thr Thr Asn Ala Lys Glu Thr His Thr Lys Leu Ala Leu Ala
                    180                 185                 190

Glu Ala Arg Val Gln Glu Glu Glu Gln Lys Ala Thr Arg Leu Glu Lys
                    195                 200                 205

Glu Leu Gln Thr Gln Thr Thr Lys Phe His Gln Asp Gln Asp Thr Ile
            210                 215                 220

Met Ala Lys Leu Thr Asn Glu Asp Ser Gln Asn Arg Gln Leu Gln Gln
        225                 230                 235                 240

Lys Leu Ala Ala Leu Ser Arg Gln Ile Asp Glu Leu Glu Glu Thr Asn
                        245                 250                 255

Arg Ser Leu Arg Lys Ala Glu Glu Glu
                    260                 265

<210> SEQ ID NO 17
<211> LENGTH: 764
<212> TYPE: PRT
<213> ORGANISM: Homo sapiens

<400> SEQUENCE: 17
```

-continued

```
Met Arg Ser Arg Gly Ser Asp Thr Glu Gly Ser Ala Gln Lys Lys Phe
 1               5                  10                  15

Pro Arg His Thr Lys Gly His Ser Phe Gln Gly Pro Lys Asn Met Lys
             20                  25                  30

His Arg Gln Gln Asp Lys Asp Ser Pro Ser Glu Ser Asp Val Ile Leu
             35                  40                  45

Pro Cys Pro Lys Ala Glu Lys Pro His Ser Gly Asn Gly His Gln Ala
 50                  55                  60

Glu Asp Leu Ser Arg Asp Asp Leu Leu Phe Leu Leu Ser Ile Leu Glu
 65                  70                  75                  80

Gly Glu Leu Gln Ala Arg Asp Glu Val Ile Gly Ile Leu Lys Ala Glu
                 85                  90                  95

Lys Met Asp Leu Ala Leu Leu Glu Ala Gln Tyr Gly Phe Val Thr Pro
             100                 105                 110

Lys Lys Val Leu Glu Ala Leu Gln Arg Asp Ala Phe Gln Ala Lys Ser
             115                 120                 125

Thr Pro Trp Gln Glu Asp Ile Tyr Glu Lys Pro Met Asn Glu Leu Asp
             130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                 165                 170                 175

Glu Glu Lys Arg Lys His Lys Glu Tyr Met Glu Lys Ser Asp Glu Phe
             180                 185                 190

Ile Cys Leu Leu Glu Gln Glu Cys Glu Arg Leu Lys Lys Leu Ile Asp
             195                 200                 205

Gln Glu Ile Lys Ser Gln Glu Glu Lys Glu Gln Glu Lys Glu Lys Arg
 210                 215                 220

Val Thr Thr Leu Lys Glu Glu Leu Thr Lys Leu Lys Ser Phe Ala Leu
225                 230                 235                 240

Met Val Val Asp Glu Gln Gln Arg Leu Thr Ala Gln Leu Thr Leu Gln
             245                 250                 255

Arg Gln Lys Ile Gln Glu Leu Thr Thr Asn Ala Lys Glu Thr His Thr
             260                 265                 270

Lys Leu Ala Leu Ala Glu Ala Arg Val Gln Glu Glu Gln Lys Ala
             275                 280                 285

Thr Arg Leu Glu Lys Glu Leu Gln Thr Gln Thr Thr Lys Phe His Gln
 290                 295                 300

Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
             325                 330                 335

Leu Glu Glu Thr Asn Arg Ser Leu Arg Lys Ala Glu Glu Glu Leu Gln
             340                 345                 350

Asp Ile Lys Glu Lys Ile Ser Lys Gly Glu Tyr Gly Asn Ala Gly Ile
             355                 360                 365

Met Ala Glu Val Glu Glu Leu Arg Lys Arg Val Leu Asp Met Glu Gly
             370                 375                 380

Lys Asp Glu Glu Leu Ile Lys Met Glu Glu Gln Cys Arg Asp Leu Asn
385                 390                 395                 400

Lys Arg Leu Glu Arg Glu Thr Leu Gln Ser Lys Asp Phe Lys Leu Glu
                 405                 410                 415

Val Glu Lys Leu Ser Lys Arg Ile Met Ala Leu Glu Lys Leu Glu Asp
```

```
                    420             425             430
Ala Phe Asn Lys Ser Lys Gln Glu Cys Tyr Ser Leu Lys Cys Asn Leu
            435                 440                 445

Glu Lys Glu Arg Met Thr Thr Lys Gln Leu Ser Gln Glu Leu Glu Ser
        450                 455                 460

Leu Lys Val Arg Ile Lys Glu Leu Glu Ala Ile Glu Ser Arg Leu Glu
465                 470                 475                 480

Lys Thr Glu Phe Thr Leu Lys Glu Asp Leu Thr Lys Leu Lys Thr Leu
                485                 490                 495

Thr Val Met Phe Val Asp Glu Arg Lys Thr Met Ser Glu Lys Leu Lys
                500                 505                 510

Lys Thr Glu Asp Lys Leu Gln Ala Ala Ser Ser Gln Leu Gln Val Glu
        515                 520                 525

Gln Asn Lys Val Thr Thr Val Thr Glu Lys Leu Ile Glu Glu Thr Lys
    530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu Glu
                565                 570                 575

Lys Gly Asn Asp Leu Leu Ser Arg Val Asn Met Leu Lys Asn Arg Leu
            580                 585                 590

Gln Ser Leu Glu Ala Ile Glu Lys Asp Phe Leu Lys Asn Lys Leu Asn
        595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Asp Leu Met Lys Thr Glu Asp Glu Tyr
                645                 650                 655

Glu Thr Leu Glu Arg Arg Tyr Ala Asn Glu Arg Asp Lys Ala Gln Phe
            660                 665                 670

Leu Ser Lys Glu Leu Glu His Val Lys Met Glu Leu Ala Lys Tyr Lys
        675                 680                 685

Leu Ala Glu Lys Thr Glu Thr Ser His Glu Gln Trp Leu Phe Lys Arg
    690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Thr Lys Ser
            740                 745                 750

Thr Arg Lys Gln Glu Gln Arg Phe Arg Lys Arg Asp
        755                 760

<210> SEQ ID NO 18
<211> LENGTH: 1135
<212> TYPE: PRT
<213> ORGANISM: Homo sapiens

<400> SEQUENCE: 18

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
                20                  25                  30

His Arg Gln Gln Asp Lys Asp Ser Pro Ser Glu Ser Asp Val Ile Leu
```

```
                35                  40                  45
Pro Cys Pro Lys Ala Glu Lys Pro His Ser Gly Asn Gly His Gln Ala
 50                  55                  60
Glu Asp Leu Ser Arg Asp Asp Leu Leu Phe Leu Leu Ser Ile Leu Glu
 65                  70                  75                  80
Gly Glu Leu Gln Ala Arg Asp Glu Val Ile Gly Ile Leu Lys Ala Glu
                 85                  90                  95
Lys Met Asp Leu Ala Leu Leu Glu Ala Gln Tyr Gly Phe Val Thr Pro
                100                 105                 110
Lys Lys Val Leu Glu Ala Leu Gln Arg Asp Ala Phe Gln Ala Lys Ser
                115                 120                 125
Thr Pro Trp Gln Glu Asp Ile Tyr Glu Lys Pro Met Asn Glu Leu Asp
130                 135                 140
Lys Val Val Glu Lys His Lys Glu Ser Tyr Arg Arg Ile Leu Gly Gln
145                 150                 155                 160
Leu Leu Val Ala Glu Lys Ser Arg Arg Gln Thr Ile Leu Glu Leu Glu
                165                 170                 175
Glu Glu Lys Arg Lys His Lys Glu Tyr Met Glu Lys Ser Asp Glu Phe
                180                 185                 190
Ile Cys Leu Leu Glu Gln Glu Cys Glu Arg Leu Lys Lys Leu Ile Asp
                195                 200                 205
Gln Glu Ile Lys Ser Gln Glu Lys Glu Gln Lys Glu Lys Arg
210                 215                 220
Val Thr Thr Leu Lys Glu Glu Leu Thr Lys Leu Lys Ser Phe Ala Leu
225                 230                 235                 240
Met Val Val Asp Glu Gln Gln Arg Leu Thr Ala Gln Leu Thr Leu Gln
                245                 250                 255
Arg Gln Lys Ile Gln Glu Leu Thr Thr Asn Ala Lys Glu Thr His Thr
                260                 265                 270
Lys Leu Ala Leu Ala Glu Ala Arg Val Gln Glu Glu Gln Lys Ala
                275                 280                 285
Thr Arg Leu Glu Lys Glu Leu Gln Thr Gln Thr Thr Lys Phe His Gln
290                 295                 300
Asp Gln Asp Thr Ile Met Ala Lys Leu Thr Asn Glu Asp Ser Gln Asn
305                 310                 315                 320
Arg Gln Leu Gln Gln Lys Leu Ala Ala Leu Ser Arg Gln Ile Asp Glu
                325                 330                 335
Leu Glu Glu Thr Asn Arg Ser Leu Arg Lys Ala Glu Glu Glu Leu Gln
                340                 345                 350
Asp Ile Lys Glu Lys Ile Ser Lys Gly Glu Tyr Gly Asn Ala Gly Ile
                355                 360                 365
Met Ala Glu Val Glu Glu Leu Arg Lys Arg Val Leu Asp Met Glu Gly
370                 375                 380
Lys Asp Glu Glu Leu Ile Lys Met Glu Glu Gln Cys Arg Asp Leu Asn
385                 390                 395                 400
Lys Arg Leu Glu Arg Glu Thr Leu Gln Ser Lys Asp Phe Lys Leu Glu
                405                 410                 415
Val Glu Lys Leu Ser Lys Arg Ile Met Ala Leu Glu Lys Leu Glu Asp
                420                 425                 430
Ala Phe Asn Lys Ser Lys Gln Glu Cys Tyr Ser Leu Lys Cys Asn Leu
                435                 440                 445
Glu Lys Glu Arg Met Thr Thr Lys Gln Leu Ser Gln Glu Leu Glu Ser
                450                 455                 460
```

-continued

```
Leu Lys Val Arg Ile Lys Glu Leu Glu Ala Ile Glu Ser Arg Leu Glu
465                 470                 475                 480

Lys Thr Glu Phe Thr Leu Lys Glu Asp Leu Thr Lys Leu Lys Thr Leu
                485                 490                 495

Thr Val Met Phe Val Asp Glu Arg Lys Thr Met Ser Glu Lys Leu Lys
            500                 505                 510

Lys Thr Glu Asp Lys Leu Gln Ala Ala Ser Ser Gln Leu Gln Val Glu
        515                 520                 525

Gln Asn Lys Val Thr Thr Val Thr Glu Lys Leu Ile Glu Glu Thr Lys
    530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu Glu
                565                 570                 575

Lys Gly Asn Asp Leu Leu Ser Arg Val Asn Met Leu Lys Asn Arg Leu
            580                 585                 590

Gln Ser Leu Glu Ala Ile Glu Lys Asp Phe Leu Lys Asn Lys Leu Asn
        595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Asp Leu Met Lys Thr Glu Asp Glu Tyr
                645                 650                 655

Glu Thr Leu Glu Arg Arg Tyr Ala Asn Glu Arg Asp Lys Ala Gln Phe
            660                 665                 670

Leu Ser Lys Glu Leu Glu His Val Lys Met Glu Leu Ala Lys Tyr Lys
        675                 680                 685

Leu Ala Glu Lys Thr Glu Thr Ser His Glu Gln Trp Leu Phe Lys Arg
    690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Leu Asn Gln
            740                 745                 750

Gln Glu Asn Arg Asn Arg Asp Leu Gly Arg Glu Ile Glu Asn Leu Thr
        755                 760                 765

Lys Glu Leu Glu Arg Tyr Arg His Phe Ser Lys Ser Leu Arg Pro Ser
    770                 775                 780

Leu Asn Gly Arg Arg Ile Ser Asp Pro Gln Val Phe Ser Lys Glu Val
785                 790                 795                 800

Gln Thr Glu Ala Val Asp Asn Glu Pro Pro Asp Tyr Lys Ser Leu Ile
                805                 810                 815

Pro Leu Glu Arg Ala Val Ile Asn Gly Gln Leu Tyr Glu Glu Ser Glu
            820                 825                 830

Asn Gln Asp Glu Pro Asn Asp Glu Gly Ser Val Leu Ser Phe Lys
        835                 840                 845

Cys Ser Gln Ser Thr Pro Cys Pro Val Asn Arg Lys Leu Trp Ile Pro
    850                 855                 860

Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895
```

Thr Pro Gly Gln Pro Leu His Ile Lys Val Thr Pro Asp His Val Gln
                900                 905                 910

Asn Thr Ala Thr Leu Glu Ile Thr Ser Pro Thr Thr Glu Ser Pro His
            915                 920                 925

Ser Tyr Thr Ser Thr Ala Val Ile Pro Asn Cys Gly Thr Pro Lys Gln
    930                 935                 940

Arg Ile Thr Ile Leu Gln Asn Ala Ser Ile Thr Pro Val Lys Ser Lys
945                 950                 955                 960

Thr Ser Thr Glu Asp Leu Met Asn Leu Glu Gln Gly Met Ser Pro Ile
                965                 970                 975

Thr Met Ala Thr Phe Ala Arg Ala Gln Thr Pro Glu Ser Cys Gly Ser
            980                 985                 990

Leu Thr Pro Glu Arg Thr Met Ser Pro Ile Gln Val Leu Ala Val Thr
        995                 1000                1005

Gly Ser Ala Ser Ser Pro Glu Gln Gly Arg Ser Pro Glu Pro Thr
    1010                1015                1020

Glu Ile Ser Ala Lys His Ala Ile Phe Arg Val Ser Pro Asp Arg
    1025                1030                1035

Gln Ser Ser Trp Gln Phe Gln Arg Ser Asn Ser Asn Ser Ser Ser
    1040                1045                1050

Val Ile Thr Thr Glu Asp Asn Lys Ile His Ile His Leu Gly Ser
    1055                1060                1065

Pro Tyr Met Gln Ala Val Ala Ser Pro Val Arg Pro Ala Ser Pro
    1070                1075                1080

Ser Ala Pro Leu Gln Asp Asn Arg Thr Gln Gly Leu Ile Asn Gly
    1085                1090                1095

Ala Leu Asn Lys Thr Thr Asn Lys Val Thr Ser Ser Ile Thr Ile
    1100                1105                1110

Thr Pro Thr Ala Thr Pro Leu Pro Arg Gln Ser Gln Ile Thr Val
    1115                1120                1125

Glu Pro Leu Leu Leu Pro His
    1130                1135

<210> SEQ ID NO 19
<211> LENGTH: 1133
<212> TYPE: PRT
<213> ORGANISM: Homo sapiens

<400> SEQUENCE: 19

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Leu Phe Leu Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

-continued

Thr Pro Trp Gln Glu Asp Ile Tyr Glu Lys Pro Met Asn Glu Leu Asp
130                 135                 140

Lys Val Val Glu Lys His Lys Glu Ser Tyr Arg Arg Ile Leu Gly Gln
145                 150                 155                 160

Leu Leu Val Ala Glu Lys Ser His Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Lys Glu Gln Lys Glu Lys Arg
210                 215                 220

Val Thr Thr Leu Lys Glu Glu Leu Thr Lys Leu Lys Ser Phe Ala Leu
225                 230                 235                 240

Met Val Val Asp Glu Gln Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270

Lys Leu Ala Leu Ala Glu Ala Arg Val Gln Glu Glu Gln Lys Ala
        275                 280                 285

Thr Arg Leu Glu Lys Glu Leu Gln Thr Gln Thr Thr Lys Phe His Gln
290                 295                 300

Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
                325                 330                 335

Leu Glu Glu Thr Asn Arg Ser Leu Arg Lys Ala Glu Glu Glu Leu Gln
            340                 345                 350

Asp Ile Lys Glu Lys Ile Ser Lys Gly Glu Tyr Gly Asn Ala Gly Ile
        355                 360                 365

Met Ala Glu Val Glu Glu Leu Arg Lys Arg Val Leu Asp Met Glu Gly
370                 375                 380

Lys Asp Glu Glu Leu Ile Lys Met Glu Glu Gln Cys Arg Asp Leu Asn
385                 390                 395                 400

Lys Arg Leu Glu Arg Glu Thr Leu Gln Ser Lys Asp Phe Lys Leu Glu
                405                 410                 415

Val Glu Lys Leu Ser Lys Arg Ile Met Ala Leu Glu Lys Leu Glu Asp
            420                 425                 430

Ala Phe Asn Lys Ser Lys Gln Glu Cys Tyr Ser Leu Lys Cys Asn Leu
        435                 440                 445

Glu Lys Glu Arg Met Thr Thr Lys Gln Leu Ser Gln Glu Leu Glu Ser
    450                 455                 460

Leu Lys Val Arg Ile Lys Glu Leu Glu Ala Ile Glu Ser Arg Leu Glu
465                 470                 475                 480

Lys Thr Glu Phe Thr Leu Lys Glu Asp Leu Thr Lys Leu Lys Thr Leu
                485                 490                 495

Thr Val Met Phe Val Asp Glu Arg Lys Thr Met Ser Glu Lys Leu Lys
            500                 505                 510

Lys Thr Glu Asp Lys Leu Gln Ala Ala Ser Ser Gln Leu Gln Val Glu
        515                 520                 525

Gln Asn Lys Val Thr Thr Val Thr Glu Lys Leu Ile Glu Glu Thr Lys
    530                 535                 540

Arg Ala Leu Lys Ser Lys Thr Asp Val Glu Glu Lys Met Tyr Ser Val

```
                          545                 550                 555                 560
        Thr Lys Glu Arg Asp Asp Leu Lys Asn Lys Leu Lys Ala Glu Glu
                              565                 570                 575
        Lys Gly Asn Asp Leu Leu Ser Arg Val Asn Met Leu Lys Asn Arg Leu
                          580                 585                 590
        Gln Ser Leu Glu Ala Ile Glu Lys Asp Phe Leu Lys Asn Lys Leu Asn
                          595                 600                 605
        Gln Asp Ser Gly Lys Ser Thr Thr Ala Leu His Gln Glu Asn Asn Lys
                          610                 615                 620
        Ile Lys Glu Leu Ser Gln Glu Val Glu Arg Leu Lys Leu Lys Leu Lys
        625                 630                 635                 640
        Asp Met Lys Ala Ile Glu Asp Leu Met Lys Thr Glu Asp Glu Tyr
                              645                 650                 655
        Glu Thr Leu Glu Arg Arg Tyr Ala Asn Glu Arg Asp Lys Ala Gln Phe
                          660                 665                 670
        Leu Ser Lys Glu Leu Glu His Val Lys Met Glu Leu Ala Lys Tyr Lys
                          675                 680                 685
        Leu Ala Glu Lys Thr Glu Thr Ser His Glu Gln Trp Leu Phe Lys Arg
                          690                 695                 700
        Leu Gln Glu Glu Glu Ala Lys Ser Gly His Leu Ser Arg Glu Val Asp
        705                 710                 715                 720
        Ala Leu Lys Glu Lys Ile His Glu Tyr Met Ala Thr Glu Asp Leu Ile
                              725                 730                 735
        Cys His Leu Gln Gly Asp His Ser Val Leu Gln Lys Lys Leu Asn Gln
                          740                 745                 750
        Gln Glu Asn Arg Asn Arg Asp Leu Gly Arg Glu Ile Glu Asn Leu Thr
                          755                 760                 765
        Lys Glu Leu Glu Arg Tyr Arg His Phe Ser Lys Ser Leu Arg Pro Ser
                          770                 775                 780
        Leu Asn Gly Arg Arg Ile Ser Asp Pro Gln Val Phe Ser Lys Glu Val
        785                 790                 795                 800
        Gln Thr Glu Ala Val Asp Asn Glu Pro Pro Asp Tyr Lys Ser Leu Ile
                              805                 810                 815
        Pro Leu Glu Arg Ala Val Ile Asn Gly Gln Leu Tyr Glu Glu Ser Glu
                          820                 825                 830
        Asn Gln Asp Glu Asp Pro Asn Asp Glu Gly Ser Val Leu Ser Phe Lys
                          835                 840                 845
        Cys Ser Gln Ser Thr Pro Cys Pro Val Asn Arg Lys Leu Trp Ile Pro
                          850                 855                 860
        Trp Met Lys Ser Lys Glu Gly His Leu Gln Asn Gly Lys Met Gln Thr
        865                 870                 875                 880
        Lys Pro Asn Ala Asn Phe Val Gln Pro Gly Asp Leu Val Leu Ser His
                              885                 890                 895
        Thr Pro Gly Gln Pro Leu His Ile Lys Val Thr Pro Asp His Val Gln
                          900                 905                 910
        Asn Thr Ala Thr Leu Glu Ile Thr Ser Pro Thr Thr Glu Ser Pro His
                          915                 920                 925
        Ser Tyr Thr Ser Thr Ala Val Ile Pro Asn Cys Gly Thr Pro Lys Gln
                          930                 935                 940
        Arg Ile Thr Ile Leu Gln Asn Ala Ser Ile Thr Pro Val Lys Ser Lys
        945                 950                 955                 960
        Thr Ser Thr Glu Asp Leu Met Asn Leu Glu Gln Gly Met Ser Pro Ile
                              965                 970                 975
```

```
Thr Met Ala Thr Phe Ala Arg Ala Gln Thr Pro Glu Ser Cys Gly Ser
                980                 985                 990

Leu Thr Pro Glu Arg Thr Met Ser Pro Ile Gln Val Leu Ala Val Thr
            995                 1000                1005

Gly Ser Ala Ser Ser Pro Glu Gln Gly Arg Ser Pro Glu Pro Thr
    1010                1015                1020

Glu Ile Ser Ala Lys His Ala Ile Phe Arg Val Ser Pro Asp Arg
    1025                1030                1035

Gln Ser Ser Trp Gln Phe Gln Arg Ser Asn Ser Asn Ser Ser Ser
    1040                1045                1050

Val Ile Thr Thr Glu Asp Asn Lys Ile His Ile His Leu Gly Ser
    1055                1060                1065

Pro Tyr Met Gln Ala Val Ala Ser Pro Val Arg Pro Ala Ser Pro
    1070                1075                1080

Ser Ala Pro Leu Gln Asp Asn Arg Thr Gln Gly Leu Ile Asn Gly
    1085                1090                1095

Ala Leu Asn Lys Thr Thr Asn Lys Val Thr Ser Ser Ile Thr Ile
    1100                1105                1110

Thr Pro Thr Ala Thr Pro Leu Pro Arg Gln Ser Gln Ile Thr Val
    1115                1120                1125

Ser Asn Ile Tyr Asn
    1130

<210> SEQ ID NO 20
<211> LENGTH: 1133
<212> TYPE: PRT
<213> ORGANISM: Homo sapiens

<400> SEQUENCE: 20

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Leu Leu Phe Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205
```

-continued

```
Gln Glu Ile Lys Ser Gln Glu Lys Glu Gln Lys Glu Lys Arg
    210                 215                 220
Val Thr Thr Leu Lys Glu Leu Thr Lys Leu Lys Ser Phe Ala Leu
225                 230                 235                 240
Met Val Val Asp Glu Gln Gln Arg Leu Thr Ala Gln Leu Thr Leu Gln
                    245                 250                 255
Arg Gln Lys Ile Gln Glu Leu Thr Thr Asn Ala Lys Glu Thr His Thr
            260                 265                 270
Lys Leu Ala Leu Ala Glu Ala Arg Val Gln Glu Glu Gln Lys Ala
        275                 280                 285
Thr Arg Leu Glu Lys Glu Leu Gln Thr Gln Thr Thr Lys Phe His Gln
    290                 295                 300
Asp Gln Asp Thr Ile Met Ala Lys Leu Thr Asn Glu Asp Ser Gln Asn
305                 310                 315                 320
Arg Gln Leu Gln Gln Lys Leu Ala Ala Leu Ser Arg Gln Ile Asp Glu
                    325                 330                 335
Leu Glu Glu Thr Asn Arg Ser Leu Arg Lys Ala Glu Glu Leu Gln
            340                 345                 350
Asp Ile Lys Glu Lys Ile Ser Lys Gly Glu Tyr Gly Asn Ala Gly Ile
        355                 360                 365
Met Ala Glu Val Glu Glu Leu Arg Lys Arg Val Leu Asp Met Glu Gly
    370                 375                 380
Lys Asp Glu Glu Leu Ile Lys Met Glu Glu Gln Cys Arg Asp Leu Asn
385                 390                 395                 400
Lys Arg Leu Glu Arg Glu Thr Leu Gln Ser Lys Asp Phe Lys Leu Glu
                    405                 410                 415
Val Glu Lys Leu Ser Lys Arg Ile Met Ala Leu Glu Lys Leu Glu Asp
            420                 425                 430
Ala Phe Asn Lys Ser Lys Gln Glu Cys Tyr Ser Leu Lys Cys Asn Leu
        435                 440                 445
Glu Lys Glu Arg Met Thr Thr Lys Gln Leu Ser Gln Glu Leu Glu Ser
    450                 455                 460
Leu Lys Val Arg Ile Lys Glu Leu Glu Ala Ile Glu Ser Arg Leu Glu
465                 470                 475                 480
Lys Thr Glu Phe Thr Leu Lys Glu Asp Leu Thr Lys Leu Lys Thr Leu
                    485                 490                 495
Thr Val Met Phe Val Asp Glu Arg Lys Thr Met Ser Glu Lys Leu Lys
            500                 505                 510
Lys Thr Glu Asp Lys Leu Gln Ala Ala Ser Ser Gln Leu Gln Val Glu
        515                 520                 525
Gln Asn Lys Val Thr Thr Val Thr Glu Lys Leu Ile Glu Glu Thr Lys
    530                 535                 540
Arg Ala Leu Lys Ser Lys Thr Asp Val Glu Glu Lys Met Tyr Ser Val
545                 550                 555                 560
Thr Lys Glu Arg Asp Asp Leu Lys Asn Lys Leu Lys Ala Glu Glu Glu
                    565                 570                 575
Lys Gly Asn Asp Leu Leu Ser Arg Val Asn Met Leu Lys Asn Arg Leu
            580                 585                 590
Gln Ser Leu Glu Ala Ile Glu Lys Asp Phe Leu Lys Asn Lys Leu Asn
        595                 600                 605
Gln Asp Ser Gly Lys Ser Thr Thr Ala Leu His Gln Glu Asn Asn Lys
    610                 615                 620
Ile Lys Glu Leu Ser Gln Glu Val Glu Arg Leu Lys Leu Lys Leu Lys
625                 630                 635                 640
```

-continued

Asp Met Lys Ala Ile Glu Asp Leu Met Lys Thr Glu Asp Glu Tyr
                645                 650                 655
Glu Thr Leu Glu Arg Arg Tyr Ala Asn Glu Arg Asp Lys Ala Gln Phe
        660                 665                 670
Leu Ser Lys Glu Leu Glu His Val Lys Met Glu Leu Ala Lys Tyr Lys
            675                 680                 685
Leu Ala Glu Lys Thr Glu Thr Ser His Glu Gln Trp Leu Phe Lys Arg
        690                 695                 700
Leu Gln Glu Glu Ala Lys Ser Gly His Leu Ser Arg Glu Val Asp
705                 710                 715                 720
Ala Leu Lys Glu Lys Ile His Glu Tyr Met Ala Thr Glu Asp Leu Ile
                725                 730                 735
Cys His Leu Gln Gly Asp His Ser Val Leu Gln Lys Lys Leu Asn Gln
            740                 745                 750
Gln Glu Asn Arg Asn Arg Asp Leu Gly Arg Glu Ile Glu Asn Leu Thr
        755                 760                 765
Lys Glu Leu Glu Arg Tyr Arg His Phe Ser Lys Ser Leu Arg Pro Ser
770                 775                 780
Leu Asn Gly Arg Arg Ile Ser Asp Pro Gln Val Phe Ser Lys Glu Val
785                 790                 795                 800
Gln Thr Glu Ala Val Asp Asn Glu Pro Asp Tyr Lys Ser Leu Ile
                805                 810                 815
Pro Leu Glu Arg Ala Val Ile Asn Gly Gln Leu Tyr Glu Glu Ser Glu
            820                 825                 830
Asn Gln Asp Glu Asp Pro Asn Asp Glu Gly Ser Val Leu Ser Phe Lys
        835                 840                 845
Cys Ser Gln Ser Thr Pro Cys Pro Val Asn Arg Lys Leu Trp Ile Pro
        850                 855                 860
Trp Met Lys Ser Lys Glu Gly His Leu Gln Asn Gly Lys Met Gln Thr
865                 870                 875                 880
Lys Pro Asn Ala Asn Phe Val Gln Pro Gly Asp Leu Val Leu Ser His
                885                 890                 895
Thr Pro Gly Gln Pro Leu His Ile Lys Val Thr Pro Asp His Val Gln
            900                 905                 910
Asn Thr Ala Thr Leu Glu Ile Thr Ser Pro Thr Thr Glu Ser Pro His
        915                 920                 925
Ser Tyr Thr Ser Thr Ala Val Ile Pro Asn Cys Gly Thr Pro Lys Gln
    930                 935                 940
Arg Ile Thr Ile Leu Gln Asn Ala Ser Ile Thr Pro Val Lys Ser Lys
945                 950                 955                 960
Thr Ser Thr Glu Asp Leu Met Asn Leu Glu Gln Gly Met Ser Pro Ile
                965                 970                 975
Thr Met Ala Thr Phe Ala Arg Ala Gln Thr Pro Glu Ser Cys Gly Ser
            980                 985                 990
Leu Thr Pro Glu Arg Thr Met Ser Pro Ile Gln Val Leu Ala Val Thr
        995                 1000                1005
Gly Ser Ala Ser Ser Pro Glu Gln Gly Arg Ser Pro Glu Pro Thr
    1010                1015                1020
Glu Ile Ser Ala Lys His Ala Ile Phe Arg Val Ser Pro Asp Arg
        1025                1030                1035
Gln Ser Ser Trp Gln Phe Gln Arg Ser Asn Ser Asn Ser Ser Ser
        1040                1045                1050
Val Ile Thr Thr Glu Asp Asn Lys Ile His Ile His Leu Gly Ser

```
                 1055                1060                1065

Pro Tyr Met Gln Ala Val Ala Ser Pro Val Arg Pro Ala Ser Pro
    1070                1075                1080

Ser Ala Pro Leu Gln Asp Asn Arg Thr Gln Gly Leu Ile Asn Gly
    1085                1090                1095

Ala Leu Asn Lys Thr Thr Asn Lys Val Thr Ser Ser Ile Thr Ile
    1100                1105                1110

Thr Pro Thr Ala Thr Pro Leu Pro Arg Gln Ser Gln Ile Thr Val
    1115                1120                1125

Ser Asn Ile Tyr Asn
    1130

<210> SEQ ID NO 21
<211> LENGTH: 1135
<212> TYPE: PRT
<213> ORGANISM: Homo sapiens

<400> SEQUENCE: 21

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Leu Phe Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
            115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser His Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
            195                 200                 205

Gln Glu Ile Lys Ser Gln Glu Glu Lys Glu Gln Glu Lys Glu Lys Arg
    210                 215                 220

Val Thr Thr Leu Lys Glu Glu Leu Thr Lys Lys Ser Phe Ala Leu
225                 230                 235                 240

Met Val Val Asp Glu Gln Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270

Lys Leu Ala Leu Ala Glu Ala Arg Val Gln Glu Glu Glu Gln Lys Ala
            275                 280                 285

Thr Arg Leu Glu Lys Glu Leu Gln Thr Gln Thr Thr Lys Phe His Gln
```

-continued

```
              290                 295                 300
Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
                325                 330                 335

Leu Glu Glu Thr Asn Arg Ser Leu Arg Lys Ala Glu Glu Leu Gln
                340                 345                 350

Asp Ile Lys Glu Lys Ile Ser Lys Gly Glu Tyr Gly Asn Ala Gly Ile
                355                 360                 365

Met Ala Glu Val Glu Glu Leu Arg Lys Arg Val Leu Asp Met Glu Gly
    370                 375                 380

Lys Asp Glu Glu Leu Ile Lys Met Glu Glu Gln Cys Arg Asp Leu Asn
385                 390                 395                 400

Lys Arg Leu Glu Arg Glu Thr Leu Gln Ser Lys Asp Phe Lys Leu Glu
                405                 410                 415

Val Glu Lys Leu Ser Lys Arg Ile Met Ala Leu Glu Lys Leu Glu Asp
                420                 425                 430

Ala Phe Asn Lys Ser Lys Gln Glu Cys Tyr Ser Leu Lys Cys Asn Leu
                435                 440                 445

Glu Lys Glu Arg Met Thr Thr Lys Gln Leu Ser Gln Glu Leu Glu Ser
    450                 455                 460

Leu Lys Val Arg Ile Lys Glu Leu Glu Ala Ile Glu Ser Arg Leu Glu
465                 470                 475                 480

Lys Thr Glu Phe Thr Leu Lys Glu Asp Leu Thr Lys Leu Lys Thr Leu
                485                 490                 495

Thr Val Met Phe Val Asp Glu Arg Lys Thr Met Ser Glu Lys Leu Lys
                500                 505                 510

Lys Thr Glu Asp Lys Leu Gln Ala Ala Ser Ser Gln Leu Gln Val Glu
    515                 520                 525

Gln Asn Lys Val Thr Thr Val Thr Glu Lys Leu Ile Glu Glu Thr Lys
    530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu Glu
                565                 570                 575

Lys Gly Asn Asp Leu Leu Ser Arg Val Asn Met Leu Lys Asn Arg Leu
                580                 585                 590

Gln Ser Leu Glu Ala Ile Glu Lys Asp Phe Leu Lys Asn Lys Leu Asn
                595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Asp Leu Met Lys Thr Glu Asp Glu Tyr
                645                 650                 655

Glu Thr Leu Glu Arg Arg Tyr Ala Asn Glu Arg Asp Lys Ala Gln Phe
                660                 665                 670

Leu Ser Lys Glu Leu Glu His Val Lys Met Glu Leu Ala Lys Tyr Lys
                675                 680                 685

Leu Ala Glu Lys Thr Glu Thr Ser His Glu Gln Trp Leu Phe Lys Arg
    690                 695                 700

Leu Gln Glu Glu Glu Ala Lys Ser Gly His Leu Ser Arg Glu Val Asp
705                 710                 715                 720
```

```
Ala Leu Lys Glu Lys Ile His Glu Tyr Met Ala Thr Glu Asp Leu Ile
            725                 730                 735

Cys His Leu Gln Gly Asp His Ser Val Leu Gln Lys Lys Leu Asn Gln
        740                 745                 750

Gln Glu Asn Arg Asn Arg Asp Leu Gly Arg Glu Ile Glu Asn Leu Thr
            755                 760                 765

Lys Glu Leu Glu Arg Tyr Arg His Phe Ser Lys Ser Leu Arg Pro Ser
770                 775                 780

Leu Asn Gly Arg Arg Ile Ser Asp Pro Gln Val Phe Ser Lys Glu Val
785                 790                 795                 800

Gln Thr Glu Ala Val Asp Asn Gly Pro Pro Asp Tyr Lys Ser Leu Ile
                805                 810                 815

Pro Leu Glu Arg Ala Val Ile Asn Gly Gln Leu Tyr Glu Glu Ser Glu
            820                 825                 830

Asn Gln Asp Glu Asp Pro Asn Asp Glu Gly Ser Val Leu Ser Phe Lys
            835                 840                 845

Cys Ser Gln Ser Thr Pro Cys Pro Val Asn Arg Lys Leu Trp Ile Pro
850                 855                 860

Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895

Thr Pro Gly Gln Pro Leu His Ile Lys Val Thr Pro Asp His Val Gln
            900                 905                 910

Asn Thr Ala Thr Leu Glu Ile Thr Ser Pro Thr Glu Ser Pro His
            915                 920                 925

Ser Tyr Thr Ser Thr Ala Val Ile Pro Asn Cys Gly Thr Pro Lys Gln
930                 935                 940

Arg Ile Thr Ile Leu Gln Asn Ala Ser Ile Thr Pro Val Lys Ser Lys
945                 950                 955                 960

Thr Ser Thr Glu Asp Leu Met Asn Leu Glu Gln Gly Met Ser Pro Ile
                965                 970                 975

Thr Met Ala Thr Phe Ala Arg Ala Gln Thr Pro Glu Ser Cys Gly Ser
            980                 985                 990

Leu Thr Pro Glu Arg Thr Met Ser  Pro Ile Gln Val Leu Ala Val Thr
            995                 1000                1005

Gly Ser  Ala Ser  Ser Pro Glu  Gln Gly Arg Ser  Pro  Glu Pro Thr
    1010                1015                1020

Glu Ile  Ser Ala Lys His Ala  Ile Phe Arg Val Ser  Pro Asp Arg
    1025                1030                1035

Gln Ser  Ser Trp Gln Phe Gln  Arg Ser Asn Ser Asn  Ser Ser Ser
    1040                1045                1050

Val Ile  Thr Thr Glu Asp Asn  Lys Ile His Ile His  Leu Gly Ser
    1055                1060                1065

Pro Tyr  Met Gln Ala Val Ala  Ser Pro Val Arg Pro  Ala Ser Pro
    1070                1075                1080

Ser Ala  Pro Leu Gln Asp Asn  Arg Thr Gln Gly Leu  Ile Asn Gly
    1085                1090                1095

Ala Leu  Asn Lys Thr Thr Asn  Lys Val Thr Ser Ser  Ile Thr Ile
    1100                1105                1110

Thr Pro  Thr Ala Thr Pro Leu  Pro Arg Gln Ser Gln  Ile Thr Val
    1115                1120                1125

Glu Pro  Leu Leu Leu Pro His
    1130                1135
```

<210> SEQ ID NO 22
<211> LENGTH: 197
<212> TYPE: PRT
<213> ORGANISM: Homo sapiens

<400> SEQUENCE: 22

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
            195

<210> SEQ ID NO 23
<211> LENGTH: 186
<212> TYPE: PRT
<213> ORGANISM: Homo sapiens

<400> SEQUENCE: 23

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

```
Ser Gln Gly Lys Gly Ala Glu Gly Gln Arg Pro Gly Phe Gly Tyr Gly
        130                 135                 140

Gly Arg Ala Ser Asp Tyr Lys Ser Ala His Lys Gly Phe Lys Gly Val
145                 150                 155                 160

Asp Ala Gln Gly Thr Leu Ser Lys Ile Phe Lys Leu Gly Gly Arg Asp
                165                 170                 175

Ser Arg Ser Gly Ser Pro Met Ala Arg Arg
            180                 185

<210> SEQ ID NO 24
<211> LENGTH: 171
<212> TYPE: PRT
<213> ORGANISM: Homo sapiens

<400> SEQUENCE: 24

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
                20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Asp Ser His His Pro
        50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Pro Ser Gln Gly Lys Gly Arg Gly Leu Ser Leu
            100                 105                 110

Ser Arg Phe Ser Trp Gly Ala Glu Gly Gln Arg Pro Gly Phe Gly Tyr
        115                 120                 125

Gly Gly Arg Ala Ser Asp Tyr Lys Ser Ala His Lys Gly Phe Lys Gly
    130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170

<210> SEQ ID NO 25
<211> LENGTH: 160
<212> TYPE: PRT
<213> ORGANISM: Homo sapiens

<400> SEQUENCE: 25

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
                20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Asp Ser His His Pro
        50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Pro Ser Gln Gly Lys Gly Ala Glu Gly Gln Arg
```

```
                      100                 105                 110
Pro Gly Phe Gly Tyr Gly Gly Arg Ala Ser Asp Tyr Lys Ser Ala His
            115                 120                 125

Lys Gly Phe Lys Gly Val Asp Ala Gln Gly Thr Leu Ser Lys Ile Phe
            130                 135                 140

Lys Leu Gly Gly Arg Asp Ser Arg Ser Gly Ser Pro Met Ala Arg Arg
145                 150                 155                 160

<210> SEQ ID NO 26
<211> LENGTH: 253
<212> TYPE: PRT
<213> ORGANISM: Homo sapiens

<400> SEQUENCE: 26

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Gly Trp Gly Gln Pro His Gly Gly Gly
50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
            85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
        130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 27
<211> LENGTH: 244
<212> TYPE: PRT
<213> ORGANISM: Homo sapiens

<400> SEQUENCE: 27

Gly Leu Lys Gly Lys Arg Gly Asp Ser Gly Ser Pro Ala Thr Trp Thr
1               5                   10                  15

Thr Arg Gly Phe Val Phe Thr Arg His Ser Gln Thr Thr Ala Ile Pro
            20                  25                  30
```

```
Ser Cys Pro Glu Gly Thr Val Pro Leu Tyr Ser Gly Phe Ser Phe Leu
            35                  40                  45
Phe Val Gln Gly Asn Gln Arg Ala His Gly Gln Asp Leu Gly Thr Leu
 50                  55                  60
Gly Ser Cys Leu Gln Arg Phe Thr Thr Met Pro Phe Leu Phe Cys Asn
 65                  70                  75                  80
Val Asn Asp Val Cys Asn Phe Ala Ser Arg Asn Asp Tyr Ser Tyr Trp
                 85                  90                  95
Leu Ser Thr Pro Ala Leu Met Pro Met Asn Met Ala Pro Ile Thr Gly
            100                 105                 110
Arg Ala Leu Glu Pro Tyr Ile Ser Arg Cys Thr Val Cys Glu Gly Pro
        115                 120                 125
Ala Ile Ala Ile Ala Val His Ser Gln Thr Thr Asp Ile Pro Pro Cys
    130                 135                 140
Pro His Gly Trp Ile Ser Leu Trp Lys Gly Phe Ser Phe Ile Met Phe
145                 150                 155                 160
Thr Ser Ala Gly Ser Glu Gly Thr Gly Gln Ala Leu Ala Ser Pro Gly
                165                 170                 175
Ser Cys Leu Glu Glu Phe Arg Ala Ser Pro Phe Leu Glu Cys His Gly
            180                 185                 190
Arg Gly Thr Cys Asn Tyr Tyr Ser Asn Ser Tyr Ser Phe Trp Leu Ala
        195                 200                 205
Ser Leu Asn Pro Glu Arg Met Phe Arg Lys Pro Ile Pro Ser Thr Val
    210                 215                 220
Lys Ala Gly Glu Leu Glu Lys Ile Ile Ser Arg Cys Gln Val Cys Met
225                 230                 235                 240
Lys Lys Arg His

<210> SEQ ID NO 28
<211> LENGTH: 42
<212> TYPE: PRT
<213> ORGANISM: Homo sapiens

<400> SEQUENCE: 28

Asp Ala Glu Phe Arg His Asp Ser Gly Tyr Glu Val His His Gln Lys
 1               5                  10                  15
Leu Val Phe Phe Ala Glu Asp Val Gly Ser Asn Lys Gly Ala Ile Ile
                20                  25                  30
Gly Leu Met Val Gly Gly Val Val Ile Ala
            35                  40

<210> SEQ ID NO 29
<211> LENGTH: 13
<212> TYPE: PRT
<213> ORGANISM: Artificial Sequence
<220> FEATURE:
<223> OTHER INFORMATION: Artificial sequence - GPBP_DeltaFFAT

<400> SEQUENCE: 29

Leu Ile Asn Glu Glu Glu Phe Ala Ala Leu Asp Arg Gln
 1               5                  10

<210> SEQ ID NO 30
<211> LENGTH: 20
<212> TYPE: PRT
<213> ORGANISM: Homo sapiens

<400> SEQUENCE: 30
```

-continued

```
Arg Arg Thr Glu Glu Ala Tyr Lys Asn Ala Met Thr Glu Leu Lys Lys
1               5                   10                  15

Lys Ser His Phe
            20

<210> SEQ ID NO 31
<211> LENGTH: 20
<212> TYPE: PRT
<213> ORGANISM: Homo sapiens

<400> SEQUENCE: 31

Gly Gly Pro Asp Tyr Glu Glu Gly Pro Asn Ser Leu Ile Asn Glu Glu
1               5                   10                  15

Glu Phe Phe Asp
            20

<210> SEQ ID NO 32
<211> LENGTH: 20
<212> TYPE: PRT
<213> ORGANISM: Homo sapiens

<400> SEQUENCE: 32

Ala Val Glu Ala Ala Leu Asp Arg Gln Asp Lys Ile Glu Glu Gln Ser
1               5                   10                  15

Gln Ser Glu Lys
            20

<210> SEQ ID NO 33
<211> LENGTH: 20
<212> TYPE: PRT
<213> ORGANISM: Homo sapiens

<400> SEQUENCE: 33

Val Arg Leu His Trp Pro Thr Ser Leu Pro Ser Gly Asp Ala Phe Ser
1               5                   10                  15

Ser Val Gly Thr
            20
```